(12) United States Patent
Park et al.

(10) Patent No.: US 7,812,045 B2
(45) Date of Patent: Oct. 12, 2010

(54) ANTIFUNGAL TRIAZOLE DERIVATIVES

(75) Inventors: Joon Seok Park, Yongin-si (KR); Kyung A Yu, Seoul (KR); Il Yeong Jeong, Chungju-si (KR)

(73) Assignee: Daewoong Pharmaceutical Co., Ltd., Seongnam-Si (KR)

( * ) Notice: Subject to any disclaimer, the term of this patent is extended or adjusted under 35 U.S.C. 154(b) by 473 days.

(21) Appl. No.: 11/910,014

(22) PCT Filed: Mar. 30, 2006

(86) PCT No.: PCT/KR2006/001119

§ 371 (c)(1), (2), (4) Date: Sep. 28, 2007

(87) PCT Pub. No.: WO2006/109933

PCT Pub. Date: Oct. 19, 2006

(65) Prior Publication Data

US 2008/0194661 A1     Aug. 14, 2008

(30) Foreign Application Priority Data

Mar. 30, 2005   (KR) .................. 10-2005-0026824

(51) Int. Cl.
*A61K 31/41*     (2006.01)
*C07D 233/00*   (2006.01)
*C07D 249/00*   (2006.01)

(52) U.S. Cl. .............. 514/383; 514/403; 548/262.2; 548/356.1

(58) Field of Classification Search ........... 514/383, 514/403; 548/262.2, 356.1
See application file for complete search history.

(56) References Cited

U.S. PATENT DOCUMENTS 4,587,239 A * 5/1986 Regel et al. .......... 514/184
5,648,372 A   7/1997 Naito et al.

FOREIGN PATENT DOCUMENTS

| EP | 0121888 A2 | 10/1984 |
| EP | 0548553 A1 | 6/1993 |
| EP | 1322638 A1 | 7/2003 |

* cited by examiner

*Primary Examiner*—Susannah Chung
(74) *Attorney, Agent, or Firm*—Sughrue Mion, PLLC

(57) ABSTRACT

Disclosed herein are antifungal triazole derivatives or pharmaceutically acceptable salts thereof, a preparation method thereof, and a pharmaceutical composition comprising the same.

9 Claims, No Drawings

ANTIFUNGAL TRIAZOLE DERIVATIVES

This is a National Stage Application under 35 U.S.C. §371 of PCT/KR2006/001119 filed Mar. 30, 2006 which claims priority to Korean Patent Application 10-2005-0026824 filed Mar. 30, 2005, all of which are incorporated herein by reference.

TECHNICAL FIELD

The present invention relates to novel antifungal triazole derivatives, pharmaceutically acceptable salts thereof, preparation methods therefor, and a pharmaceutical composition containing the same.

BACKGROUND ART

Patients who undergo chemical therapy for cancer, who receive organ implants, or who have HIV or AIDS are at a great risk of fungal infection, mostly with opportunistic pathogens, such as *Candida* spp., *Aspergillus* spp. and *Cryptococcus neoformans*. The antifungals available in the market suffer with drawbacks such as toxicity and narrow spectrum of activity. As patients who become "immunocompromised" are currently increasing in number and contract serious fungal infections, there is an increasing demand for antifungal agents that have excellent inherent pharmacokinetic characteristics and potent inhibitory activities against a broad range of fungi.

A number of derivatives having antifungal activity is known and has been developed for the treatment of mammals, including humans, infected with fungi. For example, orally administrable triazole derivatives were reported in the late 1980s, and are represented by Fluconazole (UK Pat. No. 2099818), Itraconazole (U.S. Pat. No. 4,267,179) and particularly, Voriconazole (EU Pat. No. 0440372). None of them, however, show remarkable inhibitory activity against some of the opportunistic fungi which cause fatal infections in patients having decreased immunity.

Many of the antifungal agents which have been developed or are now under study are found to have additional heterocyclic substituents in addition to triazole. For instance, fluconazole has five-membered heterocyclic ring, while a six-membered heterocyclic ring is contained in voriconazole. In addition, isoxazole (EU Pat. No. 0241232, Shionogi Co.) and triazolone (EU Pat. No. 0659751, Takeda Co.) have respectively five-membered heterocyclic rings. In addition, bicyclic heterogroups are found in quinazolinone (Korean Pat. Laid-Open Publication No. 2002-0075809, Uriach Co.), quinoline (Korean Pat. Laid-Open Publication No. 1996-7003895, Fujisawa Co.), benzotriazole (U.S. Pat. No. 5,648,372, Eisai Co), benzimidazole (Chinese Pat. No. 1081189), and indole (US Pat. Publication No. 2004/67998).

DISCLOSURE OF THE INVENTION

One object of the present invention is to provide triazole derivatives having antifungal activity, isomers thereof, or pharmaceutically acceptable salts thereof, and a method for the preparation thereof.

Another object of the present invention is to provide antifungal compositions comprising the said triazole derivatives, or isomers or pharmaceutically acceptable salts thereof.

BEST MODE FOR CARRYING OUT THE INVENTION

In one embodiment, the present invention relates to a triazole derivative having the following chemical formula 1, an isomer thereof, and a pharmaceutically acceptable salt thereof:

[Chemical Formula 1]

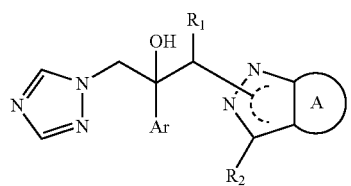

wherein,

Ar is phenyl substituted with at least one halogen or $C_1$-$C_4$ haloalkyl;

$R_1$ is hydrogen, one or two fluorine atoms, or a $C_1$-$C_3$ lower alkyl;

$R_2$ is hydrogen, halogen, a $C_1$-$C_3$ lower alkyl, $C_1$-$C_4$ haloalkyl, $C_1$-$C_4$ alkoxy, nitro, cyano, amino, hydroxy, —$NR_3R_4$, —$CONR_3R_4$, —$CH_2$—OCO—$R_3$, —CO—$R_3$, —$COOR_3$, —$C(=NR_4)NHR_3$, or —$C(=NR_4)OR_3$;

A is a benzene ring or a 5- or 6-membered heterocyclic ring containing one or more heteroatoms selected from among N, O and S, and may be non-fused or fused with a benzene ring or a 5- or 6-membered heterocyclic ring containing one or more heteroatoms selected from among N, O and S, with no or at least one substituent X therein, X being hydrogen, a $C_1$-$C_4$ alkyl, $C_3$-$C_6$ cycloalkyl, $C_1$-$C_4$ haloalkyl, $C_1$-$C_4$ alkoxy, $C_1$-$C_4$ haloalkoxy, halogen, nitro, cyano, hydroxy, benzyloxy, hydroxymethyl, —$NR_3R_4$, —$NR_3COR_4$, —$NR_3SO_2R_4$, —$CONR_3R_4$, —$CH_2$—OCO—$R_3$, —CO—$R_3$, $COOR_3$, —$SO_2R_3$, —$C(=NR_4)NHR_3$, —$C(=NR_4)OR_3$, or a 5-, 6-, or 7-membered heterocyclic ring containing at least one heteroatom selected from among N, O and S;

$R_3$ is hydrogen, a $C_1$-$C_4$ alkyl, $C_3$-$C_6$ cycloalkyl, a 5- or 6-membered heterocyclic ring containing at least one heteroatom selected from among N, O and S, —$CH_2COR_4$, —$CH_2CONR_4$ or aryl $C_1$-$C_4$ alkyl, the aryl moiety being a phenyl group non-substituted or substituted with at least one halogen, $C_1$-$C_4$ alkyl, $C_1$-$C_4$ haloalkyl, $C_1$-$C_4$ alkoxy, $C_1$-$C_4$ haloalkoxy, nitro, cyano, hydroxy, benzyloxy, phenyl or hydroxymethyl, or being a bicyclic ring in which a 5- or 6-membered heterocyclic ring containing at least one heteroatom selected from among N, O and S is fused to a benzene ring;

$R_4$ is hydrogen, a $C_1$-$C_4$ alkyl, $C_3$-$C_6$ cycloalkyl, —$COR_3$, —$COCF_3$, —$CHR_7NHR_3R_4$, —$CHR_7COR_3$, or the same aryl $C_1$-$C_4$ alkyl as defined in $R_3$;

$R_5$ is hydrogen, —$CONH_2$, —$COCH_3$, —CN, —$SO_2NHR_3$, —$SO_2R_3$, —$OR_3$, —$OCOR_3$ or —($C_{1-4}$ alkyl)-$NH_2$;

$R_6$ is $C_1$-$C_4$ alkyl;

$R_7$ is an α- or β-amino acid residue, whether D or L type, selected from 20 amino acid residues;

z is 0, 1 or 2; and the dotted lines ( . . . ) represent double bonds, wherein the nitrogen atom of position 1 or 2 in the pyrazole ring is bonded to the propanol substituted with the triazole ring, Ar and $R_1$.

In Chemical Formula 1, according to a preferred embodiment of the present invention, Ar is phenyl substituted with two or more halogens or $C_1$-$C_4$ haloalkyl;

$R_1$ is hydrogen, one or two fluorine atoms, or $C_1$-$C_3$ lower alkyl;

$R_2$ is hydrogen, halogen, $C_1$-$C_3$ lower alkyl, $C_1$-$C_4$ haloalkyl, $C_1$-$C_4$ alkoxy, nitro, cyano, amino, hydroxy, —$NR_3R_4$, —$CONR_3R_4$, —$CH_2$—OCO—$R_3$, —CO—$R_3$, —$COOR_3$, —C(=$NR_4$)$NHR_3$, —C(=$NR_4$)$OR_3$;

A is a benzene ring or a 5- or 6-membered heterocyclic ring containing one or more heteroatoms selected from among N, O and S, and may be non-fused or fused with a benzene ring or a 5- or 6-membered heterocyclic ring containing one or more heteroatoms selected from among N, O and S, with no or at least one substituent X therein, X being hydrogen, a $C_1$-$C_4$ alkyl, $C_3$-$C_6$ cycloalkyl, $C_1$-$C_4$ haloalkyl, $C_1$-$C_4$ alkoxy, $C_1$-$C_4$ haloalkoxy, halogen, nitro, cyano, hydroxy, benzyloxy, —$NR_3R_4$, —$NR_3COR_4$, —$NR_3SO_2R_4$, —$CONR_3R_4$, —$CH_2$—OCO—$R_3$, —CO—$R_3$, —$COOR_3$, —$SO_2R_3$, —C(=$NR_4$)$NHR_3$, —C(=$NR_4$)$OR_3$, or a 5-, 6-, or 7-membered heterocyclic ring containing at least one heteroatom selected from among N, O and S;

$R_3$ is hydrogen, a $C_1$-$C_4$ alkyl, $C_3$-$C_6$ cycloalkyl, a 5- or 6-membered heterocyclic ring containing at least one heteroatom selected from among N, O and S, —$CH_2COR_4$, —$CH_2CONR_4$ or aryl $C_1$-$C_4$ alkyl, the aryl moiety being a phenyl group non-substituted or substituted with at least one halogen, $C_1$-$C_4$ alkyl, $C_1$-$C_4$ haloalkyl, $C_1$-$C_4$ alkoxy, $C_1$-$C_4$ haloalkoxy, nitro, cyano, hydroxy, benzyloxy, phenyl or hydroxymethyl, or being a bicyclic ring in which a 5- or 6-membered heterocyclic ring containing at least one heteroatom selected from among N, O and S is fused to a benzene ring;

$R_4$ is hydrogen, a $C_1$-$C_4$ alkyl, $C_3$-$C_6$ cycloalkyl, —$COR_3$, —$COCF_3$, —$CHR_7NHR_3R_4$, —$CHR_7COR_3$ or the same aryl $C_1$-$C_4$ alkyl as defined in $R_3$;

$R_5$ is hydrogen, —$CONH_2$, —$COCH_3$, —CN, —$SO_2NHR_3$, —$SO_2R_3$, —$OR_3$, —$OCOR_3$ or —($C_{1-4}$ alkyl)-$NH_2$;

$R_6$ is $C_1$-$C_4$ alkyl;

$R_7$ is an α- or β-amino acid residue, whether D or L type, selected from 20 amino acid residues;

z is 1 or 2; and the dotted lines ( . . . ) represent double bonds, wherein the nitrogen atom of position 1 or 2 in the pyrazole ring is bonded to the propanol substituted with the triazole ring, Ar and $R_1$.

In a more preferable embodiment, the compound of Chemical Formula 1 is:

2-(2,4-difluorophenyl)-1-(1H-indazol-1-yl)-3-(1H-1,2,4-triazol-1-yl)propan-2-ol (1), 1-(5-(4-trifluoromethyl-benzylamino)-1H-indazol-1-yl)-2-(2,4-difluorophenyl)-3-(1H-1,2,4-triazol-1-yl)propan-2-ol, 1-(5-(4-trifluoromethyl-benzylamino)-1H-indazol-2-yl)-2-(2,4-difluorophenyl)-3-(1H-2,4-triazol-1-yl)propan-2-ol, 1-(5-(4-fluoro-benzylamino)-1H-indazol-2-yl)-2-(2,4-difluorophenyl)-3-(1H-1,2,4-triazol-1-yl)propan-2-ol, 1-(5-(4-chloro-benzylamino)-1H-indazol-2-yl)-2-(2,4-difluorophenyl)-3-(1H-1,2,4-triazol-1-yl)propan-2-ol, 1-(5-(4-bromo-benzylamino)-1H-indazol-2-yl)-2-(2,4-difluorophenyl)-3-(1H-1,2,4-triazol-1-yl)propan-2-ol, 1-(5-(4-nitro-benzylamino)-1H-indazol-2-yl)-2-(2,4-difluorophenyl)-3-(1H-1,2,4-triazol-1-yl)propan-2-ol, 1-(5-(biphenyl-4-yl-methyl-amino)-1H-indazol-2-yl)-2-(2,4-difluorophenyl)-3-(1H-1,2,4-triazol-1-yl)propan-2-ol, 1-(5-(4-benzyloxy-benzylamino)-1H-indazol-2-yl)-2-(2,4-difluorophenyl)-3-(1H-1,2,4-triazol-1-yl)propan-2-ol, 1-(5-(2,4-dichloro-benzylamino)-1H-indazol-2-yl)-2-(2,4-difluorophenyl)-3-(1H-1,2,4-triazol-1-yl)propan-2-ol, 1-(5-(2-chlorobenzylamino)-1H-indazol-1-yl)-2-(2,4-difluorophenyl)-3-(1H-1,2,4-triazol-1-yl)propan-2-ol, 1-(5-(2-chlorobenzylamino)-2H-indazol-2-yl)-2-(2,4-difluorophenyl)-3-(1H-1,2,4-triazol-1-yl)propan-2-ol, 2-(2,4-difluorophenyl)-1-(1H-1,2,4-triazol-1-yl)-3-(5-(2-(trifluoromethyl)benzylamino)-1H-indazol-1-yl)propan-2-ol, 2-(2,4-difluorophenyl)-1-(1H-1,2,4-triazol-1-yl)-3-(5-(2-(trifluoromethyl)benzylamino)-2H-indazol-2-yl)propan-2-ol, 4-((2-(2-(2,4-difluorophenyl)-2-hydroxy-3(1H-1,2,4-triazol-1-yl)propyl)-2H-indazol-5-ylamino)methyl)benzonitrile, 2-(2,4-difluorophenyl)-1-(1H-1,2,4-triazol-1-yl)-3-(5-(4-(trifluoromethoxy)benzylamino)-2H-indazol-2-yl)propan-2-ol, 1-(5-2,4-difluorobenzylamino)-1H-indazol-1-yl)-2-(2,4-difluorophenyl)-3-(1H-1,2,4,-triazol-1-yl)propan-2-ol, 1-(5-(2,6-difluorobenzylamino)-2H-indazol-2-yl)-2-(2,4-difluorophenyl)-3-(1H-1,2,4-triazol-1-yl)propan-2-ol, 1-(5-(2,6-dichlorobenzylamino)-2H-indazol-2-yl)-2-(2,4-difluorophenyl)-3-(1H-1,2,4,-triazol-1-yl)propan-2-ol, tert-butyl-4-(1-((2R,3R)-3-(2,4-difluorophenyl)-3-hydroxy-4-(1H-1,2,4-triazol-1-yl)butan-2-yl)-1H-indazol-5-ylamino)piperidine-1-carboxylate, (2R,3R)-2-(2,4-difluorophenyl)-3-(5-(tetrahydro-2H-thiopyran-4-ylamino)-2H-indazol-2-yl)-1-(1H-1,2,4-triazol-1-yl)butan-2-ol, (2R,3R)-2-(2,4-difluorophenyl)-3-(5-fluoro-1H-indazol-1-yl)-1-(1H-1,2,4-triazol-1-yl)butan-2-ol, (2R,3R)-2-(2,4-difluorophenyl)-3-(5-fluoro-2H-indazol-2-yl)-1-(1H-1,2,4-triazol-1-yl)butan-2-ol, (2R,3R)-3-(5-chloro-1H-indazol-1-yl)-2-(2,4-difluorophenyl)-1-(1H-1,2,4-triazol-1-yl)butan-2-ol, (2R,3R)-3-(5-chloro-2H-indazol-2-yl)-2-(2,4-difluorophenyl)-1-(1H-1,2,4-triazol-1-yl)butan-2-ol, (3R)-3-(5-bromo-1H-indazol-1-yl)-2-(2,4-difluorophenyl)-1-(1H-1,2,4-triazol-1-yl)butan-2-ol, (2R,3R)-3-(5-bromo-2H-indazol-2-yl)-2-(2,4-difluorophenyl)-1-(1H-1,2,4-triazol-1-yl)butan-2-ol, 1-((2R)-3-(2,4-triazole)-3-hydroxy-4-(1H-1,2,4-triazol-1-yl)butan-2-yl)-1H-indazole-5-carbonitrile, (2R,3R)-2-(2,4-difluorophenyl)-3-(5-nitro-3-phenyl-2H-indazol-2-yl)-1-(1H-1,2,4-triazol-1-yl)butan-2-ol, (2R,3R)-2-(2,4-difluorophenyl)-3-(5-fluoro-3-methyl-1H-indazol-1-yl)-1-(1H-1,2,4-triazol-1-yl)butan-2-ol, (2R,3R)-2-(2,4-difluorophenyl)-3-(5-fluoro-3-methyl-2H-indazol-2-yl)-1-(1H-1,2,4-triazol-1-yl)butan-2-ol, (2R,3R)-2-(2,4-difluorophenyl)-3-(3-methyl-5-(trifluoromethyl)-1H-indazol-1-yl)-1-(1H-1,2,4-triazol-1-yl)butan-2-ol, (2R,3R)-2-(2,4-difluorophenyl)-3-(3-methyl-5-(trifluoromethyl)-2H-indazol-2-yl)-1-(1H-1,2,4-triazol-1-yl)butan-2-ol, (2R,3R)-2-(2,4-difluorophenyl)-3-(3-methyl-5-nitro-1H-indazol-1-yl)-1-(1H-1,2,4-triazol-1-yl)butan-2-ol, (2R,3R)-3-(5,6-difluoro-3-methyl-1H-indazol-1-yl)-2-(2,4-difluorophenyl)-1-(1H-1,2,4-triazol-1-yl)butan-2-ol, (2R,3R)-3-(6-chloro-5-fluoro-3-methyl-1H-indazol-1-yl)-2-(2,4-difluorophenyl)-1-(1H-1,2,4-triazol-1-yl)butan-2-ol,
(2R,3R)-3-(6-chloro-5-fluoro-3-methyl-2H-indazol-2-yl)-2-(2,4-difluorophenyl)-1-(1H-1,2,4-triazol-1-yl)butan-2-ol,
(2R,3R)-2-(2,4-difluorophenyl)-3-(3-ethyl-5-fluoro-1H-indazol-1-yl)-1-(1H-1,2,4-triazol-1-yl)butan-2-ol,
(2R,3R)-3-(5-chloro-3-methyl-1H-indazol-1-yl)-2-(2,4-difluorophenyl)-1-(1H-1,2,4-triazol-1-yl)butan-2-ol,
(2R,3R)-3-(5-chloro-3-methyl-2H-indazol-2-yl)-2-(2,4-difluorophenyl)-1-(1H-1,2,4-triazol-1-yl)butan-2-ol,
(2R,3R)-3-(5-bromo-3-ethyl-1H-indazol-1-yl)-2-(2,4-difluorophenyl)-1-(1H-1,2,4-triazol-1-yl)butan-2-ol,
(2R,3R)-3-(5-bromo-3-ethyl-2H-indazol-2-yl)-2-(2,4-difluorophenyl)-1-(1H-1,2,4-triazol-1-yl)butan-2-ol,
(2R,3R)-3-(3,5-difluoro-1H-indazol-1-yl)-2-(2,4-difluorophenyl)-1-(1H-1,2,4-triazol-1-yl)butan-2-ol,
(2R,3R)-3-(3,5-difluoro-2H-indazol-1-yl)-2-(2,4-difluorophenyl)-1-(1H-1,2,4-triazol-1-yl)butan-2-ol,
(2R,3R)-3-(5-chloro-3-fluoro-1H-indazol-1-yl)-2-(2,4-difluorophenyl)-1-(1H-1,2,4-triazol-1-yl)butan-2-ol,
(2R,3R)-3-(5-chloro-3-fluoro-2H-indazol-1-yl)-2-(2,4-difluorophenyl)-1-(1H-1,2,4-triazol-1-yl)butan-2-ol,
1-((2R,3R)-3-(2,4-difluorophenyl)-3-hydroxy-4-(1H-1,2,4-triazol-1-yl)butan-2-yl)-3-fluoro-1H-indazol-5-carbonitrile,
1-((2R,3R)-3-(2,4-difluorophenyl)-3-hydroxy-4-(1H-1,2,4-triazol-1-yl)butan-2-yl)-3-fluoro-2H-indazol-5-carbonitrile,
(2R,3R)-3-(5-bromo-3-methyl-1H-indazol-1-yl)-2-(2,4-difluorophenyl)-1-(1H-1,2,4-triazol-1-yl)butan-2-ol,
(2R,3R)-3-(5-bromo-3-methyl-2H-indazol-2-yl)-2-(2,4-difluorophenyl)-1-(1H-1,2,4-triazol-1-yl)butan-2-ol,
1-((2R,3R)-3-(2,4-difluorophenyl)-3-hydroxy-4-(1H-1,2,4-triazol-1-yl)butan-2-yl)-3-methyl-1H-indazol-5-carbonitrile,
1-((2R,3R)-3-(2,4-difluorophenyl)-3-hydroxy-4-(1H-1,2,4-triazol-1-yl)butan-2-yl)-3-methyl-2H-indazol-5-carbonitrile,
(2R,3R)-3-(5-(4-chlorobenzylamino)-3-fluoro-1H-indazol-1-yl)-2-(2,4-difluorophenyl)-1-(1H-1,2,4-triazol-1-yl)butan-2-ol,
(2R,3R)-3-(5-(4-chlorobenzylamino)-3-fluoro-2H-indazol-1-yl)-2-(2,4-difluorophenyl)-1-(1H-1,2,4-triazol-1-yl)butan-2-ol,
(2R,3R)-3-(3-amino-5-fluoro-1H-indazol-1-yl)-2-(2,4-difluorophenyl)-1-(1H-1,2,4-triazol-1-yl)butan-2-ol,
(2R,3R)-3-(3-amino-5-fluoro-2H-indazol-1-yl)-2-(2,4-difluorophenyl)-1-(1H-1,2,4-triazol-1-yl)butan-2-ol,
(2R,3R)-3-(3-amino-5-chloro-1H-indazol-1-yl)-2-(2,4-difluorophenyl)-1-(1H-1,2,4-triazol-1-yl)butan-2-ol, or
(2R,3R)-3-(3-amino-5-chloro-2H-indazol-1-yl)-2-(2,4-difluorophenyl)-1-(1H-1,2,4-triazol-1-yl)butan-2-ol.

The term "halogen" or "halo", as used herein, represents halogen atoms, including fluorine, chlorine, bromine, iodine, etc.

Unless otherwise specified, the term "alkyl", as used herein, means a straight or branched saturated hydrocarbon radical having 1 to 4 carbon atoms, exemplified by methyl, ethyl, propyl, isopropyl, butyl, isobutyl, sec-butyl or tert-butyl.

Unless otherwise specified, the term "haloalkyl", as used herein, means a radical in which one or more hydrogen atoms of the alkyl group (as defined above) are replaced with one or more identical or different halogen atoms, examples of which include trifluoromethyl, trichloromethyl, fluoromethyl, chloromethyl, bromomethyl, iodomethyl, difluoromethyl, dichloromethyl, 2-chloroethyl, 2,2-dichloroethyl, 2,2,2-trichloroethyl, pentachloroethyl, 2-fluoroethyl, 2,2-difluoroethyl, 2,2,2-trifluoroethyl, pentafluoroethyl, 3-chloropropyl, 3,3-dichloropropyl, 3,3,3-trichloropropyl, 2,2,3,3,3-pentachloropropyl, 3-fluoropropyl, 3,3-difluoropropyl, 3,3,3-trifluoropropyl, 2,2,3,3-tetrafluoropropyl, 2,2,3,3,3-pentafluoropropyl, heptafluoropropyl, 4-chlorobutyl, 4-fluorobutyl, 4-iodobutyl and 4-bromobutyl.

As used herein, the term "cycloalkyl", unless otherwise specified, means a saturated cyclic hydrocarbon radical having 3 to 6 carbon atoms, exemplified by cyclopropyl, cyclobutyl, cyclopentyl or cyclohexyl.

As used herein, the term "alkoxy", unless otherwise specified, means O-alkyl (the alkyl moiety is as defined above), exemplified by methoxy, ethoxy, propoxy, isopropoxy, butoxy, isobutoxy, sec-butoxy, tert-butoxy and the like.

As used herein, the term "haloalkoxy", unless otherwise specified, means an alkoxy radical (as defined above) in which one or more hydrogen atoms are substituted with one or more identical or different halogen atoms. Illustrative, non-limiting examples thereof include trifluoromethoxy, fluoromethoxy, 2-chloroethoxy, 2-fluoroethoxy, 2,2-difluoroethoxy, 2-iodoethoxy, 2,2-difluoroethoxy, 2,2,2-trifluoroethoxy, pentafluoroethoxy, 3-fluoropropoxy, 3-chloropropoxy, 2,2,3,3-tetrafluoropropoxy, 2,2,3,3,3-pentafluoropropoxy, heptafluoropropoxy, 4-fluorobutoxy and 4-chlorobutoxy.

The term "heterocyclic ring or compound", as used herein, means a ring structure, whether aliphatic or aromatic, containing atoms in addition to carbon, such as O, N or S, as a part of the ring.

The term "aryl", as used herein, means an aromatic hydrocarbon radical, exemplified by phenyl or naphthyl, unless otherwise stated.

The compound of Chemical Formula 1 according to the present invention contains two chiral centers at C2 and C3 positions. According to their absolute configurations, the compound of Chemical Formula 1 may be, for example, a (2R/S)-racemate or a (2R,3R)-diastereomer. Therefore, it should be understood that the compound of the present invention includes all possible stereoisomers, unless otherwise specified.

One preferred embodiment of the present invention provides pharmaceutical acceptable salts of the compound of Chemical Formula 1. As for the pharmaceutically acceptable salts of the compound of Chemical Formula 1, they may comprise inorganic or organic salts known to the art relating to the antifungal agent and may be prepared using well-known methods to the art. Examples of the pharmaceutically acceptable salts include, but are not limited to, salts comprising inorganic acids such as hydrochloric acid, bromic acid, sulfuric acid, phosphoric acid, etc., organic acids such as acetic acid, citric acid, fumaric acid, lactic acid, maleic acid, succinic acid, tartaric acid, etc., alkaline metals such as sodium, potassium, etc., and organic bases such as ammonia, trimethylamine, triethylamine, pyridine, picoline, 2,6-rutidine, ethanolamine, diethanolamine, triethanolamine, cyclohexylamine, dicyclohexylamine, etc.

In accordance with another embodiment, the present invention relates to a method for preparing the compound of Chemical Formula 1, isomers thereof or pharmaceutically acceptable salts thereof, comprising the reaction of a compound of Chemical Formula 2 with a compound of Chemical Formula 3 in the presence of a base, or the reaction of a compound of Chemical Formula 4 with a compound of Chemical Formula 5:

[Chemical Formula 2]

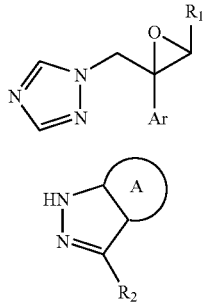

[Chemical Formula 3]

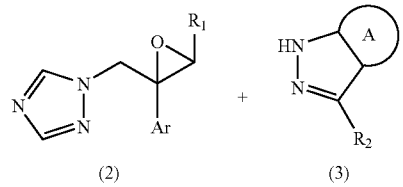

wherein, Ar, $R_1$, $R_2$ and A are all as defined above.

In more detail, the preparation of the compound of Chemical Formula 1 through the reaction of the compound of Chemical Formula 2 with the compound of Chemical Formula 3 in the presence of a base can be represented by the following Reaction formula 1. In this case, the positions of nitrogen atoms in the indazole moiety allow two possible positional isomers.

(Reaction Formula 1)

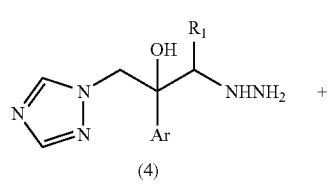

Alternatively, the compound of Chemical Formula 1 may be synthesized by using the method described in the literature [*J. Med. Chem.* 2004, 24, 6435-6438] and reacting the compound of Chemical Formula 4, obtainable from the compound of Chemical Formula 2 with the compound of Chemical Formula 5. In chemical formula 5, Y may represent a halogen atom, particularly fluorine, chlorine, and bromine atom, or may be a methanesulfonyloxy group. The compound of Chemical Formula 5 is commercially available or may be prepared according to a conventional method (as shown in Reaction Formula 4, below):

(Reaction Formula 2)

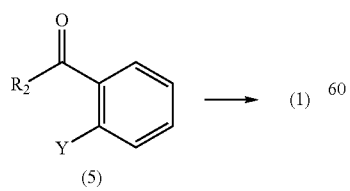

As a starting compound for the compound of Chemical Formula 2, an epoxide is well known and can be prepared, as shown in Reaction Formula 3, using the method described in the literature [*Chem. Pharm. Bull.,* 1993, 41(6), 1035-1042]:

(Reaction Formula 3)

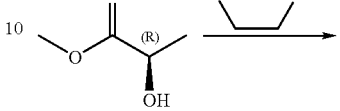

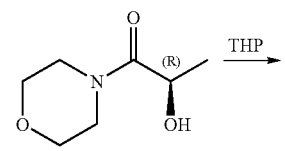

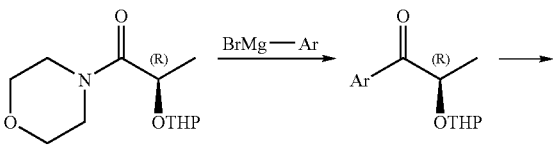

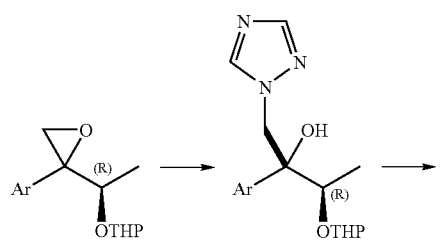

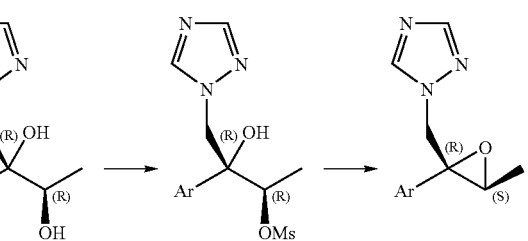

The compound of Chemical Formula 3 is commercially available or can be prepared, as shown in Reaction Formula 4, using a well-known method [*Tetrahedron,* 58, 6061-6067 (2002); U.S. Pat. No. 6,931,76; *J. Med. Chem.,* 37, 2721-2734 (1994); *Synthesis,* 588-592 (1999); *Org. Proc. Res. & Dev.,* 5, 587-592 (2001); *Bioorg. Med. Chem. Lett.,* 11, 1153-1156 (2001); *Tetrahedron,* 55, 6917-6922 (1999), etc.]:

(Reaction Formula 4)

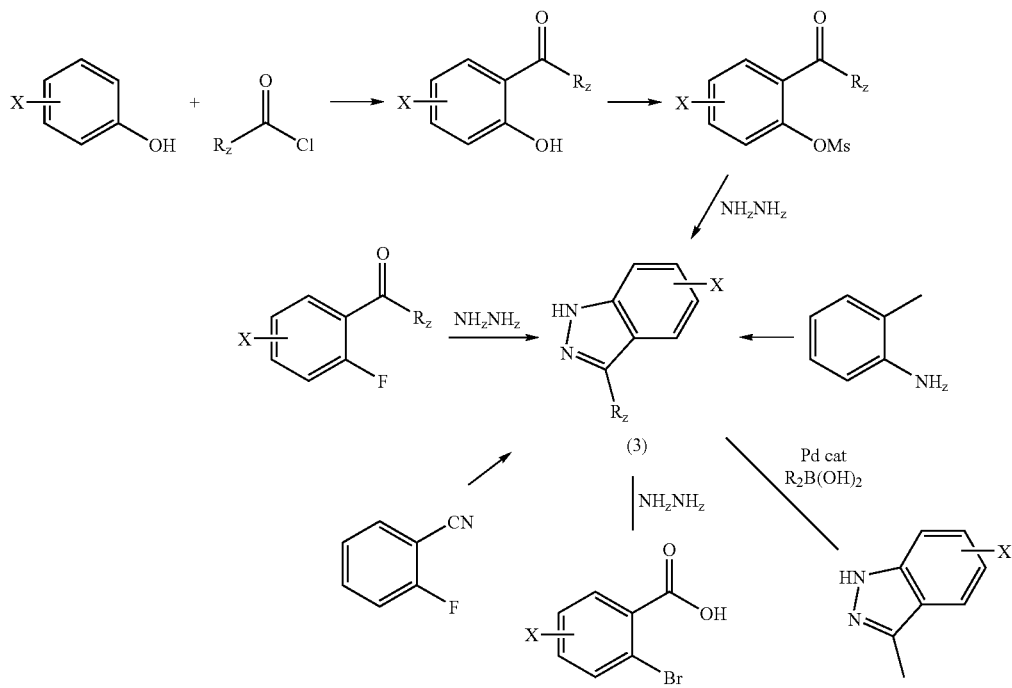

The reaction for the synthesis of the compound according to the present invention may be carried out in a polar organic solvent which is preferably exemplified by methanol, acetonitrile, dimethoxyethane, dimethylformamide, dimethylacetamide, dimethylsulfoxide, tetrahydrofuran, etc.

A base useful in the present invention may be an inorganic base such as sodium hydride (NaH), potassium carbonate ($K_2CO_3$) or sodium methoxide (NaOMe), or an organic base such as triethylamine or 1,8-diazabicyclo[5,4,0]undec-7-en (DBU).

The preparative reaction for the compound of the present invention is performed at 0 to 150° C., and preferably at 0 to 120° C., for 15 min to 24 hours with stirring. Alternatively, the reaction temperature may range from 130 to 180° C. when microwaves are used for 3 to 10 min.

In accordance with a further embodiment, the present invention provides an antifungal composition comprising the compound of Chemical Formula 1 or a pharmaceutical salt thereof as an active ingredient.

The pharmaceutical composition of the present invention can be formulated with the compound of the present invention or its pharmaceutically acceptable salt in combination with an inert pharmaceutical vehicle or carrier suitable for oral or non-oral or topical administration into various dosage forms using conventional methods.

As injections, which are representative of non-oral dosage forms, aqueous isotonic solutions or suspensions are preferred. Oral dosage forms may be exemplified by tablets, capsules, etc. In addition to the active ingredient, these dosage forms may include diluents (e.g., lactose, dextrose, sucrose, manitol, sorbitol, cellulose and/or glycine), lubricants (e.g., silica, talc, stearic acid or magnesium or calcium salts thereof, and/or polyethylene glycol) alone or in combination. Tablets may comprise binders such as magnesium aluminum silicate, starch paste, gelatin, tragacanth, methylcellulose, sodium carboxymethylcellulose and/or polyvinylpyrrolidone, and optionally disintegrants such as starch, agar, and alginic acid or sodium salts thereof, boiling mixtures, moisture absorbents, colorants, flavors, and/or sweeteners.

Depending on various factors including conditions of patients, such as severity of disease, sex, body weight, etc., administration route, doctor's prescriptions, and the like, the dosage of the active ingredient may vary. The therapeutically effective dose of the compound of the present invention can be readily determined by those who are skilled in the art. For the treatment of mammals infected with fungi, including human beings, for example, the compound of the present invention may be administered in an amount from 1 mg/kg/day to 500 mg/kg/day, and preferably in an amount from 1.0 mg/kg/day to 200 mg/kg/day orally or via injection routes A better understanding of the present invention may be obtained through the following examples which are set forth to illustrate, but are not to be construed as the limit of the present invention.

Example 1

2-(2,4-Difluorophenyl)-1-(2H-indazol-1-yl)-3-(1H-1,2,4-triazol-1-yl)propan-2-ol

To a suspension of Indazole (0.27 g, 2.32 mmol) in N,N-dimethylformamide (10 ml) was slowly added sodium hydride (0.093 g, 2.32 mmol) at 0° C., followed by stirring for 30 min and then for an additional 30 min at room temperature. Then, 1-((2-(2,4-difluorophenyl)oxiran-2-yl)methyl)-1H-1,2,4-triazole (0.50 g, 2.11 mmol) was added, followed by stirring for 2 hrs at 60° C. The reaction was quenched with the addition of water (1 ml) at 0° C. Following dilution with ethyl acetate (20 ml), the reaction mixture was washed with saturated ammonium chloride solution (20 ml) and then with brine (20 ml). The organic layer was dried over anhydrous magnesium sulfate and concentrated by evaporation in a vacuum condition. The product was purified by chromatography on silica gel to give the title compound (Yield 44%).

$^1$H-NMR (300 MHz, CDCl$_3$) δ 8.15 (s, 1H), 7.93 (s, 1H), 7.79 (s, 1H), 7.62 (d, 1H, J=8.1 Hz), 7.43 (m, 1H), 7.35 (d, 2H, J=6.2 Hz), 7.09 (m, 1H), 6.65 (m, 2H), 5.95 (br, 1H), 5.00 (d, 1H, J=14.5 Hz), 4.76 (d, 1H, J=14.3 Hz), 4.55 (d, 1H), 4.52 (d, 1H, J=14.5 Hz).

Example 2

2-(2,4-Difluorophenyl)-1-(1H-indazol-2-yl)-3-(1H-1,2,4-triazol-1-yl)propan-2-ol

Performing silica gel chromatography on crude product obtained in Example 1 yielded the title compound (Yield 41%).

$^1$H-NMR (300 MHz, CDCl$_3$) δ 8.17 (s, 1H), 7.81 (d, 2H, J=4.4 Hz), 7.61 (m, 2H), 7.25 (m, 1H), 7.08 (m, 1H), 6.78 (m, 1H), 6.65 (m, 1H), 6.09 (br, 1H), 4.78 (d, 1H, J=14.3 Hz), 4.64 (m, 2H), 4.53 (d, 1H, J=14.3 Hz).

Example 3

2-(2,4-Difluorophenyl)-1-(5-nitro-2H-indazol-1-yl)-3-(1H-1,2,4-triazol-1-yl)propan-2-ol 5-Nitroindazole (3.44 g, 21.08 mmol) was suspended in N,N-dimethylformamide (100 ml) and sodium hydride (0.93 g, 23.19 mmol) was slowly added to the suspension at 0° C., followed by stirring for 30 min and then for an additional 30 min at room temperature. The addition of 1-((2-(2,4-difluorophenyl)oxiran-2-yl)methyl)-1H-1,2,4-triazole (5 g, 21.08 mmol) was performed before stirring at 60° C. for 2 hours. The addition of water (1 ml) at 0° C. led to termination of the reaction. After being diluted with ethyl acetate (200 ml), the reaction mixture was washed with saturated ammonium chloride solution (200 ml) and then with brine (200 ml). The organic layer was dried over anhydrous magnesium sulfate and vacuum evaporated to concentrate it. The product was purified by chromatography on silica gel to give the title compound (Yield 47%). This compound was found to have a melting point from 63 to 64° C.

$^1$H-NMR (300 MHz, DMSO-d$_6$) δ 8.69 (d, 1H, J=2.1 Hz), 8.26 (s, 1H), 8.20 (s, 1H), 8.15 (dd, 1H, J=7.1 Hz, 2.2 Hz), 7.74 (m, 2H), 7.11 (m, 2H), 6.77 (m, 1H), 6.23 (s, 1H), 5.70 (br, —OH), 4.93 (d, 1H, J=5.8 Hz), 4.85 (d, 1H, J=14.5 Hz), 4.82 (d, 1H, J=14.7 Hz), 4.60 (d, 1H, J=14.5 Hz).

$^{13}$C-NMR (300 MHz, DMSO-d$_6$) δ 164.50, 163.75, 157.68, 150.76, 145.04, 142.56, 141.75, 136.28, 129.77, 123.67, 120.50, 122.62, 120.70, 118.69, 110.95, 103.86, 75.30, 55.01.

Example 4

2-(2,4-Difluorophenyl)-1-(5-nitro-1H-indazol-2-yl)-3-(1H-1,2,4-triazol-1-yl)propan-2-ol The silica gel chromatography of the crude product obtained in Example 3 gave the title compound (Yield 43%). m.p. 181-182° C.

$^1$H-NMR (300 MHz, DMSO-d$_6$) δ 8.75 (d, 1H, J=2.1 Hz), 8.57 (s, 1H), 8.24 (s, 1H), 7.82 (dd, 1H, J=7.3 Hz, 2.1 Hz), 7.70 (s, 1H), 7.56 (d, 1H, J=9.5 Hz), 7.10 (m, 2H), 6.72 (m, 1H), 6.44 (s, 1H), 6.17 (br, —OH), 4.94 (d, 1H, J=14.0 Hz), 4.80 (d, 1H, J=20.0 Hz), 4.76 (d, 1H, J=20.5 Hz), 4.51 (d, 1H, J=14.4 Hz).

$^{13}$C-NMR (300 MHz, DMSO-d$_6$) δ 164.50, 160.36, 157.57, 150.81, 148.52, 145.16, 141.91, 130.90, 129.73, 123.36, 120.52, 119.66, 117.96, 111.01, 103.97, 74.09, 59.43, 54.97.

Example 5

2-(2,4-Difluorophenyl)-1-(6-nitro-1H-indazol-2-yl)-3-(1H-1,2,4-triazol-1-yl)propan-2-ol The title compound was prepared in the same manner as in Example 3, with the exception that 6-Nitro-1H-indazole was used instead of 5-Nitroindazole.

$^1$H-NMR (300 MHz, CDCl$_3$) δ 8.44 (s, 1H), 8.43 (s, 2H), 7.97 (d, 1H, J=1.5 Hz), 7.79 (d, 1H, J=7.3 Hz), 7.76 (s, 1H), 7.43 (m, 1H), 6.73 (m, 2H), 5.58 (br, 1H), 4.96 (t, 2H), 4.74 (d, 1H, J=14.7 Hz), 4.47 (d, 1H, J=14.3 Hz).

Example 6

(5-Amino-2H-indazol-1-yl)-2-(2,4-difluorophenyl)-3-(1H-1,2,4-triazol-1-yl)propan-2-ol To a solution of 2-(2,4-difluorophenyl)-1-(5-nitro-1H-indazol-1-yl)-3-(1H-1,2,4-triazol-1-yl)propan-2-ol (3.57 g, 8.92 mmol) in methanol (50 ml) was added 5% palladium charcoal (Pd/C) (0.35 g) and hydrogen gas, followed by stirring for 12 hours. The reaction solution was filtered through celite. The filtrate was concentrated through vacuum evaporation to produce the title compound. (Yield 87%).

$^1$H-NMR (300 MHz, CDCl$_3$) δ 8.15 (s, 1H), 7.81 (s, 1H), 7.73 (s, 1H), 7.42 (m, 1H), 7.18 (m, 1H), 6.83 (m, 2H), 6.67 (m, 2H), 5.90 (br, —OH), 4.92 (d, 1H, J=14.5 Hz), 4.73 (d, 1H, J=14.3 Hz), 4.53 (d, 1H, J=14.3 Hz), 4.45 (d, 1H, J=14.5 Hz).

Example 7

(5-Amino-1H-indazol-2-yl)-2-(2,4-difluorophenyl)-3-(1H-1,2,4-triazol-1-yl)propan-2-ol With the exception that 2-(2,4-Difluorophenyl)-1-(5-nitro-1H-indazol-2-yl)-3-(1H-1,2,4-triazol-1-yl)propan-2-ol was used, the same procedure as in Example 6 was performed to produce the title compound.

$^1$H-NMR (300 MHz, CDCl$_3$) δ 8.35 (s, 1H), 7.77 (s, 1H), 7.72 (s, 1H), 7.27 (m, 2H), 6.92 (m, 2H), 6.84 (m, 1H), 6.69 (m, 1H), 4.95 (d, 2H), 4.63 (m, 2H).

Example 8

(6-Amino-1H-indazol-2-yl)-2-(2,4-difluorophenyl)-3-(1H-1,2,4-triazol-1-yl)propan-2-ol With the exception that 2-(2,4-Difluorophenyl)-1-(5-nitro-1H-indazol-2-yl)-3-(1H-1,2,4-triazol-1-yl)propan-2-ol, the same procedure as in Example 6 was performed.

$^1$H-NMR (300 MHz, CDCl$_3$) δ 8.07 (s, 2H), 6.67 (s, 2H), 7.23 (m, 2H), 6.65 (m, 2H), 6.43 (m, 1H), 6.18 (br, 1H), 4.67 (d, 2H, J=14.3 Hz), 4.39 (m, 2H).

Example 9

1-(5-(Benzylamino)-2H-indazol-1-yl)-2-(2,4-difluorophenyl)-3-(1H-1,2,4-triazol-1-yl)propan-2-ol To a solution of (5-Amino-2H-indazol-1-yl)-2-(2,4-difluorophenyl)-3-(1H-1,2,4-triazol-1-yl)propan-2-ol (0.065 g, 0.17 mmol) in acetonitrile (1 ml) was slowly added N,N-Diisopropylethylamine (0.033 ml, 0.19 mmol) at 0° C. and the solution was stirred for 30 min in the same condition. Benzylchloride (0.024 g, 0.19 mmol) was added to the solution, which was then stirred at room temperature for 2 hours and concentrated using vacuum evaporation. The crude product was purified by chromatography on silica gel to give the title compound. (Yield 84%).

$^1$H-NMR (300 MHz, CDCl$_3$) δ 8.15 (s, 1H), 7.86 (s, 1H), 7.81 (s, 1H), 7.35 (m, 8H), 7.03 (s, 1H), 7.37 (s, 1H), 7.35 (s, 1H), 5.95 (br, —OH), 4.96 (d, 1H, J=14.4 Hz), 4.78 (d, 1H, J=14.3 Hz), 4.66 (s, 1H), 4.57 (d, 1H, J=14.4 Hz), 4.51 (d, 1H, J=14.6 Hz), 4.36 (s, 1H).

Examples 10 to 39

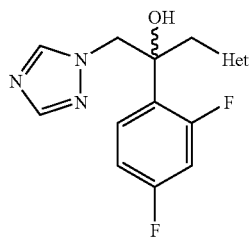

Procedures similar to that of Example 9 were performed to synthesize the compounds represented by the chemical formula above, wherein the Het moiety is as listed in Table 1, below.

TABLE 1

| Ex. | Het | $^1$H-NMR (300 MHz, CDCl$_3$) δ |
|---|---|---|
| 10 | indazol-2-yl linked to 5-(2-chlorobenzylamino) | 8.18 (s, 1H), 7.82 (s, 1H), 7.73 (s, 1H), 7.44 (m, 3H), 7.27 (m, 4H), 6.87 (d, 1 H, J = 7.8 Hz), 6.69 (m, 2H), 5.97 (br, —OH), 4.89 (d, 1 H, J = 14.4 Hz), 4.79 (s, 1H), 4.75 (s, 2H), 4.50 (m, 2H). |
| 11 | indazol-1-yl linked to 5-(2-chlorobenzylamino) | 8.14 (s, 1H), 7.80 (s, 1H), 7.72 (s, 1H), 7.40 (m, 2H), 7.20 (m, 4H), 6.82 (d, 1 H, J = 12.0 Hz), 6.64 (m, 3H), 5.98 (br, —OH), 4.89 (d, 1 H, J = 11.1 Hz), 4.71 (s, 1H), 4.53 (s, 1H), 4.47 (s, 1H), 4.42 (s, 2H). |
| 12 | indazol-2-yl linked to 5-(2-trifluoromethylbenzylamino) | 8.17 (s, 1H), 7.81 (s, 1H), 7.73 (s, 1H), 7.71 (d, 1H), 7.68 (d, 1H), 7.43 (m, 3H), 7.23 (d, 1H), 6.88 (dd, 1H), 6.68 (s, 1H), 6.66 (s, 1H), 6.58 (s, 1H), 5.96 (br, —OH), 4.89 (d, 1H), 4.68 (s, 1H), 4.58 (s, 1H), 4.47 (s, 2H), 4.60 (m, 2H). |
| 13 | indazol-1-yl linked to 5-(2-trifluoromethylbenzylamino) | 8.13 (s, 1H), 7.79 (s, 1H), 7.69 (s, 1H), 7.66 (d, 1 H, J = 19.2 Hz), 7.63 (d, 1 H, J = 16.8 Hz), 7.39 (m, 3H), 7.20 (d, 1 H, J = 9.0 Hz), 6.83 (dd, 1 H, J = 6.8 Hz, 2.1 Hz), 6.68 (s, 1H), 6.66 (s, 1H), 6.58 (s, 1H), 5.97 (br, —OH), 4.89 (d, 1 H, J = 14.5 Hz), 4.72 (d, 1 H, J = 14.3 Hz), 4.53 (s, 2H), 4.47 (s, 1H), 4.43 (s, 1H). |
| 14 | indazol-1-yl linked to 5-(2-biphenylmethylamino) | 8.14 (s, 1H),, 7.81 (s, 1H), 7.68 (s, 1H), 7.47~7.25 (m, 11 H), 7.12 (d, 1H), 6.72 (m, 2H), 6.55 (s, 1H), 5.99 (br, 1H), 4.86 (d, 1H), 4.73 (d, 1H), 4.52 (s, 2H), 4.78 (m, 2H) |

TABLE 1-continued

| Ex. | Het | ¹H-NMR (300 MHz, CDCl₃) δ |
|---|---|---|
| 15 | indazol-2-yl-NH-CH₂-C₆H₄-F (4-F) | 8.13 (s, 1H), 7.81 (m, 1H), 7.72 (m, 1H), 7.38 (m, 3H), 7.22 (m, 2H), 7.00 (m, 3H), 6.68 (m, 2H), 5.46 (br, —OH), 4.88 (m, 1H), 4.74 (m, 1H), 4.48 (m, 3H), 4.31 (s, 1H). |
| 16 | indazol-2-yl-NH-CH₂-C₆H₄-Cl (4-Cl) | 8.34 (m, 1H), 7.90 (m, 2H), 7.38 (m, 3H), 7.19 (m, 4H), 7.10 (d, 1 H, J = 7.9 Hz), 6.67 (m, 2H), 5.90 (br, —OH), 4.85 (m, 2H), 4.56 (m, 4H). |
| 17 | indazol-1-yl-NH-CH₂-C₆H₄-Cl (4-Cl) | 8.14 (s, 1H), 7.80 (s, 1H), 7.72 (s, 1H), 7.42 (dd, 1 H, J = 6.6 Hz, 6.6 Hz), 7.29 (s, 4H), 7.19 (d, 1 H, J = 9.0 Hz), 6.82 (d, 1 H, J = 9.0 Hz), 6.67 (m, 3H), 5.96 (br, —OH), 4.90 (d, 1 H, J = 14.5 Hz), 4.72 (d, 1 H, J = 14.3 Hz), 4.51 (d, 1 H, J = 14.3 Hz), 4.45 (d, 1 H, J = 14.5 Hz), 4.28 (s, 2H). |
| 18 | indazol-2-yl-NH-CH₂-C₆H₄-Br (4-Br) | 8.13 (s, 1H), 7.79 (s, 1H), 7.71 (s, 1H), 7.43 (m, 3H), 7.20 (m, 3H), 6.82 (dd, 1 H, J = 6.9 Hz, 2.0 Hz), 6.67 (m, 3H), 5.96 (br, —OH), 4.90 (d, 1 H, J = 14.5 Hz), 4.72 (d, 1 H, J = 14.3 Hz), 4.51 (d, 1 H, J = 14.5 Hz), 4.45 (d, 1 H, J = 14.4 Hz), 4.26 (s, 2H). |
| 19 | indazol-2-yl-NH-CH₂-C₆H₄-CF₃ (4-CF₃) | 8.13 (s, 1H), 7.80 (s, m), 7.71 (s, 1H), 7.62 (s, 1H), 7.59 (s, 1H), 7.49 (s, 1H), 7.47 (s, 1H), 7.42 (m, 1H), 7.22 (d, m, J = 8.8 Hz), 6.85 (dd, 1 H, J = 6.9 Hz, 2.1 Hz), 6.67 (m, 3H), 5.91 (br, —OH), 4.90 (d, 1 H, J = 14.5 Hz), 4.73 (d, 1 H, J = 14.3 Hz), 4.51 (d, 1 H, J = 14.7 Hz), 4.46 (d, 1 H, J = 14.8 Hz), 4.41 (s, 2H). |
| 20 | indazol-2-yl-NH-CH₂-C₆H₄-CN (4-CN) | 8.16 (s, 1H), 8.14 (s, 1H), 8.12 (s, 1H), 7.77 (s, 1H), 7.68 (s, 1H), 7.53 (s, 1H), 7.50 (s, 1H), 7.40 (dd, 1 H, J = 6.6 Hz, 2.1 Hz), 7.20 (d, 1 H, J = 9.0 Hz), 6.82 (dd, 1 H, J = 6.9 Hz, 2.1 Hz), 6.66 (m, 2H), 6.52 (d, 1 H, J = 1.9 Hz), 5.93 (br, —OH), 4.88 (d, 1 H, J = 14.5 Hz), 4.72 (d, 1 H, J = 14.3 Hz), 4.50 (d, 1 H, J = 14.5 Hz), 4.45 (d, 1 H, J = 14.6 Hz), 4.44 (s, 2H). |
| 21 | indazol-2-yl-NH-CH₂-C₆H₄-NO₂ (4-NO₂) | 8.13 (s, 1H), 7.80 (m, 2H), 7.38 (m, 3H), 7.24 (m, 2H), 7.14 (m, 1H), 6.97 (s, 1H), 6.95 (s, 1H), 6.68 (m, 2H), 5.87 (br, —OH), 4.91 (d, 1 H, J = 14.6 Hz), 4.74 (d, 1 H, J = 14.2 Hz), 4.50 (m, 3H), 4.33 (s, 1H). |
| 22 | indazol-2-yl-NH-CH₂-C₆H₄-OCF₃ (4-OCF₃) | 8.14 (s, 1H), 7.81 (s, 1H), 7.75 (s, 1H), 7.55 (m, 4H), 7.41 (m, 5H), 7.35 (m, 1H), 7.20 (m, 1H), 6.89 (m, 2H), 6.67 (m, 2H), 5.94 (br, —OH), 4.90 (d, 1 H, J = 14.1 Hz), 4.73 (d, 1 H, J = 14.2 Hz), 4.51 (d, 1 H, J = 14.2 Hz), 4.45 (d, 1 H, J = 14.5 Hz), 4.35 (s, 2H). |

TABLE 1-continued

| Ex. | Het | $^1$H-NMR (300 MHz, CDCl$_3$) δ |
|---|---|---|
| 23 | 2H-indazol-5-yl linked to NH-CH2-(2,4-difluorophenyl) | 8.13 (s, 1H), 7.79 (s, 1H), 7.72 (s, 1H), 7.40 (m, 1H), 7.24 (d, 1H), 6.99 (m, 1H), 6.76 (m, 4H), 6.67 (m, 2H), 5.89 (br, 1H), 4.87 (d, 1H), 4.74 (d, 1H), 4.55 (s, 2H), 4.50 (m, 2H) |
| 24 | 1H-indazol-5-yl linked to NH-CH2-(2,4-difluorophenyl) | 8.13 (s, 1H), 7.79 (s, 1H), 7.72 (s, 1H), 7.40 (m, 1H), 7.24 (d, 1H), 6.99 (m, 1H), 6.76 (m, 4H), 6.67 (m, 2H), 5.89 (br, 1H), 4.87 (d, 1H), 4.74 (d, 1H), 4.55 (s, 2H), 4.50 (m, 2H) |
| 25 | 2H-indazol-5-yl linked to NH-CH2-(2,4-dichlorophenyl) | 9.05 (s, 1H), 8.88 (d, 1 H, J = 2.1 Hz), 8.59 (d, 1 H, J = 8.7 Hz), 8.51 (m, 1H), 8.13 (s, 1H), 7.99 (s, 1H), 7.81 (s, 1H), 7.61 (s, 1H), 7.43 (m, 2H), 6.70 (m, 2H), 5.80 (br, —OH), 5.45 (s, 1H) 5.00 (d, 1 H, J = 14.6 Hz), 4.80 (d, 1 H, J = 14.3 Hz), 4.57 (m, 3H). |
| 26 | 2H-indazol-5-yl linked to NH-CH2-(2,4-bis(trifluoromethyl)phenyl) | 8.13 (s, 1H), 8.06 (s, 1H), 7.79 (s, 1H), 7.68 (s, 1H), 7.61 (d, 1 H, J = 8.5 Hz), 7.46 (m, 2H), 7.22 (m, 1H), 6.82 (dd, 1 H, J = 6.8 Hz, 2.1 Hz), 6.67 (m, 2H), 6.48 (s, 1H), 5.91 (br, —OH), 4.89 (d, 1 H, J = 14.5 Hz), 4.73 (d, 1 H, J = 14.4 Hz), 4.68 (s, 2H), 4.47 (t, 2H, J = 14.6 Hz). |
| 27 | 2H-indazol-5-yl linked to NH-CH2-(2,6-difluorophenyl) | 8.13 (s, 1H), 7.79 (s, 1H), 7.76 (s, 1H), 7.41 (d, 1H, J = 6.6 Hz), 7.18 (m, 3H), 6.97 (m, 1H), 6.85 (m, 2H), 6.66 (m, 2H), 5.98 (br, —OH), 4.89 (d, 1 H, J = 14.5 Hz), 4.72 (d, 1 H, J = 14.2 Hz), 4.47 (m, 4H). |
| 28 | 2H-indazol-5-yl linked to NH-CH2-(2,6-dichlorophenyl) | 8.13 (s, 1H), 7.80 (s, 1H), 7.72 (s, 1H), 7.42 (m, 3H), 7.20 (d, 2 H, J = 8.5 Hz), 6.82 (dd, 1 H, J = 10.2 Hz, 1.8 Hz), 6.67 (m, 2H), 6.60 (d, 1 H, J =1.8 8Hz), 5.95 (br, —OH), 4.90 (d, 1 H, J = 15.5 Hz), 4.73 (d, 1 H, J = 15.5 Hz), 4.48 (t, 2H, J = 15.5 Hz), 4.28 (s, 2H). |
| 29 | 2H-indazol-5-yl linked to NH-CH2-(2-chloro-6-fluorophenyl) | 8.13 (s, 1H), 7.81 (s, 1H), 7.77 (s, 1H), 7.40 (m, 1H), 7.19 (m, 2H), 7.03 (m, 4H), 6.67 (m, 2H), 5.89 (br, —OH), 4.91 (d, 1 H, J = 14.6 Hz), 4.73 (d, 1 H, J = 14.2 Hz), 4.48 (m, 2H), 4.24 (m, 2H), 2.23 (m, 6 H). |
| 30 | 1H-indazol-6-yl linked to NH-CH2-(2-chlorophenyl) | 8.15 (s, 1H), 7.80 (s, 1H), 7.73 (s, 1H), 7.41 (m, 7 H), 6.51 (m, 2H), 6.24 (s, 1H), 6.12 (br, 1H), 4.78 (m, 2H), 4.62 (m, 1H), 4.52 (s, 2H), 4.35 (m, 1H) |

TABLE 1-continued
| Ex. | Het | ¹H-NMR (300 MHz, CDCl₃) δ |
|---|---|---|
| 31 | 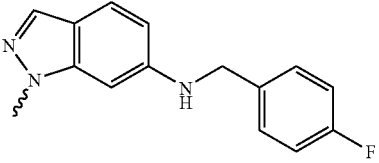 | 8.12 (s, 1H), 7.82 (s, 1H), 7.72 (s, 1H), 7.42 (m, 6 H), 6.55 (m, 3H), 6.31 (s, 1H), 4.81 (d, 1H), 4.67 (d, 1H), 4.52 (d, 1H), 4.41 (s, 2H), 4.32 (d, 1H) |
| 32 | 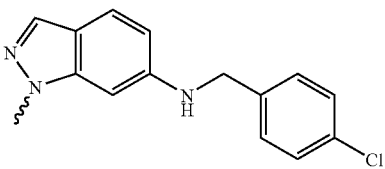 | 8.14 (s, 1H), 7.80 (s, 1H), 7.72 (s, 1H), 7.37 (m, 6 H), 6.49 (m, 3H), 6.21 (s, 1H), 4.78 (d, 1 H, J = 12.5 Hz), 4.63 (d, 1H, J = 14.3 Hz), 4.48 (d, 1 H, J = 84.3 Hz), 4.34 (s, 2H), 4.29 (d, 1 H, J = 12.5 Hz) |
| 33 | 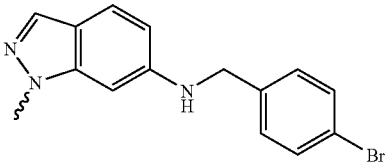 | 8.15 (s, 1H), 7.75 (s, 2H), 7.52-7.27 (m, 7 H), 7.11 (d, 2 H, J = 8.4 Hz), 6.68-6.48 (m, 3H), 6.06 (br, 1H), 4.81-4.66 (m, 4H), 4.33 (m, 2H) |
| 34 | 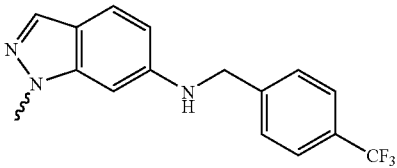 | 8.15 (s, 1H), 7.81-7.36 (m, 9 H), 6.66 (m, 2H), 6.52 (m, 1H), 4.78 (d, 1 H, J = 14.2 Hz), 4.63 (d, 1H), 4.47 (m, 3H), 4.37 (m, 1H) |
| 35 | 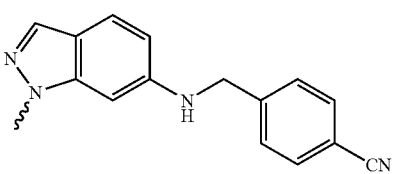 | 8.13 (s, 1H), 7.80 (s, 1H), 7.75 (s, 1H), 7.64 (d, 4 H, J = 8.2 Hz), 7.37 (m, 6 H), 6.57 (m, 3H), 6.36 (s, 1H), 5.92 (br, 1H), 4.68 (m, 6H), 4.44 (d, 1 H, J = 14.1 Hz), 4.28 (d, 1 H, J = 14.5 Hz) |
| 36 | 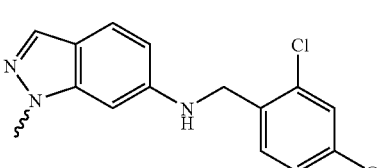 | 8.19 (s, 1H), 7.82 (s, 1H), 7.75 (s, 1H), 7.48 (d, 1 H, J = 2.1 Hz), 7.43-7.21 (m, 4H), 6.54 (m, 2H), 6.21 (s, 1H), 4.79 (d, 1 H, J = 14.5 Hz), 4.67 (d, 1 H, J = 14.3 Hz), 4.53-4.33 (m, 4H) |
| 37 | 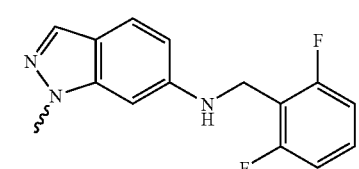 | 8.14 (s, 1H), 7.79 (s, 1H), 7.73 (s, 1H) 7.29 (m, 2H), 7.24 (m, 1H), 6.90 ( m, 3 H0, 6.66 (m, 2H), 6.49 (s, 1H), 6.11 (br, 1H), 4.77 (m, 3H), 4.47 (m, 3H) |

TABLE 1-continued

| Ex. | Het | $^1$H-NMR (300 MHz, CDCl$_3$) δ |
|---|---|---|
| 38 | | 8.17 (s, 1H), 7.80 (s, 1H), 7.75 (s, 1H), 7.45 (m, 1H), 7.36 (m, 3H), 7.24(m, 2H), 6.68 (m, 2H), 6.52 (d, 1 H, J = 5.6 Hz), 6.15 (br, 1H), 4.78 (m, 2H), 4.62 (s, 2H), 4.50 (m, 2H) |
| 39 | | 8.15 (s, 1H), 7.79 (s, 1H), 7.74 (s, 1H), 7.43 (m, 1H), 7.34 (d, 1 H, J = 8.6 Hz), 7.23 (m, 2H), 7.05 (m, 1H), 6.67 (t, 2H), 6.49 (m, 2H), 6.17 (br, 1H), 4.83 (d, 1 H, J = 14.5 Hz), 4.75 (d, 1 H, J = 14.3 Hz), 4.53 (s, 2H), 4.48 (d, 2H, J = 14.5 Hz) |

Example 40

1-(2-(2,4-Difluorophenyl)-2-hydroxy-3-(1H-1,2,4-triazol-1-yl)-propyl)-3-methyl-1H-indazol-4-ol The title compound was synthesized in the following three steps with reference to the literature (*J. Med. Chem.*, 2000, 43(14), 2664-2674).

Step 1) Synthesis of 3-methyl-1H-indazol-4-ol

To a solution of 2,6-dihydroxy acetophenone (0.50 g, 3.31 mmol) in ethylene glycol (7 ml) was slowly added a solution of hydrazine hydrate (3.3 g, 6.59 mmol) in ethylene glycol (2 ml). The reaction mixture was stirred for 20 min at room temperature and for an additional 2 hours at 160° C. After cooling to room temperature and dilution with distilled water (20 ml), the acetic acid (0.25 ml) was added to adjust the pH of the solution to 6. The resulting mixture was extracted four times with ethyl acetate, washed with a 5% sodium sulfite solution, dried over magnesium sulfate, filtered, and concentrated using vacuum evaporation. The crude product was purified by chromatography on silica gel to give 0.37 g of 3-Methyl-1H-indazol-4-ol (Yield 68%).

Step 2) Synthesis of 4-(tert-butyl-dimethyl-silanyloxy)-3-methyl-1H-indazole To a solution of 3-methyl-1H-indazol-4-ol (0.13 g, 0.90 mmol) in N,N-dimethylformamide (10 ml) was added imidazole (0.31 g, 4.52 mmol) and tert-butyldimethylchlorosilane (0.16 g, 1.04 mmol) at 0° C. Following stirring at room temperature for 12 hours and the addition of distilled water (10 ml), the reaction mixture was extracted three times with ethyl acetate, washed with distilled water and brine, dried over magnesium sulfate, filtered, and concentrated using vacuum evaporation. The crude product was purified by chromatography on silica gel to give 0.21 g of 4-(tert-butyl-dimethyl-silanyloxy)-3-methyl-1H-indazole (Yield 89%).

Step 3) Synthesis of 1-(2-(2,4-difluorophenyl)-2-hydroxy-3-(1H-1,2,4-triazol-1-yl)-propyl)-3-methyl-1H-indazol-4-ol To a suspension of 4-(tert-butyl-dimethyl-silanyloxy)-3-methyl-1H-indazole (0.13 g, 0.49 mmol) in N,N'-dimethylformamide (5 ml) was slowly added sodium hydride (0.18 g, 0.44 mmol) at 0° C., followed by stirring for 30 min at 0° C. and then for an additional 30 min at room temperature. 1-((2-(2,4-difluorophenyl)oxyrane-2-yl)methyl)-1H-1,2,4-triazole (0.99 g, 0.85 mmol) was added and stirring was conducted for 2 hours at 60° C. before the reaction was terminated using water (1 ml) at 0° C. The reaction solution was diluted with ethyl acetate (5 ml) and washed with saturated ammonium chloride solution (5 ml) and then with brine (5 ml). The organic layer was dried over anhydrous magnesium sulfate, and concentrated using vacuum evaporation. The crude product was purified by chromatography on silica gel to give the title compound (Yield 45%).
$^1$H-NMR (300 MHz, CDCl$_3$) δ 8.72 (br, 1H), 8.20 (s, 1H), 7.81 (s, 1H), 7.41 (m, 1H), 7.02 (m, 1H), 6.66 (m, 3H), 6.27 (d, 1H, J=7.5 Hz), 6.21 (br, 1H), 4.74 (q, 2H), 4.43 (q, 2H), 2.64 (s, 3H).

Examples 41 to 43

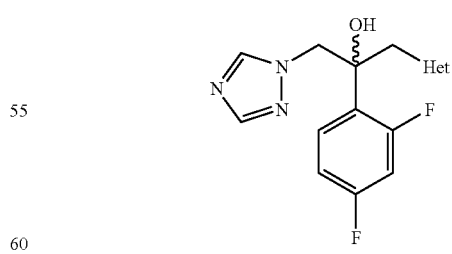

With the exception that 1-(2-(2,4-difluorophenyl)-2-hydroxy-3-(1H-1,2,4-triazol-1-yl)-propyl)-3-methyl-1H-indazol-4-ol, prepared in Example 40, was used, the same procedure as that of Example 9 was conducted to synthesize the compounds represented by the chemical formula above, the Het moiety thereof being as listed in Table 2, below.

TABLE 2

| Ex. | Het | $^1$H-NMR (300 MHz, CDCl$_3$) δ |
|---|---|---|
| 41 | (1H-indazole with 3-methyl, 4-O-CH$_2$-C$_6$H$_4$-F) | 8.12 (s, 1H), 7.81 (s, 1H), 7.44 (m, 3H), 7.03 (m, 2H), 6.81~6.66 (m, 4H), 6.29 (d, 1 H, J = 7.5 Hz), 5.09 (s, 2H), 4.80 (q, 2H), 4.42 (q, 2H), 2.64 (s, 3H). |
| 42 | (1H-indazole with 3-methyl, 4-O-CH$_2$-C$_6$H$_4$-Cl) | 8.20 (s, 1H), 7.81 (s, 1H), 7.43 (m, 3H), 7.11 (m, 2H), 6.87~6.66 (m, 4H), 6.28 (d, 1 H, J = 7.5 Hz), 5.10 (s, 2H), 4.81 (q, 2H), 4.43 (q, 2H), 2.64 (s, 3H). |
| 43 | (1H-indazole with 3-methyl, 4-O-CH$_2$-C$_6$H$_4$-CN) | 8.11 (s, 1H), 7.80 (s, 1H), 7.40 (m, 3H), 7.10 (m, 2H), 6.87~6.65 (m, 4H), 6.28 (d, 1 H, J = 7.5 Hz), 5.20 (s, 2H), 4.84 (q, 2H), 4.41 (q, 2H), 2.63 (s, 3H). |

Example 44

(E)-3-(4-Bromophenyl)-N-(1-(2-(2,4-difluorophenyl)-2-hydroxy-3-(1H-1,2,4-triazol-1-yl)propyl)-1H-indazol-5-yl)acrylamide To a solution, of (E)-3-(4-bromophenyl)acrylic acid (0.034 g, 0.15 mmol) in tetrahydrofuran (1 ml) were added 1-hydroxybenzotriazole (0.023 g, 0.17 mmol) and 1-[3-(dimethylamino)propyl]-3-ethylcarbodiimide hydrochloride (0.032 g, 0.17 mmol). Then triethylamine (0.045 ml, 0.32 mmol) was slowly added at 0° C., followed by stirring the reaction mixture for 30 min. After the addition of (5-Amino-1H-indazol-1-yl)-2-(2,4-difluorophenyl)-3-(1H-1,2,4-triazol-1-yl)propan-2-ol (0.057 g, 0.15 mmol) and 4-N,N-dimethylaminopyridine (0.004 g, 0.03 mmol), stirring at room temperature for 2 hours and concentrated by evaporation in a vacuum condition. The crude product was purified by chromatography on silica gel to give the title compound.

$^1$H-NMR (300 MHz, CDCl$_3$) δ 8.15 (s, 1H), 8.08 (s, 1H), 7.83 (s, 1H), 7.82 (s, 1H), 7.64 (d, 1H, J=15.5 Hz), 7.44 (d, 1H, J=8.4 Hz), 7.38 (m, 3H), 7.30 (m, 1H), 6.68 (m, 2H), 6.55 (d, 1H, J=15.5 Hz), 5.84 (br, 1H), 4.92 (d, 1H, J=14.6 Hz), 4.76 (d, 1H, J=14.4 Hz), 4.52 (m, 2H).

Example 45

(2S)-2-Amino-N-(1-(2-(2,4-difluorophenyl)-2-hydroxy-3-(1H-1,2,4-triazol-1-yl)propyl)-1H-indazol-5-yl)-3-phenylpropaneamide The title compound was prepared in a manner similar to that of Example 44.

$^1$H-NMR (300 MHz, CDCl$_3$) δ 8.23 (s, 1H), 8.15 (s, 2H), 8.11 (s, 1H), 7.72 (d, 1H), 7.58 (d, 1H), 7.24-7.15 (m, 6H), 6.63 (m, 2H), 4.30 (d, 2H), 4.05 (d, 2H), 3.95 (t, 1H), 3.28 (d, 2H).

Example 46

2-(1-(2-(2,4-Difluorophenyl)-2-hydroxy-3-(1H-1,2,4-triazol-1-yl)propyl)-1H-indazol-5-ylamino)-N-(2,6-dimethylphenyl)acetamide To a solution of (5-amino-1H-indazol-1-yl)-2-(2,4-difluorophenyl)-3-(1H-1,2,4-triazol-1-yl)propan-2-ol (0.1 g, 0.27 mmol) in N,N-dimethylformaide (1 ml) was slowly added potassium carbonate (0.037 g, 0.27 mmol) at 0° C. and followed by stirring for 30 min. The addition of 2-bromo-N-(2,6-dimethylphenyl)acetamide (0.065 g, 0.27 mmol) to the solution was followed by stirring at room temperature for hours and concentrated by evaporation in a vacuum condition. The crude product was purified by chromatography on silica gel to give the title compound (Yield 50%).

$^1$H-NMR (300 MHz, CDCl$_3$) δ 8.21 (m, 2H), 7.83 (s, 1H), 7.78 (s, 1H), 7.43 (m, 1H), 7.04 (m, 4H), 6.93 (m, 1H), 6.69 (m, 2H), 4.95 (d, 1H, J=14.5 Hz), 4.75 (d, 1H, J=14.3 Hz), 4.52 (m, 2H), 4.03 (s, 2H), 2.08 (s, 6H).

Example 47

2-(3-(1-(2-(2,4-Difluorophenyl)-2-hydroxy-3-(1H-1,2,4-triazol-1-yl)propyl)-1H-indazol-5-ylamino)-2-oxopropyl)-4,5,6,7-tetrahydrobenzo[b]thiophene-3-carbonitrile Using a procedure similar to that of Example 46, the title compound was obtained.

$^1$H-NMR (300 MHz, CDCl$_3$) δ 8.17 (s, 1H), 7.81 (m, 2H), 7.43 (m, 1H), 7.28 (m, 2H), 6.92 (m, 1H), 6.70 (m, 2H), 4.90

(d, 1H, J=14.5 Hz), 4.76 (d, 1H, J=14.3 Hz), 4.50 (m, 4H), 4.22 (s, 2H), 4.03 (s, 2H), 2.57 (m, 4H), 1.86 (m, 4H).

Example 48

2-(1-(2-(2,4-Difluorophenyl)-2-hydroxy-3-(1H-1,2,4-triazol-1-yl)propyl)-1H-indazol-5-ylamino)-1-(4-phenylpiperazin-1-yl)ethanone Using a procedure similar to that of Example 46, the title compound was obtained.

$^1$H-NMR (300 MHz, CDCl$_3$) δ 8.14 (s, 1H), 7.79 (s, 1H), 7.73 (s, 1H), 7.41 (m, 1H), 7.30 (m, 2H), 7.20 (d, 1H), 6.93 (d, 3H), 6.88 (dd, 1H), 6.66 (m, 2H), 6.59 (d, 1H), 5.98 (br, 1H), 4.90 (d, 1H, J=14.5 Hz), 4.72 (d, 1H, J=14.3 Hz), 4.48 (m, 2H), 3.91 (s, 2H), 3.74 (m, 8H).

Example 49

Methyl 2-(1-(2-(2,4-difluorophenyl)-2-hydroxy-3-(1H-1,2,4-triazol-1-yl)propyl)-1H-indazol-5-ylamino)acetate Using a procedure similar to that of Example 46, the title compound was obtained.

$^1$H-NMR (300 MHz, CDCl$_3$) δ 8.22 (s, 1H), 7.82 (s, 1H), 7.77 (s, 1H), 7.42 (m, 1H), 7.26 (s, 2H), 6.92 (d, 1H), 6.70 (m, 2H), 4.91 (d, 1H, J=14.3 Hz), 4.75 (d, 1H, J=14.3 Hz), 4.51 (m, 2H), 3.93 (s, 2H), 3.78 (s, 3H).

Example 50

(2R,3R)-2-(2,4-Difluorophenyl)-3-(2H-indazol-1-yl)-1-(1H-1,2,4-triazol-1-yl)butan-2-ol To a suspension of indazole (0.059 g, 0.5 mmol), 1-(((2R,3S)-2-(2,4-difluorophenyl)-3-methyloxiran-2-yl)methyl)-1H-1,2,4-triazole (0.105 g, 0.416 mmol) in N,N'-dimethylformamide (2.5 ml) was added anhydrous potassium carbonate (0.069 g, 0.5 mmol), followed by radiating microwaves thereon with stirring at 180° C. for 5 min. Thereafter, the addition of water (0.5 ml) at 0° C. terminated the reaction. The reaction solution was diluted with ethyl acetate (10 ml) and washed with saturated ammonium chloride solution (10 ml) and then with brine (10 ml). The organic layer was dried over anhydrous magnesium sulfate and concentrated in a vacuum. The crude product was purified by chromatography on silica gel to give the title compound (Yield 44%).

$^1$H-NMR (300 MHz, CDCl$_3$) δ 8.15 (s, 1H), 7.88 (s, 1H), 7.8 (d, 1H), 7.69 (d, 1H), 7.59 (s, 1H), 7.55 (m, 2H), 7.22 (m, 1H), 6.81 (m, 2H), 6.05 (br, 1H), 5.43 (q, 1H), 4.75 (d, 1H), 3.55 (d, 1H), 1.37 (d, 3H).

Examples 51 to 65

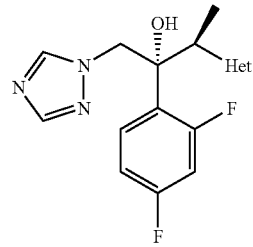

Compounds of the chemical formula above wherein Het is as listed in Table 3, below, were synthesized in a procedure similar to that of Example 50.

TABLE 3

| Ex. | Het | $^1$H-NMR (300 MHz, CDCl$_3$) δ |
|---|---|---|
| 51 | indazol-1-yl | 8.24 (s, 1H), 7.83 (s, 1H), 7.59 (d, 1H), 7.48 (m, 2H), 7.35 (m, 1H), 7.12 (m, 1H), 6.83 (m, 2H), 6.38 (br, 1H), 5.33 (q, 1H), 4.82 (d, 1H), 3.48 (d, 1H), 1.44 (d, 3H) |
| 52 | 3-chloro-indazol-1-yl | 7.93 (s, 1H), 7.73 (d, 1H), 7.55 (m, 4H), 7.29 (m, 1H), 6.8 (m, 2H), 5.50 (br, 1H), 5.35 (q, 1H), 4.87 (d, 1H), 3.75 (d, 1H), 1.42 (d, 3H) |
| 53 | 7-CF$_3$-3-F-indazol-1-yl | 8.15 (s, 1H), 8.11 (s, 1H), 7.82 (m, 1H), 7.53 (m, 1H), 7.15 (m, 2H), 6.65 (m, 2H), 5.03 (q, 1H), 4.73 (d, 1H), 3.32 (d, 1H), 1.51 (d, 3H) |

TABLE 3-continued

| Ex. | Het | ¹H-NMR (300 MHz, CDCl₃) δ |
|---|---|---|
| 54 | indazole with CF₃ at 7-position and F at 3-position | 8.98 (s, 1H), 8.11 (s, 1H), 7.53 (m, 1H), 7.31 (m, 3H), 6.60 (m, 2H), 5.52 (br, 1H), 5.07 (q, 1H), 4.71 (d, 1H), 3.30 (d, 1H), 1.47 (d, 3H) |
| 55 | 5-iodo-1H-indazole | 8.33 (s, 1H), 8.01 (s, 1H), 7.78 (m, 1H), 7.66 (s, 1H), 7.58 (m, 2H), 7.17 (m, 1H), 6.90 (m, 2H), 5.21 (q, 1H), 4.75 (d, 1H), 3.42 (d, 1H), 1.46 (d, 3H) |
| 56 | 5-fluoro-2H-indazole | 8.23 (s, 1H), 7.90 (s, 1H), 7.73 (m, 1H), 7.66 (s, 1H), 7.55 (m, 2H), 7.17 (m, 1H), 6.84 (m, 2H), 5.35 (q, 1H), 4.85 (d, 1H), 3.52 (d, 1H), 1.46 (d, 3H) |
| 57 | 5-fluoro-1H-indazole | 8.12 (s, 1H), 7.99 (s, 1H), 7.61 (s, 1H), 7.52 (m, 2H), 7.41 (dd, 1H), 7.29 (m, 1H), 6.80 (m, 2H), 5.9 (br, 1H), 5.39 (q, 1H), 4.79 (d, 1H), 3.63 (d, 1H), 1.39 (d, 3H) |
| 58 | 5-chloro-2H-indazole | 8.11 (s, 1H), 7.91 (s, 1H), 7.81 (d, 1H), 7.41 (m, 4H), 6.78 (m, 2H), 5.21 (q, 1H), 4.71 (d, 1H), 3.57 (d, 1H), 1.49 (d, 3H) |
| 59 | 5-chloro-1H-indazole | 8.03 (s, 1H), 7.87 (s, 1H), 7.69 (d, 1H), 7.51 (m, 3H), 7.35 (dd, 1H), 6.78 (m, 2H), 5.97 (br, 1H), 5.34 (q, 1H), 4.74 (d, 1H), 3.57 (d, 1H), 1.34 (d, 3H) |
| 60 | 5-bromo-2H-indazole | 8.23 (s, 1H), 7.84 (d, 1H), 7.83 (s, 1H), 7.64 (s, 1H), 7.55 (m, 2H), 7.41 (dd, 1H), 6.83 (m, 2H), 5.34 (q, 1H), 4.84 (d, 1H), 3.49 (d, 1H), 1.45 (d, 3H) |
| 61 | 5-bromo-1H-indazole | 8.10 (s, 1H), 7.96 (s, 2H), 7.58 (m, 3H), 7.52 (d, 1H), 6.85 (m, 2H), 5.93 (br, 1H), 5.38 (q, 1H), 4.78 (d, 1H), 3.63 (d, 1H), 1.40 (d, 3H) |
| 62 | 5-cyano-1H-indazole | 8.34 (d, 2 H, J = 7.9 Hz), 8.19 (s, 1H), 7.84 (d, 1 H, J = 8.8 Hz), 7.69 (dd, 1 H, J = 8.9 Hz, 1.5 Hz), 7.63 (s, 1H), 7.48 (m, 1H), 6.91 (m, 2H), 5.53 (m, 1H), 4.95 (m, 1H), 3.81 (m, 1H), 1.47 (dd, 3H, J = 6.9 Hz, 2.0 Hz). |
| 63 | 3-iodo-5-nitro-1H-indazole | 8.79 (s, 1H), 8.36 (m, 1H), 7.89 (br, 1H), 7.70 (d, 1 H, J = 9.3 Hz), 7.62 (m, 2H), 6.82 (m, 2H), 5.73 (br, 1 H, —OH), 5.43 (q, 1H), 4.88 (d, 1 H, J = 14.1 Hz), 3.76 (d, 1 H, J = 14.2 Hz), 1.5 (d, 3H, J = 7.0 Hz) |
| 64 | 3-methyl-2H-indazole | 8.31 (s, 1H), 7.81 (s, 1H), 7.59 (d, 1H), 7.48 (m, 2H), 7.22 (m, 2H), 6.78 (m, 2H), 6.38 (br, 1H), 5.35 (q, 1H), 4.82 (d, 1H), 3.48 (d, 1H), 2.82 (s, 3H), 1.43 (d, 3H) |

TABLE 3-continued

| Ex. | Het | ¹H-NMR (300 MHz, CDCl₃) δ |
|---|---|---|
| 65 | (indazole structure, 3-methyl-1H-indazol-1-yl) | 8.28 (s, 1H), 7.74 (s, 1H), 7.59 (d, 1H), 7.48 (m, 2H), 7.35 (m, 1H), 7.12 (m, 1H), 6.83(m, 2H), 6.38 (br, 1H), 5.33 (q, 1H), 4.82 (d, 1H), 3.48 (d, 1H), 2.62 (s, 3H), 1.38 (d, 3H) |

Example 66

(2R,3R)-2-(2,4-Difluorophenyl)-3-(4-fluoro-3-methyl-1H-indazol-1-yl)-1-(1H-1,2,4-triazol-1-yl)butan-2-ol With reference to the literature (*J. Med. Chem.*, 1994, 37(17), 2721~2734), the two-step procedure described below was performed to synthesize the title compound.

Step 1) Synthesis of 4-fluoro-3-methyl-1H-indazole

2',6'-Difluoroacetophenone (0.468 g, 3 mmol) was dissolved in anhydrous hydrazine (2 ml), followed by irradiating microwaves thereon with stirring at 150° C. for 5 min. The addition of water (0.5 ml) at 0° C. terminated the reaction. Afterwards, the reaction solution was diluted with ethyl acetate (10 ml) and washed with water. The organic layer was dried over anhydrous magnesium sulfate and concentrated using vacuum evaporation. The residue was re-crystallized in dichloromethane to give the title compound (Yield 85%).

¹H-NMR (300 MHz, CDCl₃) δ 7.37-7.32 (m, 2H), 6.91 (m, 1H), 2.79 (s, 3H).

Step 2) Synthesis of (2R,3R)-2-(2,4-difluorophenyl)-3-(4-fluoro-3-methyl-1H-indazol-1-yl)-1-(1H-1,2,4-triazol-1-yl)butan-2-ol From 4-fluoro-3-methyl-1H-indazole, obtained in Step 1), the title compound was prepared in a manner similar to that of Example 50 (Yield 40%).

¹H-NMR (300 MHz, CDCl₃) δ 8.29 (s, 1H), 7.69 (s, 1H), 7.54 (m, 1H), 7.38 (m, 1H), 7.24 (m, 1H), 6.82 (m, 3H), 5.30 (m, 1H), 4.80 (d, 1H, J=14.1 Hz), 3.75 (d, 1H, J=14.2 Hz), 2.75 (s, 3H), 1.35 (d, 3H).

Example 67

(2R,3R)-2-(2,4-Difluorophenyl)-3-(4-fluoro-3-methyl-2H-indazol-2-yl)-1-(1H-1,2,4-triazol-1-yl)butan-2-ol The crude product of Example 66 was purified by chromatography on silica gel to give the title compound (Yield 41%).

¹H-NMR (300 MHz, CDCl₃) δ 8.31 (s, 1H), 7.72 (s, 1H), 7.48 (m, 2H), 7.24 (m, 1H), 6.82 (m, 3H), 5.98 (br, 1H), 5.30 (m, 1H), 4.80 (d, 1H), 3.76 (d, 1H), 2.75 (s, 3H), 1.31 (d, 3H).

Examples 68 to 105

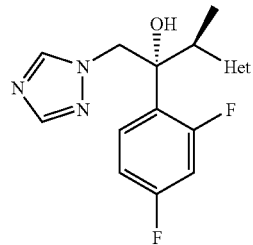

Compounds of the chemical formula above, wherein Het is as listed in Table 4, below, were synthesized in a procedure similar to that of Example 66.

TABLE 4

| Ex. | Het | ¹H-NMR (300 MHz, CDCl₃) δ |
|---|---|---|
| 68 | (4-chloro-3-methyl-indazol-1-yl, mixed) | 8.11 (s, 1H), 7.89 (s, 1H), 7.5 (7 m, 1H), 7.28 (m, 1H), 7.24 (m, 1H), 6.79 (m, 3H), 5.30 (m, 1H), 4.80 (d, 1 H, J = 14.1 Hz), 3.75 (d, 1 H, J = 14.2 Hz), 2.75 (s, 3H), 1.35 (d, 3H) |
| 69 | (4-chloro-3-methyl-indazol-1-yl) | 8.11 (s, 1H), 7.89 (s, 1H), 7.57 (m, 1H), 7.28 (m, 1H), 7.24 (m, 1H), 6.79 (m, 3H), 5.30 (m, 1H), 4.82 (d, 1H), 3.76 (d, 1H), 2.76 (s, 3H), 1.33 (d, 3H) |

TABLE 4-continued

| Ex. | Het | ¹H-NMR (300 MHz, CDCl₃) δ |
|---|---|---|
| 70 | 3-methyl-4-(trifluoromethyl)-2H-indazol-2-yl | 8.21 (s, 1H), 7.88 (s, 1H), 7.57 (m, 1H), 7.28 (m, 1H), 7.26 (m, 1H), 6.79 (m, 3H), 5.30 (m, 1H), 4.80 (d, 1 H, J = 14.2 Hz), 3.73 (d, 1 H, J = 14.2 Hz), 2.78 (s, 3H), 1.41 (d, 3H) |
| 71 | 3-methyl-4-(trifluoromethyl)-1H-indazol-1-yl | 8.21 (s, 1H), 7.91 (s, 1H), 7.62 (m, 1H), 7.30 (m, 1H), 7.01~6.79 (m, 4H), 6.02 (br, 1H), 5.30 (m, 1H), 4.80 (d, 1H), 3.73 (d, 1H), 2.78 (s, 3H), 1.39 (d, 3H) |
| 72 | 5-fluoro-3-methyl-2H-indazol-2-yl | 8.36 (s, 1H), 7.69 (s, 1H), 7.45 (dd, 2H), 7.21 (m, 2H), 6.86 (m, 2H), 5.36 (m, 1H), 4.74 (d, 1 H, J = 13.8 Hz), 3.59 (d, 1 H, J = 13.8 Hz), 2.73 (s, 3H), 1.39 (d, 3 H, J = 6.9 Hz) |
| 73 | 5-fluoro-3-methyl-1H-indazol-1-yl | 8.36 (s, 1H), 7.69 (s, 1H), 7.51 (m, 2H), 7.21 (m, 2H), 6.91 (m, 2H), 5.41 (m, 1H), 4.72 (d, 1H). 3.48 (d, 1H), 2.75 (s, 3H), 1.42 (d, 3H) |
| 74 | 3-methyl-5-(trifluoromethyl)-2H-indazol-2-yl | 7.95 (s, 1H),, 7.76 (d, 1H), 7.68 (m, 4H), 6.86 (m, 2H), 5.42 (q, 1H), 4.67 (d, 1 H, J = 12.9 Hz), 3.58 (d, 1 H, J = 14.0 Hz), 2.81 (s, 1H), 1.41 (d, 1 H, J = 6.8 Hz) |
| 75 | 3-methyl-5-(trifluoromethyl)-1H-indazol-1-yl | 8.00 (s, 1H), 7.86 (s, 1H), 7.58 (m, 4H), 6.82 (m, 2H), 6.02 (br, 1H), 5.36 (q, 1H), 4.76 (d, 1 H, J = 14.2 Hz), 3.71 (d, 1 H, J = 14.2 Hz), 2.64 (s, 3H), 1.34 (d, 3 H, J = 6.9 Hz) |
| 76 | 6-fluoro-3-methyl-2H-indazol-2-yl | 7.93 (s, 1H), 7.65 (m, 1H), 7.60 (m, 2H), 7.15 (dd, 1H), 6.98 (dd, 1H), 6.83 (m, 2H), 5.22 (q, 1H), 4.76 (d, 1 H, J = 14.2 Hz), 3.74 (d, 1 H, J = 14.2 Hz), 2.61 (s, 3H), 1.31 (d, J = 6.8 Hz) |
| 77 | 6-fluoro-3-methyl-1H-indazol-1-yl | 7.88 (s, 1H), 7.71 (m, 1H), 7.58 (m, 2H), 7.05 (dd, 1H), 6.98 (dd, 1H), 6.83 (m, 2H), 5.23 (q, 1H), 4.76 (d, 1H), 3.74 (d, 1H), 2.61 (s, 3H), 1.31 (d, 3 H, J = 6.8 Hz) |
| 78 | 3-methyl-6-(trifluoromethyl)-2H-indazol-2-yl | 7.95 (s, 1H),, 7.76 (d, 1H), 7.68 (m, 4H), 6.86 (m, 2H), 5.42 (q, 1H), 4.67 (d, 1 H, J = 12.9 Hz), 3.58 (d, 1 H, J = 14.0 Hz), 2.81 (s, 1H), 1.45 (d, 1 H, J = 6.7 Hz) |
| 79 | 3-methyl-6-(trifluoromethyl)-1H-indazol-1-yl | 8.00 (s, 1H), 7.86 (s, 1H), 7.58 (m, 4H), 6.82 (m, 2H), 6.10 (br, 1H), 5.36 (q, 1H), 4.76 (d, 1 H, J = 14.2 Hz), 3.71 (d, 1 H, J = 14.2 Hz), 2.64 (s, 3H), 1.41 (d, 3 H, J = 6.8 Hz) |

TABLE 4-continued

| Ex. | Het | ¹H-NMR (300 MHz, CDCl₃) δ |
|---|---|---|
| 80 | indazole (4,6-diF, 3-Me, N2-linked) | 7.82 (s, 1H), 7.66 (m, 1H), 7.60(m, 2H), 7.15 (dd, 1H), 6.98 (dd, 1H), 6.86 (m, 2H), 5.32 (q, 1H), 4.76 (d, 1 H, J = 14.2 Hz), 3.74 (d, 1 H, J = 14.2 Hz), 2.61 (s, 3H), 1.38 (d, 3 H, J = 6.9 Hz) |
| 81 | indazole (4,6-diF, 3-Me, N1-linked) | 7.88 (s, 1H), 7.71 (m, 1H), 7.58 (m, 2H), 7.05 (dd, 1H), 6.98 (dd, 1H), 6.83 (m, 2H), 5.23 (q, 1H), 4.76 (d, 1H), 3.74 (d, 1H), 2.61 (s, 3H), 1.35 (d, 3 H, J = 6.8 Hz) |
| 82 | indazole (4-Cl, 6-F, 3-Me, N2-linked) | 8.02 (s, 1H), 7.76 (m, 1H), 7.60 (m, 2H), 7.15 (dd, 1H), 6.98 (dd, 1H), 6.86 (m, 2H), 5.32 (q, 1H), 4.76 (d, 1 H, J = 14.2 Hz), 3.74 (d, 1 H, J = 14.2 Hz), 2.61 (s, 3H), 1.38 (d, 3 H, J = 6.9 Hz) |
| 83 | indazole (4-Cl, 6-F, 3-Me, N1-linked) | 8.16 (s, 1H), 7.71 (m, 1H), 7.58 (m, 2H), 7.05 (dd, 1H), 6.98 (dd, 1H), 6.83(m, 2H), 5.23 (q, 1H), 4.76 (d, 1H), 3.74 (d, 1H), 2.61 (s, 3H), 1.35 (d, 3 H, J = 6.8 Hz) |
| 84 | indazole (5,6-diF, 3-Me, N2-linked) | 7.92 (s, 1H), 7.58 (m, 2H), 7.42 (m, 1H), 6.82 (m, 2H), 5.31 (m, 1H), 4.64 (d, 1 H, J = 14.0 Hz), 3.53 (d, 1 H, J = 14.0 Hz), 2.70 (s, 3H), 1.36 (d, 3 H, J = 6.8 Hz) |
| 85 | indazole (5,6-diF, 3-Me, N1-linked) | 7.98 (s, 1H), 7.66 (m, 2H), 7.42 (m, 1H), 6.82 (m 2H), 5.31 (m, 1H), 4.54 (d, 1 H, J = 14.0 Hz), 3.53 (d, 1 H, J = 14.1 Hz), 2.70 (s, 3H), 1.29 (d, 3 H, J = 6.7 Hz) |
| 86 | indazole (6-Cl, 5-F, 3-Me, N2-linked) | 8.02 (s, 1H), 7.62 (m, 2H), 7.42 (m, 1H), 6.82 (m, 2H), 5.31 (m, 1H), 4.64 (d, 1 H, J = 14.2 Hz), 3.55 (d, 1 H, J = 14.2 Hz), 2.75 (s, 3H), 1.41 (d, 3 H, J = 6.8 Hz) |
| 87 | indazole (6-Cl, 5-F, 3-Me, N1-linked) | 8.22 (s, 1H), 7.86 (m, 2H), 7.42 (m, 1H), 6.82 (m, 2H), 5.31 (m, 1H), 4.54 (d, 1 H, J = 14.0 Hz), 3.53 (d, 1 H, J = 14.1 Hz), 2.74 (s, 3H), 1.39 (d, 3 H, J = 6.7 Hz) |
| 88 | indazole (4-Cl, 7-?, 3-Me, N2-linked) | 8.22 (s, 1H), 7.72 (m, 2H), 7.38 (m, 1H), 6.82 (m, 2H), 5.31 (m, 1H), 4.64 (d, 1 H, J = 14.2 Hz), 3.55 (d, 1 H, J = 14.2 Hz), 2.75 (s, 3H), 1.39 (d, 3 H, J = 6.8 Hz) |

TABLE 4-continued

| Ex. | Het | ¹H-NMR (300 MHz, CDCl₃) δ |
|---|---|---|
| 89 | 7-methyl-4-chloro-3-methyl-1H-indazole | 8.25 (s, 1H), 7.86 (m, 2H), 7.33 (m, 1H), 6.92 (m, 2H), 6.01 (br, 1H), 5.33 (m, 1H), 4.54 (d, 1 H, J = 14.0 Hz), 3.53 (d, 1 H, J = 14.1 Hz), 2.74 (s, 3H), 1.38 (d, 3 H, J = 6.9 Hz) |
| 90 | 6,7-difluoro-3-methyl-2H-indazole | 8.69 (s, 1H), 7.78 (s, 1H), 7.45 (m, 2H), 7.07 (m, 1H), 6.88 (m, 2H), 5.65 (m, 1H), 4.98 (d, 1 H, J = 14.2 Hz), 3.97 (d, 1 H, J = 14.1 Hz), 1.32 (d, 3 H, J = 6.8 Hz) |
| 91 | 6,7-difluoro-3-methyl-1H-indazole | 8.71 (s, 1H), 7.82 (s, 1H), 7.55 (m, 1H), 7.41 (m, 1H), 7.07 (m, 1H), 6.87 (m, 2H), 5.65 (m, 1H), 4.98 (d, 1 H, J = 14.2 Hz), 3.97 (d, 1 H, J = 14.0 Hz), 1.32 (d, 3 H, J = 6.8 Hz) |
| 92 | 5,6,7-trifluoro-3-methyl-2H-indazole | 7.99 (s, 1H), 7.57 (m, 2H), 6.83 (m, 2H), 5.98 (br, 1H), 5.26 (m, 1H), 4.48 (d, 1H), 4.42 (d, 1H), 2.87 (s, 2H), 1.35 (d, 3H) |
| 93 | 5,6,7-trifluoro-3-methyl-1H-indazole | 8.02 (s, 1H), 7.61 (m, 2H), 7.32 (m, 1H), 6.78 (m, 2H), 5.36 (m, 1H), 4.84 (d, 1H), 4.42 (d, 1H), 2.73 (s, 3H), 1.33 (d, 3H) |
| 94 | 4,5,6,7-tetrafluoro-3-methyl-2H-indazole | 7.99 (s, 1H), 7.57 (m, 2H), 6.83 (m, 2H), 5.98 (br, 1H), 5.26 (m, 1H), 4.77 (d, 1H), 4.42 (d, 1H), 2.87 (s, 3H), 1.37 (d, 3H) |
| 95 | 4,5,6,7-tetrafluoro-3-methyl-1H-indazole | 8.02 (s, 1H), 7.61 (m, 1H), 7.32 (m, 1H), 6.78 (m, 2H), 5.36 (m, 1H), 4.84 (d, 1H), 4.42 (d, 1H), 2.73 (s, 3H), 1.32 (d, 3H) |
| 96 | 3-ethyl-1H-indazole | 7.98 (s, 1H), 7.76 (d, 1 H, J = 8.1 Hz), 7.56~7.48 (m, 4H), 7.20 (m, 1H), 6.84 (m, 2H), 5.37 (q, 1H), 4.75 (d, 1 H, J = 14.2 Hz), 3.64 (d, 1 H, J = 14.2 Hz), 3.07 (q, 2H), 1.46 (t, 3H), 1.32 (d, 3 H, J = 6.8 Hz) |

TABLE 4-continued

| Ex. | Het | ¹H-NMR (300 MHz, CDCl₃) δ |
|---|---|---|
| 97 | (indazol-1-yl, 3-ethyl) | 8.02 (s, 1H), 7.77 (d, 1H), 7.56~7.48 (m, 4H), 7.25 (m, 1H), 6.84 (m, 2H), 6.03 (br, 1H), 5.32 (q, 1H), 4.75 (d, 1 H, J = 14.2 Hz), 3.64 (d, 1 H, J = 14.1 Hz), 3.17 (q, 2H), 1.46 (t, 3H), 1.31 (d, 3 H, J = 6.8 Hz) |
| 98 | (indazol-2-yl, 3-ethyl, 4-F) | 8.01 (s, 1H), 7.57 (m, 1H), 7.54 (m, 1H), 7.46 (m, 1H), 7.35 (dd, 1H), 7.25 (m, 1H), 6.81 (m, 2H), 6.24 (br, 1 H, —OH), 5.32 (q, 1H), 4.74 (d, 1H), 3.66 (d, 1H), 3.01 (q, 2H), 1.44 (t, 3H), 1.32 (d, 3 H, J = 6.8 Mz) |
| 99 | (indazol-1-yl, 3-ethyl, 4-F) | 8.12 (s, 1H), 7.67 (m, 1H), 7.50 (m, 2H), 7.35 (m, 1H), 7.25 (m, 1H), 6.81 (m, 2H), 6.24 (br, 1 H, —OH), 5.32 (q, 1H), 4.74 (d, 1H), 3.66 (d, 1H), 3.01 (q, 2H), 1.44 (t, 3H), 1.30 (d, 3 H, J = 6.9 Hz) |
| 100 | (indazol-2-yl, 3-ethyl, 5-F) | 7.92 (s, 1H), 7.57 (m, 1H), 7.54 (m, 1H), 7.46 (m, 1H), 7.35 (dd, 1H), 7.25 (m, 1H), 6.81 (m, 2W), 6.24 (br, 1 H, —OH), 5.32 (q, 1H), 4.74 (d, 1H), 3.66 (d, 1H), 3.01 (q, 2H), 1.44 (t, 3H), 1.32 (d, 3 H, J = 6.8 Hz) |
| 101 | (indazol-1-yl, 3-ethyl, 5-F) | 7.99 (s, 1H), 7.67 (m, 1H), 7.50 (m, 2H), 7.35 (m, 1H), 7.25 (m, 1H), 6.81 (m, 2H), 6.24 (br, 1 H, —OH), 5.32 (q, 1H), 4.74 (d, 1H), 3.66 (d, 1H), 3.01 (q, 2H), 1.44 (t, 3H), 1.30 (d, 3 H, J = 6.9 Mz) |
| 102 | (indazol-2-yl, 3-ethyl, 6-F) | 7.88 (s, 1H), 7.66 (m, 1H), 7.54 (m, 2H), 7.14 (m, 1H), 6.94 (dd, 1H), 6.78 (m, 2H), 6.28 (br, 1 H, —OH), 5.22 (q, 1H), 4.74 (d, 1H), 3.68 (d, 1H), 3.00 (q, 2H), 1.42 (t, 3H), 1.30 (d, 3 H, J = 6.8 Mz) |
| 103 | (indazol-1-yl, 3-ethyl, 6-F) | 7.93 (s, 1H), 7.72 (m, 1H), 7.54 (m, 2H), 7.14 (m, 1H), 6.94 (dd, 1H), 6.78 (m, 2H), 6.12 (br, 1 H, —OH), 5.22 (q, 1H), 4.74 (d, 1H), 3.68 (d, 1H), 3.00 (q, 2H), 1.42 (t, 3H), 1.32 (d, 3 H, J = 6.8 Mz) |
| 104 | (indazol-2-yl, 3-ethyl, 6-CF₃) | 7.84 (s, 1H), 7.80 (m, 2H), 7.54 (m, 1H), 7.53 (s, 1H), 7.33 (d, 1 H, J = 8.7 Hz), 6.73 (m, 2H), 6.17 (br, 1H), 5.37 (q, 1H), 4.77 (d, 1 H, J = 14.4 Hz), 3.73 (d, 1 H, J = 14.2 Hz), 3.03 (q, 2H), 1.44 (t, 3H), 1.34 (d, 3 H, J = 6.9 Hz) |

TABLE 4-continued

| Ex. | Het | ¹H-NMR (300 MHz, CDCl₃) δ |
|---|---|---|
| 105 | (indazole with CF₃ and ethyl substituents) | 8.02 (s, 1H), 7.85 (m, 2H), 7.54 (m, 1H), 7.53 (s, 1H), 7.23 (d, 1 H, J = 8.8 Hz), 6.83 (m, 2H), 5.37 (q, 1H), 4.77 (d, 1 H J = 14.4 Hz), 3.73 (d, 1 H, J = 14.2 Hz), 3.03 (q, 2H), 1.44 (t, 3H), 1.36 (t, 3 H J = 6.8 Hz) |

Example 106

(2R,3R)-2-(2,4-Difluorophenyl)-3-(3-methyl-5-nitro-1H-indazol-1-yl)-1-(1H-1,2,4-triazol-1-yl)butan-2-ol With reference to the literature (Synthesis, 1999, 4, 588–592) and Example 66, the following three-step procedure was performed to synthesize the title compound.

Step 1) Synthesis of 1-(2-hydroxy-5-nitrophenyl)ethanone

4-Nitrophenol (1.61 g, 11.6 mmol) was dissolved in dichloroethane (10 ml) and aluminum chloride (2.31 g, 17.3 mmol) was slowly added in three portions. The addition of acetylchloride (0.818 ml, 11.51 mmol) was followed by stirring at 50° C. for 2 hours. The reaction was terminated with the addition of ice water (10 ml) and 2N hydrochloric acid solution (10 ml) at 0° C. The reaction mixture was extracted with dichloroethane (10 ml). The organic layer was dried over anhydrous magnesium sulfate and concentrated using vacuum evaporation. The crude product was purified by chromatography on silica gel to give the title compound (Yield 78%).

Step 2) Synthesis of 3-methyl-5-nitro-1H-indazole

A solution of 1-(2-hydroxy-5-nitrophenyl)ethanone (0.54 g, 3 mmol) in anhydrous hydrazine (2 ml) was radiated with microwaves while being stirred at 150° C. for 5 min. Water (0.5 ml) was added at 0° C. to terminate the reaction. The reaction solution was diluted with ethyl acetate (10 ml) and washed with water. The organic layer was dried over anhydrous magnesium sulfate and concentrated using vacuum evaporation. Recrystallization of the residue in dichloromethane produced the title compound (Yield 80%).

¹H-NMR (300 MHz, CDCl₃) δ 8.78 (s, 1H), 8.27 (m, 1H), 7.86 (m, 1H), 2.79 (s, 3H).

Step 3) Synthesis of (2R,3R)-2-(2,4-difluorophenyl)-3-(3-methyl-5-nitro-1H-indazol-1-yl)-1-(1H-1,2,4-triazol-1-yl)butan-2-ol From 3-methyl-5-nitro-1H-indazole, obtained in Step 2), the title compound was prepared using a procedure similar to that of Example 50 (Yield 40%).

¹H-NMR (300 MHz, CDCl₃) δ 8.12 (s, 1H), 7.79 (m, 2H), 7.92 (s, 1H), 7.64 (m, 3H), 6.83 (m, 2H), 5.74 (br, 1H), 5.43 (q, 1H), 4.88 (d, 1H, J=14.2 Hz), 3.76 (d, 1H, J=14.2 Hz), 2.81 (s, 3H), 1.49 (d, 3H, J=6.8 Hz).

Example 107

(2R,3R)-2-(2,4-Difluorophenyl)-3-(3-methyl-5-nitro-1H-indazol-1-yl)-1-(1H-1,2,4-triazol-1-yl)butan-2-ol The crude product of Example 106 was purified by chromatography on silica gel to give the title product (Yield 45%).

¹H-NMR (300 MHz, CDCl₃) δ 8.33 (s, 1H), 8.01 (m, 2H), 7.92 (s, 1H), 7.64 (m, 3H), 6.83 (m, 2H), 5.74 (br, 1H), 5.43 (q, 1H), 4.98 (d, 1H, J=14.2 Hz), 3.76 (d, 1H, J=14.2 Hz), 2.82 (s, 3H), 1.51 (d, 3H, J=6.8 Hz).

Example 108

(2R,3R)-3-(5-amino-3-methyl-2H-indazol-1-yl)-2-(2,4-difluorophenyl)-1-(1H-1,2,4-triazol-1-yl)butan-2-ol The same procedure as in Example 6 was conducted, except that (2R,3R)-2-(2,4-difluorophenyl)-3-(3-methyl-5-nitro-1H-indazol-1-yl)-1-(1H-1,2,4-triazol-1-yl)butan-2-ol was used, to prepare the title compound.

¹H-NMR (300 MHz, CDCl₃) δ 7.96 (s, 1H), 7.93 (s, 1H), 7.58 (m, 2H), 7.48 (d, 1H, J=8.9 Hz), 7.25 (m, 1H), 7.17 (m, 1H), 6.86 (m, 2H), 6.05 (br, 1H, —OH), 5.37 (q, 1H), 4.76 (d, 1H, J=15.1 Hz), 3.60 (d, 1H, J=14.2 Hz), 2.89 (s, 3H), 1.53 (d, 3H, J=6.9 Hz).

Example 109

(2R,3R)-3-(5-amino-3-methyl-1H-indazol-1-yl)-2-(2,4-difluorophenyl)-1-(1H-1,2,4-triazol-1-yl)butan-2-ol The same procedure as in Example 6, except that (2R,3R)-2-(2,4-difluorophenyl)-3-(3-methyl-5-nitro-2H-indazol-1-yl)-1-(1H-1,2,4-triazol-1-yl)butan-2-ol was used, was conducted to prepare the title compound.

¹H-NMR (300 MHz, CDCl₃) δ 8.12 (s, 1H), 7.93 (s, 1H), 7.68 (m, 2H), 7.48 (d, 1H, J=8.9 Hz), 7.25 (m, 1H), 7.17 (m, 1H), 6.86 (m, 2H), 6.02 (br, 1H, —OH), 5.38 (q, 1H), 4.68 (d, 1H, J=14.1 Hz), 3.60 (d, 1H, J=14.2 Hz), 2.91 (s, 3H), 1.55 (d, 3H, J=6.8 Hz).

Example 110

(2R,3R)-3-(5-chloro-3-methyl-2H-indazol-1-yl)-2-(2,4-difluorophenyl)-1-(1H-1,2,4-triazol-1-yl)butan-2-ol Synthesis was made as follows with reference to the literature (*Syn. Comm.* 27(12), 1997, 218~2191).

In a nitrogen atmosphere, copper(II) chloride (0.524 g, 3.9 mmol) and tert-butyl nitrite (0.57 ml, 4.8 mmol) were added to acetonitrile (10 ml) and heated to 65° C. To this, a solution of (2R,3R)-3-(5-amino-3-methyl-2H-indazol-1-yl)-2-(2,4-difluorophenyl)-1-(1H-1,2,4-triazol-1-yl)butan-2-ol in acetonitrile (8 ml) was slowly added for 10 min. After stirring for 1 hour, the addition of 6N HCl solution (30 ml) at 0° C. terminated the reaction. The reaction mixture was extracted three times with ethylacetate (30 ml) and washed three times with water (30 ml). The organic layer was dried over anhydrous magnesium sulfate and vacuum dried to concentrate it. The crude product was purified by chromatography on silica gel to give the title compound (Yield 53%).

$^1$H-NMR (300 MHz, CDCl$_3$) δ 8.62 (s, 1H), 7.95 (s, 1H), 7.57 (s, 1H), 7.48 (m, 2H), 7.23 (s, 1H), 6.84 (m, 2H), 6.13 (s, 1H), 5.35 (q, 1H), 4.79 (d, 1H, J=14.2 Hz), 3.78 (d, 1H, J=14.2 Hz), 2.63 (s, 3H), 1.39 (d, 3H, J=6.8 Hz).

Examples 111 to 233

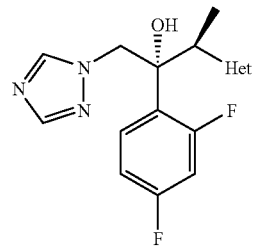

Compounds of the chemical formula above, wherein Het is as listed in Table 5 below, were synthesized according to procedures similar to those of Examples 106 to 110.

TABLE 5

| Ex. | Het | $^1$H-NMR(300 MHz, CDCl$_3$) δ |
|---|---|---|
| 111 | 5-chloro-3-methyl-indazol-1-yl | 7.90(s, 1 H), 7.69(s, 1 H), 7.58(s, 1 H), 7.46(m, 2 H), 7.28(s, 1 H), 6.82(m, 2 H), 6.11(s, 1 H), 5.32(q, 1 H), 4.77(d, 1 H, J = 14.2 Hz), 3.72(d, 1 H, J = 14.2 Hz), 2.62(s, 3 H), 1.34(d, 3 H, J = 6.8 Hz) |
| 112 | 7-nitro-3-methyl-2H-indazol-2-yl | 8.05(s, 1 H), 7.98(m, 2 H), 7.90(s, 1 H), 7.84(m, 2 H), 6.83(m, 2 H), 6.11(br, 1 H), 5.43(q, 1 H), 4.86(d, 1 H, J = 14.2 Hz), 3.75(d, 1 H, J = 14.1 Hz), 2.74(s, 3 H), 1.41(d, 3 H, J = 6.8 Hz) |
| 113 | 7-nitro-3-methyl-indazol-1-yl | 8.33(s, 1 H), 8.01(m, 2 H), 7.90(s, 1 H), 7.84(m, 2 H), 6.83(m, 2 H), 6.13(br, 1 H) 5.74(br, 1 H), 5.43(q, 1 H), 4.86(d, 1 H, J = 14.2 Hz), 3.57(d, 1 H, J = 14.1 Hz), 2.81(s, 3 H), 1.40(d, 3 H, J = 6.8 Hz) |
| 114 | 7-fluoro-3-methyl-2H-indazol-2-yl | 8.11(s, 1 H), 7.98(m, 2 H), 7.90(s, 1 H), 7.84(m, 3 H), 6.83(m, 2 H), 5.43(q, 1 H), 4.86(d, 1 H, J = 14.2 Hz), 3.75(d, 1 H, J = 14.1 Hz), 2.74(s, 3 H), 1.43(d, 3 H, J = 6.8 Hz) |
| 115 | 7-fluoro-3-methyl-indazol-1-yl | 8.43(s, 1 H), 8.01(m, 2 H), 7.90(s, 1 H), 7.84(m, 2 H), 6.83(m, 2 H), 6.03(br, 1 H), 5.51(q, 1 H), 4.58(d, 1 H, J = 14.2 Hz), 3.47(d, 1 H, J = 14.2 Hz), 2.81(s, 3 H), 1.39(d, 3 H, J = 6.8 Hz) |

TABLE 5-continued

| Ex. | Het | $^1$H-NMR(300 MHz, CDCl$_3$) δ |
|---|---|---|
| 116 | 7-Cl-3-methyl-2H-indazol-2-yl | 8.11(s, 1 H), 7.98(m, 2 H), 7.90(s, 1 H), 7.84(m, 2 H), 6.83(m, 2 H), 5.43(q, 1 H), 4.86(d, 1 H, J = 14.2 Hz), 3.75(d, 1 H, J = 14.1 Hz), 2.74(s, 3 H), 1.43(d, 3 H, J = 6.8 Hz) |
| 117 | 7-Cl-3-methyl-1H-indazol-1-yl | 8.12(s, 1 H), 8.03(m, 2 H), 7.85(m, 4 H), 6.79(m, 2 H), 6.02(br, 1 H), 5.51(q, 1 H), 4.58(d, 1 H, J = 14.2 Hz), 3.47(d, 1 H, J = 14.2 Hz), 2.81(s, 3 H), 1.42(d, 3 H, J = 6.8 Hz) |
| 118 | 5-Br-7-F-3-methyl-2H-indazol-2-yl | 8.01(s, 1 H), 7.78(m, 2 H), 7.68(s, 1 H), 7.24(m, 1 H), 6.83(m, 2 H), 5.33(q, 1 H), 4.76(d, 1 H, J = 14.2 Hz), 3.75(d, 1 H, J = 14.1 Hz), 2.74(s, 3 H), 1.33(d, 3 H, J = 6.8 Hz) |
| 119 | 5-Br-7-F-3-methyl-1H-indazol-1-yl | 8.10(s, 1 H), 8.03(m, 2 H), 7.85(m, 2 H), 6.79(m, 2 H), 6.02(br, 1 H), 5.51(q, 1 H), 4.58(d, 1 H, J = 14.2 Hz), 3.47(d, 1 H, J = 14.2 Hz), 2.81(s, 3 H), 1.31(d, 3 H, J = 6.8 Hz) |
| 120 | 5-Br-7-Cl-3-methyl-2H-indazol-2-yl | 8.03(s, 1 H), 7.84(m, 1 H), 7.68(s, 1 H), 7.24(m, 2 H), 6.83(m, 2 H), 5.33(q, 1 H), 4.76(d, 1 H, J = 14.2 Hz), 3.75(d, 1 H, J = 14.1 Hz), 2.74(s, 3 H), 1.35(d, 3 H, J = 6.8 Hz) |
| 121 | 5-Br-7-Cl-3-methyl-1H-indazol-1-yl | 8.10(s, 1 H), 8.03(m, 2 H), 7.85(m, 2 H), 6.79(m, 2 H), 5.98(br, 1 H), 5.51(q, 1 H), 4.58(d, 1 H, J = 14.2 Hz), 3.47(d, 1 H, J = 14.2 Hz), 2.81(s, 3 H), 1.33(d, 3 H, J = 6.9 Hz) |
| 122 | 7-F-3,5-dimethyl-2H-indazol-2-yl | 8.13(s, 1 H), 7.84(m, 2 H), 7.72(s, 1 H), 7.24(m, 1 H), 6.83(m, 2 H), 5.33(q, 1 H), 4.76(d, 1 H, J = 14.2 Hz), 3.75(d, 1 H, J = 14.1 Hz), 2.74(s, 3 H), 2.55(s, 3 H), 1.42(d, 3 H, J = 6.8 Hz) |
| 123 | 7-F-3,5-dimethyl-1H-indazol-1-yl | 8.18(s, 1 H), 8.03(m, 2 H), 7.80(m, 2 H), 6.79(m, 2 H), 5.98(br, 1 H), 5.51(q, 1 H), 4.58(d, 1 H, J = 14.2 Hz), 3.47(d, 1 H, J = 14.2 Hz), 2.81(s, 3 H), 2.56(s, 3 H), 1.40(d, 3 H, J = 6.8 Hz) |

TABLE 5-continued

| Ex. | Het | $^1$H-NMR(300 MHz, CDCl$_3$) δ |
|---|---|---|
| 124 | 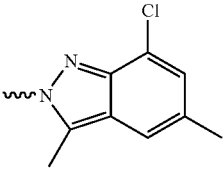 | 8.15(s, 1 H), 7.84(m, 2 H), 7.72(s, 1 H), 7.24(m, 1 H), 6.83(m, 2 H), 5.31(q, 1 H), 4.76(d, 1 H, J = 14.2 Hz), 3.75(d, 1 H, J = 14.1 Hz), 2.74(s, 3 H), 2.53(s, 3 H), 1.39(d, 3 H, J = 6.8 Hz) |
| 125 | 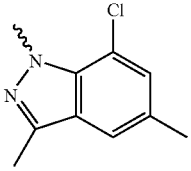 | 8.16(s, 1 H), 8.03(m, 2 H), 7.80(m, 2 H), 6.79(m, 2 H), 5.98(br, 1 H), 5.51(q, 1 H), 4.58(d, 1 H, J = 14.2 Hz), 3.47(d, 1 H, J = 14.2 Hz), 2.81(s, 3 H), 2.55(s, 3 H), 1.37(d, 3 H, J = 6.8 Hz) |
| 126 | 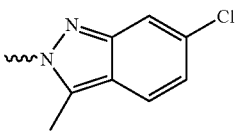 | 8.13(s, 1 H), 7.98(m, 2 H), 7.90(s, 1 H), 7.84(m, 2 H), 6.83(m, 2 H), 5.43(q, 1 H), 4.86(d, 1 H, J = 14.2 Hz), 3.75(d, 1 H, J = 14.1 Hz), 2.74(s, 3 H), 1.37(d, 3 H, J = 6.8 Hz) |
| 127 | 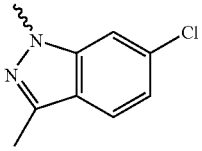 | 8.15(s, 1 H), 8.01(m, 2 H), 7.85(m, 4 H), 6.79(m, 2 H), 6.02(br, 1 H), 5.51(q, 1 H), 4.58(d, 1 H, J = 14.2 Hz), 3.47(d, 1 H, J = 14.2 Hz), 2.81(s, 3 H), 1.36(d, 3 H, J = 6.8 Hz) |
| 128 | 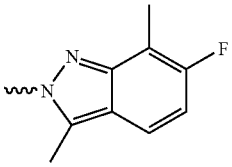 | 8.25(s, 1 H), 7.94(m, 2 H), 7.82(s, 1 H), 7.24(m, 1 H), 6.83(m, 2 H), 5.43(q, 1 H), 4.76(d, 1 H, J = 14.2 Hz), 3.75(d, 1 H, J = 14.1 Hz), 2.74(s, 3 H), 2.55(s, 3 H), 1.42(d, 3 H, J = 6.8 Hz) |
| 129 | 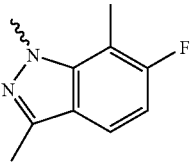 | 8.37(s, 1 H), 8.23(m, 2 H), 7.88(m, 2 H), 6.89(m, 2 H), 6.05(br, 1 H), 5.51(q, 1 H), 4.58(d, 1 H, J = 14.2 Hz), 3.47(d, 1 H, J = 14.2 Hz), 2.81(s, 3 H), 2.56(s, 3 H), 1.41(d, 3 H, J = 6.8 Hz) |
| 130 | 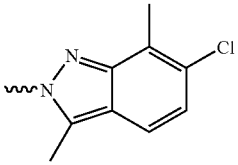 | 8.21(s, 1 H), 8.05(m, 2 H), 7.82(s, 1 H), 7.24(m, 1 H), 6.83(m, 2 H), 5.43(q, 1 H), 4.76(d, 1 H, J = 14.2 Hz), 3.75(d, 1 H, J = 14.1 Hz), 2.74(s, 3 H), 2.48(s, 3 H), 1.42(d, 3 H, J = 6.8 Hz) |
| 131 | 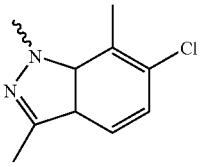 | 8.23(s, 1 H), 8.13(m, 2 H), 7.86(m, 2 H), 6.89(m, 2 H), 6.05(br, 1 H), 5.51(q, 1 H), 4.68(d, 1 H, J = 14.2 Hz), 3.47(d, 1 H, J = 14.2 Hz), 2.81(s, 3 H), 2.48(s, 3 H), 1.40(d, 3 H, J = 6.8 Hz) |
| 132 | 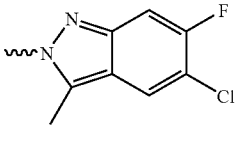 | 8.23(s, 1 H), 8.09(m, 2 H), 7.82(s, 1 H), 7.24(m, 1 H), 6.83(m, 2 H), 5.43(q, 1 H), 4.76(d, 1 H, J = 14.2 Hz), 3.75(d, 1 H, J = 14.1 Hz), 2.74(s, 3 H), 1.44(d, 3 H, J = 6.8 Hz) |

TABLE 5-continued

| Ex. | Het | $^{1}$H-NMR(300 MHz, CDCl$_3$) δ |
|---|---|---|
| 133 | 6-F, 5-Cl-1H-indazol-3-methyl (N1-linked) | 8.29(s, 1 H), 8.11(m, 2 H), 7.86(m, 2 H), 6.89(m, 2 H), 6.05(br, 1 H), 5.51(q, 1 H), 4.68(d, 1 H, J = 14.2 Hz), 3.47(d, 1 H, J = 14.2 Hz), 2.79(s, 3 H), 1.42(d, 3 H, J = 6.8 Hz) |
| 134 | 6-F, 5-Me-3-methyl-2H-indazole (N2-linked) | 8.23(s, 1 H), 8.02(m, 2 H), 7.82(s, 1 H), 7.24(m, 1 H), 6.83(m, 2 H), 5.43(q, 1 H), 4.76(d, 1 H, J = 14.2 Hz), 3.75(d, 1 H, J = 14.1 Hz), 2.74(s, 3 H), 2.55(s, 3 H), 1.43(d, 3 H, J = 6.8 Hz) |
| 135 | 6-F, 5-Me-3-methyl-1H-indazole (N1-linked) | 8.27(s, 1 H), 8.15(m, 2 H), 7.89(m, 2 H), 6.89(m, 2 H), 6.05(br, 1 H), 5.51(q, 1 H), 4.58(d, 1 H, J = 14.2 Hz), 3.47(d, 1 H, J = 14.2 Hz), 2.81(s, 3 H), 2.61(s, 3 H), 1.41(d, 3 H, J = 6.8 Hz) |
| 136 | 6-Cl, 5-Me-3-methyl-2H-indazole (N2-linked) | 8.24(s, 1 H), 8.02(m, 1 H), 7.82(s, 1 H), 7.24(m, 2 H), 6.83(m, 2 H), 5.43(q, 1 H), 4.76(d, 1 H, J = 14.2 Hz), 3.75(d, 1 H, J = 14.1 Hz), 2.74(s, 3 H), 2.54(s, 3 H), 1.41(d, 3 H, J = 6.8 Hz) |
| 137 | 6-Cl, 5-Me-3-methyl-1H-indazole (N1-linked) | 8.27(s, 1 H), 8.15(m, 2 H), 7.89(m, 2 H), 6.89(m, 2 H), 6.03(br, 1 H), 5.51(q, 1 H), 4.58(d, 1 H, J = 14.2 Hz), 3.47(d, 1 H, J = 14.2 Hz), 2.81(s, 3 H), 2.61(s, 3 H), 1.39(d, 3 H, J = 6.8 Hz) |
| 138 | 7-F, 5-NO$_2$-3-methyl-2H-indazole (N2-linked) | 8.25(s, 1 H), 8.02(m, 2 H), 7.82(s, 1 H), 7.24(m, 1 H), 6.83(m, 2 H), 5.43(q, 1 H), 4.78(d, 1 H, J = 14.2 Hz), 3.75(d, 1 H, J = 14.1 Hz), 2.74(s, 3 H), 1.38(d, 3 H, J = 6.8 Hz) |
| 139 | 7-F, 5-NO$_2$-3-methyl-1H-indazole (N1-linked) | 8.27(s, 1 H), 8.15(m, 2 H), 7.89(m, 2 H), 6.89(m, 2 H), 6.05(br, 1 H), 5.51(q, 1 H), 4.58(d, 1 H, J = 14.2 Hz), 3.47(d, 1 H, J = 14.2 Hz), 2.81(s, 3 H), 1.36(d, 3 H, J = 6.8 Hz) |
| 140 | 5,7-diF-3-methyl-2H-indazole (N2-linked) | 8.18(s, 1 H), 8.10(m, 2 H), 7.82(s, 1 H), 7.24(m, 1 H), 6.83(m, 2 H), 5.43(q, 1 H), 4.76(d, 1 H, J = 14.2 Hz), 3.75(d, 1 H, J = 14.1 Hz), 2.74(s, 3 H), 1.43(d, 3 H, J = 6.8 Hz) |
| 141 | 5,7-diF-3-methyl-1H-indazole (N1-linked) | 8.18(s, 1 H), 8.15(m, 2 H), 7.89(m, 2 H), 6.89(m, 2 H), 6.05(br, 1 H), 5.51(q, 1 H), 4.58(d, 1 H, J = 14.2 Hz), 3.47(d, 1 H, J = 14.2 Hz), 2.81(s, 3 H), 1.42(d, 3 H, J = 6.9 Hz) |

TABLE 5-continued

| Ex. | Het | ¹H-NMR(300 MHz, CDCl₃) δ |
|---|---|---|
| 142 | 3-methyl-5-chloro-7-fluoro-2H-indazol-2-yl | 8.25(s, 1 H), 8.02(m, 2 H), 7.82(s, 1 H), 7.24(m, 1 H), 6.83(m, 2 H), 5.43(q, 1 H), 4.78(d, 1 H, J = 14.2 Hz), 3.75(d, 1 H, J = 14.1 Hz), 2.74(s, 3 H), 1.31(d, 3 H, J = 6.8 Hz) |
| 143 | 3-methyl-5-chloro-7-fluoro-1H-indazol-1-yl | 8.27(s, 1 H), 8.15(m, 2 H), 7.89(m, 2 H), 6.89(m, 2 H), 6.05(br, 1 H), 5.51(q, 1 H), 4.58(d, 1 H, J = 14.2 Hz), 3.47(d, 1 H, J = 14.2 Hz), 2.81(s, 3 H), 1.30(d, 3 H, J = 6.8 Hz) |
| 144 | 3-methyl-5-fluoro-7-chloro-2H-indazol-2-yl | 8.21(s, 1 H), 8.10(m, 2 H), 7.82(s, 1 H), 7.24(m, 1 H), 6.83(m, 2 H), 5.43(q, 1 H), 4.76(d, 1 H, J = 14.2 Hz), 3.75(d, 1 H, J = 14.1 Hz), 2.74(s, 3 H), 1.43(d, 3 H, J = 6.8 Hz) |
| 145 | 3-methyl-5-fluoro-7-chloro-1H-indazol-1-yl | 8.19(s, 1 H), 8.13(m, 2 H), 7.89(m, 2 H), 6.89(m, 2 H), 6.05(br, 1 H), 5.51(q, 1 H), 4.58(d, 1 H, J = 14.2 Hz), 3.47(d, 1 H, J = 14.2 Hz), 2.81(s, 3 H), 1.41(d, 3 H, J = 6.9 Hz) |
| 146 | 3-methyl-5,7-dichloro-2H-indazol-2-yl | 8.11(s, 1 H), 7.84(m, 2 H), 7.72(s, 1 H), 7.24(m, 2 H), 6.83(m, 2 H), 5.33(q, 1 H), 4.76(d, 1 H, J = 14.2 Hz), 3.75(d, 1 H, J = 14.1 Hz), 2.74(s, 3 H), 1.42(d, 3 H, J = 6.8 Hz) |
| 147 | 3-methyl-5,7-dichloro-1H-indazol-1-yl | 8.15(s, 1 H), 8.01(m, 2 H), 7.80(m, 2 H), 6.79(m, 2 H), 5.98(br, 1 H), 5.51(q, 1 H), 4.58(d, 1 H, J = 14.2 Hz), 3.47(d, 1 H, J = 14.2 Hz), 2.81(s, 3 H), 1.39(d, 3 H, J = 6.8 Hz) |
| 148 | 3,7-dimethyl-5-fluoro-2H-indazol-2-yl | 8.15(s, 1 H), 7.84(m, 2 H), 7.72(s, 1 H), 7.24(m, 1 H), 6.83(m, 2 H), 5.31(q, 1 H), 4.76(d, 1 H, J = 14.2 Hz), 3.75(d, 1 H, J = 14.1 Hz), 2.74(s, 3 H), 2.55(s, 3 H), 1.45(d, 3 H, J = 6.8 Hz) |
| 149 | 3,7-dimethyl-5-fluoro-1H-indazol-1-yl | 8.16(s, 1 H), 8.03(m, 2 H), 7.80(m, 2 H), 6.79(m, 2 H), 5.98(br, 1 H), 5.51(q, 1 H), 4.58(d, 1 H, J = 14.2 Hz), 3.47(d, 1 H, J = 14.2 Hz), 2.81(s, 3 H), 2.65(s, 3 H), 1.47(d, 3 H, J = 6.8 Hz) |

TABLE 5-continued

| Ex. | Het | ¹H-NMR(300 MHz, CDCl₃) δ |
| --- | --- | --- |
| 150 | 7-methyl-5-chloro-3-methyl-2H-indazol-2-yl | 8.13(s, 1 H), 7.98(m, 2 H), 7.90(s, 1 H), 7.84(m, 1 H), 6.83(m, 2 H), 5.43(q, 1 H), 4.86(d, 1 H, J = 14.2 Hz), 3.75(d, 1 H, J = 14.1 Hz), 2.74(s, 3 H), 2.65(s, 3 H), 1.37(d, 3 H, J = 6.8 Hz) |
| 151 | 7-methyl-5-chloro-3-methyl-1H-indazol-1-yl | 8.18(s, 1 H), 8.05(m, 2 H), 7.79(m, 2 H), 6.79(m, 2 H), 6.02(br, 1 H), 5.51(q, 1 H), 4.58(d, 1 H, J = 14.2 Hz), 3.47(d, 1 H, J = 14.2 Hz), 2.81(s, 3 H), 2.61(s, 3 H), 1.36(d, 3 H, J = 6.8 Hz) |
| 152 | 6-methyl-5-fluoro-3-methyl-2H-indazol-2-yl | 8.31(s, 1 H), 7.99(m, 2 H), 7.93(s, 1 H), 7.84(m, 1 H), 6.83(m, 2 H), 5.43(q, 1 H), 4.86(d, 1 H, J = 14.2 Hz), 3.75(d, 1 H, J = 14.1 Hz), 2.74(s, 3 H), 2.54(s, 3 H), 1.43(d, 3 H, J = 6.8 Hz) |
| 153 | 6-methyl-5-fluoro-3-methyl-1H-indazol-1-yl | 8.33(s, 1 H), 8.01(m, 2 H), 7.90(s, 1 H), 7.84(m, 1 H), 6.83(m, 2 H), 6.03(br, 1 H), 5.51(q, 1 H), 4.58(d, 1 H, J = 14.2 Hz), 3.47(d, 1 H, J = 14.2 Hz), 2.81(s, 3 H), 2.61(s, 3 H), 1.42(d, 3 H, J = 6.8 Hz) |
| 154 | 6-methyl-5-chloro-3-methyl-2H-indazol-2-yl | 8.11(s, 1 H), 7.98(m, 2 H), 7.90(s, 1 H), 7.84(m, 1 H), 6.83(m, 2 H), 5.43(q, 1 H), 4.86(d, 1 H, J = 14.2 Hz), 3.75(d, 1 H, J = 14.1 Hz), 2.74(s, 3 H), 2.55(s, 3 H), 1.43(d, 3 H, J = 6.8 Hz) |
| 155 | 6-methyl-5-chloro-3-methyl-1H-indazol-1-yl | 8.12(s, 1 H), 8.03(m, 2 H), 7.85(m, 2 H), 6.79(m, 2 H), 6.02(br, 1 H), 5.51(q, 1 H), 4.58(d, 1 H, J = 14.2 Hz), 3.47(d, 1 H, J = 14.2 Hz), 2.81(s, 3 H), 2.61(s, 3 H), 1.42(d, 3 H, J = 6.8 Hz) |
| 156 | 5-bromo-3-methyl-2H-indazol-2-yl | 8.05(s, 1 H), 7.81(m, 2 H), 7.68(s, 1 H), 7.24(m, 2 H), 6.83(m, 2 H), 5.33(q, 1 H), 4.76(d, 1 H, J = 14.2 Hz), 3.75(d, 1 H, J = 14.1 Hz), 2.74(s, 3 H), 1.33(d, 3 H, J = 6.8 Hz) |
| 157 | 5-bromo-3-methyl-1H-indazol-1-yl | 8.08(s, 1 H), 7.98(m, 2 H), 7.85(m, 3 H), 6.79(m, 2 H), 6.02(br, 1 H), 5.51(q, 1 H), 4.58(d, 1 H, J = 14.2 Hz), 3.47(d, 1 H, J = 14.2 Hz), 2.81(s, 3 H), 1.31(d, 3 H, J = 6.8 Hz) |
| 158 | 6-bromo-3-methyl-2H-indazol-2-yl | 8.01(s, 1 H), 7.78(m, 2 H), 7.68(s, 1 H), 7.24(m, 2 H), 6.83(m, 2 H), 5.33(q, 1 H), 4.76(d, 1 H, J = 14.2 Hz), 3.75(d, 1 H, J = 14.1 Hz), 2.74(s, 3 H), 1.33(d, 3 H, J = 6.8 Hz) |
| 159 | 6-bromo-3-methyl-1H-indazol-1-yl | 8.10(s, 1 H), 8.03(m, 2 H), 7.85(m, 3 H), 6.79(m, 2 H), 6.02(br, 1 H), 5.51(q, 1 H), 4.58(d, 1 H, J = 14.2 Hz), 3.47(d, 1 H, J = 14.2 Hz), 2.81(s, 3 H), 1.31(d, 3 H, J = 6.8 Hz) |

TABLE 5-continued

| Ex. | Het | ¹H-NMR(300 MHz, CDCl₃) δ |
|---|---|---|
| 160 | 3-methyl-1H-indazol-2-yl with 5-CN | 8.08(s, 1 H), 7.91(m, 2 H), 7.78(s, 1 H), 7.31(m, 2 H), 6.91(m, 2 H), 5.41(q, 1 H), 4.76(d, 1 H, J = 14.2 Hz), 3.75(d, 1 H, J = 14.1 Hz), 2.74(s, 3 H), 1.37(d, 3 H, J = 6.8 Hz) |
| 161 | 3-methyl-1H-indazol-1-yl with 5-CN | 8.13(s, 1 H), 8.03(m, 2 H), 7.85(m, 3 H), 6.96(m, 2 H), 6.12(br, 1 H), 5.51(q, 1 H), 4.58(d, 1 H, J = 14.2 Hz), 3.47(d, 1 H, J = 14.2 Hz), 2.80(s, 3 H), 1.35(d, 3 H, J = 6.8 Hz) |
| 162 | 3-methyl-7-bromo-1H-indazol-1-yl | 8.03(s, 1 H), 7.84(m, 2 H), 7.68(s, 1 H), 7.24(m, 2 H), 6.83(m, 2 H), 5.33(q, 1 H), 4.76(d, 1 H, J = 14.2 Hz), 3.75(d, 1 H, J = 14.1 Hz), 2.74(s, 3 H), 1.35(d, 3 H, J = 6.8 Hz) |
| 163 | 3-methyl-7-bromo-1H-indazol-2-yl | 8.10(s, 1 H), 8.03(m, 1 H), 7.85(m, 4 H), 6.79(m, 2 H), 5.98(br, 1 H), 5.51(q, 1 H), 4.58(d, 1 H, J = 14.2 Hz), 3.47(d, 1 H, J = 14.2 Hz), 2.81(s, 3 H), 1.33(d, 3 H, J = 6.9 Hz) |
| 164 | 3-ethyl-7-nitro-1H-indazol-2-yl | 8.13(s, 1 H), 7.94(m, 1 H), 7.72(s, 1 H), 7.24(m, 3 H), 6.83(m, 2 H), 5.33(q, 1 ), 4.76(d, 1 H, J = 14.2 Hz), 3.76(d, 1 H, J = 14.1 Hz), 3.68(q, 2 H), 1.53(t, 3 H), 1.42(d, 3 H, J = 6.8 Hz) |
| 165 | 3-ethyl-7-nitro-1H-indazol-1-yl | 8.18(s, 1 H), 8.03(m, 1 H), 7.80(m, 4 H), 6.79(m, 2 H), 5.98(br, 1 H), 5.51(q, 1 H), 4.58(d, 1 H, J = 14.2 Hz), 3.45(d, 1 H, J = 14.2 Hz), 3.45(q, 2 H), 1.52(t, 3 H), 1.40(d, 3 H, J = 6.8 Hz) |
| 166 | 3-ethyl-7-fluoro-1H-indazol-2-yl | 8.10(s, 1 H), 7.88(m, 2 H), 7.75(s, 1 H), 7.20(m, 2 H), 6.81(m, 2 H), 5.23(q, 1 H), 4.71(d, 1 H, J = 14.2 Hz), 3.88(d, 1 H, J = 14.1 Hz), 3.28(q, 2 H), 1.41(t, 3 H), 1.36(d, 3 H, J = 6.8 Hz) |
| 167 | 3-ethyl-7-fluoro-1H-indazol-1-yl | 8.10(s, 1 H), 8.03(m, 2 H), 7.78(m, 3 H), 6.89(m, 2 H), 5.80(br, 1 H), 5.31(q, 1 H), 4.58(d, 1 H, J = 14.2 Hz), 3.65(d, 1 H, J = 14.2 Hz), 3.35(q, 2 H), 1.42(t, 3 H), 1.34(d, 3 H, J = 6.8 Hz) |

TABLE 5-continued

| Ex. | Het | $^1$H-NMR(300 MHz, CDCl$_3$) δ |
|---|---|---|
| 168 | 7-chloro-3-ethyl-2H-indazole | 8.12(s, 1 H), 7.97(m, 1 H), 7.85(s, 1 H), 7.21(m, 3 H), 6.84(m, 2 H), 5.43(q, 1 H), 4.71(d, 1 H, J = 14.2 Hz), 3.88(d, 1 H, J = 14.1 Hz), 3.28(q, 2 H), 1.41(t, 3 H), 1.36(d, 3 H, J = 6.8 Hz) |
| 169 | 7-chloro-3-ethyl-1H-indazole | 8.10(s, 1 H), 8.03(m, 1 H), 7.78(m, 4 H), 6.89(m, 2 H), 5.90(br, 1 H), 5.38(q, 1 H), 4.58(d, 1 H, J = 14.2 Hz), 3.79(d, 1 H, J = 14.2 Hz), 3.35(q, 2 H), 1.42(t, 3 H), 1.33(d, 3 H, J = 6.8 Hz) |
| 170 | 5-bromo-3-ethyl-7-fluoro-2H-indazole | 8.13(s, 1 H), 7.94(m, 2 H), 7.72(s, 1 H), 7.24(m, 1 H), 6.83(m, 2 H), 5.33(q, 1 H), 4.76(d, 1 H, J = 14.2 Hz), 3.76(d, 1 H, J = 14.1 Hz), 3.68(q, 2 H), 1.53(t, 3 H), 1.42(d, 3 H, J = 6.8 Hz) |
| 171 | 5-bromo-3-ethyl-7-fluoro-1H-indazole | 8.18(s, 1 H), 8.03(m, 2 H), 7.80(m, 2 H), 6.79(m, 2 H), 5.98(br, 1 H), 5.51(q, 1 H), 4.58(d, 1 H, J = 14.2 Hz), 3.45(d, 1 H, J = 14.2 Hz), 3.45(q, 2 H), 1.52(t, 3 H), 1.40(d, 3H, J = 6.8 Hz) |
| 172 | 5-bromo-7-chloro-3-ethyl-2H-indazole | 8.10(s, 1 H), 7.88(m, 2 H), 7.75(s, 1 H), 7.20(m, 1 H), 6.81(m, 2 H), 5.23(q, 1 H), 4.71(d, 1 H, J = 14.2 Hz), 3.88(d, 1 H, J = 14.1 Hz), 3.28(q, 2 H), 1.41(t, 3 H), 1.36(d, 3 H, J = 6.8 Hz) |
| 173 | 5-bromo-7-chloro-3-ethyl-1H-indazole | 8.10(s, 1 H), 8.03(m, 2 H), 7.78(m, 2 H), 6.89(m, 2 H), 5.80(br, 1 H), 5.31(q, 1 H), 4.58(d, 1 H, J = 14.2 Hz), 3.65(d, 1 H, J = 14.2 Hz), 3.35(q, 2 H), 1.42(t, 3H), 1.34(d, 3 H, J = 6.8 Hz) |
| 174 | 3-ethyl-7-fluoro-5-methyl-2H-indazole | 8.32(s, 1 H), 7.97(m, 1 H), 7.85(s, 1 H), 7.21(m, 1 H), 6.85(m, 2 H), 5.43(q, 1 H), 4.71(d, 1 H, J = 14.2 Hz), 3.88(d, 1 H, J = 14.1 Hz), 3.28(q, 2 H), 2.35(s, 3H), 1.41(t, 3 H), 1.41(d, 3 H, J = 6.8 Hz) |

TABLE 5-continued

| Ex. | Het | ¹H-NMR(300 MHz, CDCl₃) δ |
|---|---|---|
| 175 | 7-F, 5-methyl-3-ethyl-2H-indazole | 8.30(s, 1H), 8.03(m, 1 H), 7.78(m, 2 H), 6.89(m, 2 H), 5.90(br, 1 H), 5.38(q, 1 H), 4.58(d, 1 H, J = 14.2 Hz), 3.79(d, 1 H, J = 14.2 Hz), 3.35(q, 2 H), 2.22(s, 3H), 1.42(t, 3 H), 1.43(d, 3 H, J = 6.8 Hz) |
| 176 | 7-Cl, 5-methyl-3-ethyl-2H-indazole | 8.22(s, 1 H), 8.02(m, 1 H), 7.85(s, 1 H), 7.21(m, 1 H), 6.85(m, 2 H), 5.43(q, 1 H), 4.71(d, 1 H, J = 14.2 Hz), 3.88(d, 1 H, J = 14.1 Hz), 3.28(q, 2 H), 2.35(s, 3 H), 1.41(t, 3 H), 1.41(d, 3 H, J = 6.8 Hz) |
| 177 | 7-Cl, 5-methyl-3-ethyl-1H-indazole | 8.25(s, 1 H), 8.03(m, 1 H), 7.78(m, 2 H), 6.89(m, 2 H), 5.90(br, 1 H), 5.38(q, 1 H), 4.58(d, 1 H, J = 14.2 Hz), 3.79(d, 1 H, J = 14.2 Hz), 3.35(q, 2 H), 2.25(s, 3 H), 1.42(t, 3 H), 1.43(d, 3 H, J = 6.8 Hz) |
| 178 | 6-NO₂, 3-ethyl-2H-indazole | 8.15(s, 1 H), 7.98(m, 2 H), 7.90(s, 1 H), 7.84(m, 2 H), 6.83(m, 2 H), 5.74(br, 1 H), 5.43(q, 1 H), 4.86(d, 1 H, J = 14.2 Hz), 3.75(d, 1 H, J = 14.1 Hz), 3.05(q, 2 H), 1.58(t, 3 H), 1.41(d, 3 H, J = 6.8 Hz) |
| 179 | 6-NO₂, 3-ethyl-1H-indazole | 8.13(s, 1 H), 8.01(m, 2 H), 7.90(s, 1 H), 7.84(m, 1 H), 6.83(m, 2 H), 6.01(br, 1 H) 5.74(br, 1 H), 5.43(q, 1 H), 4.86(d, 1 H, J = 14.2 Hz), 3.57(d, 1 H, J = 14.1 Hz), 3.11(q, 2 H), 1.51(t, 3 H), 1.40(d, 3 H, J = 6.8 Hz) |
| 180 | 6-Cl, 3-ethyl-2H-indazole | 8.10(s, 1 H), 7.88(m, 2 H), 7.75(s, 1 H), 7.20(m, 2 H), 6.81(m, 2 H), 5.23(q, 1 H), 4.71(d, 1 H, J = 14.2 Hz), 3.88(d, 1 H, J = 14.1 Hz), 3.28(q, 2 H), 1.41(t, 3 H), 1.36(d, 3 H, J = 6.8 Hz) |
| 181 | 6-Cl, 3-ethyl-1H-indazole | 8.10(s, 1 H), 8.03(m, 2 H), 7.78(m, 3 H), 6.89(m, 2H), 5.80(br, 1 H), 5.31(q, 1 H), 4.58(d, 1 H, J = 14.2 Hz), 3.65(d, 1 H, J = 14.2 Hz), 3.35(q, 2 H), 1.42(t, 3 H), 1.34(d, 3 H, J = 6.8 Hz) |

TABLE 5-continued

| Ex. | Het | $^1$H-NMR(300 MHz, CDCl$_3$) δ |
|---|---|---|
| 182 | (2-indazolyl, 7-methyl-6-fluoro, 3-ethyl) | 8.15(s, 1 H), 7.88(m, 2 H), 7.75(s, 1 H), 7.20(m, 1 H), 6.81(m, 2 H), 5.23(q, 1 H), 4.71(d, 1 H, J = 14.2 Hz), 3.88(d, 1 H, J = 14.1 Hz), 3.28(q, 2 H), 2.51(s, 3 H), 1.41(t, 3 H), 1.36(d, 3 H, J = 6.8 Hz) |
| 183 | (1-indazolyl, 7-methyl-6-fluoro, 3-ethyl) | 8.19(s, 1 H), 8.03(m, 2 H), 7.78(m, 2 H), 6.89(m, 2 H), 5.80(br, 1 H), 5.31(q, 1 H), 4.58(d, 1 H, J = 14.2 Hz), 3.65(d, 1 H, J = 14.2 Hz), 3.35(q, 2 H), 2.53(s, 3 H), 1.42(t, 3 H), 1.34(d, 3 H, J = 6.8 Hz) |
| 184 | (2-indazolyl, 7-methyl-6-chloro, 3-ethyl) | 8.20(s, 1 H), 7.88(m, 2 H), 7.75(s, 1 H), 7.20(m, 1 H), 6.81(m, 2 H), 5.23(q, 1 H), 4.71(d, 1 H, J = 14.2 Hz), 3.88(d, 1 H, J = 14.1 Hz), 3.28(q, 2 H), 2.31(s, 3 H), 1.41(t, 3 H), 1.36(d, 3 H, J = 6.8 Hz) |
| 185 | (1-indazolyl, 7-methyl-6-chloro, 3-ethyl) | 8.20(s, 1 H), 8.03(m, 2 H), 7.78(m, 2 H), 6.89(m, 2 H), 5.80(br, 1 H), 5.31(q, 1 H), 4.58(d, 1 H, J = 14.2 Hz), 3.65(d, 1 H, J = 14.2 Hz), 3.35(q, 2 H), 2.33(s, 3 H), 1.42(t, 3 H), 1.34(d, 3 H, J = 6.8 Hz) |
| 186 | (2-indazolyl, 6-fluoro-5-chloro, 3-ethyl) | 8.13(s, 1 H), 7.88(m, 1 H), 7.75(s, 1 H), 7.20(m, 2 H), 6.81(m, 2 H), 5.23(q, 1 H), 4.71(d, 1 H, J = 14.2 Hz), 3.88(d, 1 H, J = 14.1 Hz), 3.28(q, 2 H), 1.41(t, 3 H), 1.36(d, 3 H, J = 6.8 Hz) |
| 187 | (1-indazolyl, 6-fluoro-5-chloro, 3-ethyl) | 8.11(s, 1 H), 8.03(m, 2 H), 7.78(m, 2 H), 6.89(m, 2 H), 5.80(br, 1 H), 5.31(q, 1 H), 4.58(d, 1 H, J = 14.2 Hz), 3.65(d, 1 H, J = 14.2 Hz), 3.35(q, 2 H), 1.42(t, 3 H), 1.34(d, 3 H, J = 6.8 Hz) |
| 188 | (2-indazolyl, 6,5-dichloro, 3-ethyl) | 8.13(s, 1 H), 7.88(m, 2 H), 7.75(s, 1 H), 7.20(m, 1 H), 6.81(m, 2 H), 5.23(q, 1 H), 4.71(d, 1 H, J = 14.2 Hz), 3.88(d, 1 H, J = 14.1 Hz), 3.28(q, 2 H), 1.41(t, 3 H), 1.36(d, 3 H, J = 6.8 Hz) |

TABLE 5-continued

| Ex. | Het | $^{1}$H-NMR(300 MHz, CDCl$_3$) δ |
|---|---|---|
| 189 | 5,6-dichloro-3-ethyl-1H-indazol-1-yl | 8.11(s, 1 H), 8.03(m, 2 H), 7.78(m, 2 H), 6.89(m, 2 H), 5.80(br, 1 H), 5.31(q, 1 H), 4.58(d, 1 H, J = 14.2 Hz), 3.65(d, 1 H, J = 14.2 Hz), 3.35(q, 2 H), 1.42(t, 3 H), 1.34(d, 3 H, J = 6.8 Hz) |
| 190 | 6-fluoro-5-methyl-3-ethyl-2H-indazol-2-yl | 8.15(s, 1 H), 7.88(m, 2 H), 7.75(s, 1 H), 7.20(m, 1 H), 6.81(m, 2 H), 5.23(q, 1 H), 4.71(d, 1 H, J = 14.2 Hz), 3.88(d, 1 H, J = 14.1 Hz), 3.28(q, 2 H), 2.51(s, 3 H), 1.41(t, 3 H), 1.36(d, 3 H, J = 6.8 Hz) |
| 191 | 6-fluoro-5-methyl-3-ethyl-1H-indazol-1-yl | 8.19(s, 1 H), 8.03(m, 2 H), 7.78(m, 2 H), 6.89(m, 2 H), 5.80(br, 1 H), 5.31(q, 1 H), 4.58(d, 1 H, J = 14.2 Hz), 3.65(d, 1 H, J = 14.2 Hz), 3.35(q, 2 H), 2.53(s, 3 H), 1.42(t, 3 H), 1.34(d, 3 H, J = 6.8 Hz) |
| 192 | 6-chloro-5-methyl-3-ethyl-2H-indazol-2-yl | 8.18(s, 1 H), 7.89(m, 2 H), 7.75(s, 1 H), 7.20(m, 1 H), 6.81(m, 2 H), 5.23(q, 1 H), 4.71(d, 1 H, J = 14.2 Hz), 3.88(d, 1 H, J = 14.1 Hz), 3.28(q, 2 H), 2.51(s, 3 H), 1.41(t, 3 H), 1.36(d, 3 H, J = 6.8 Hz) |
| 193 | 6-chloro-5-methyl-3-ethyl-1H-indazol-1-yl | 8.20(s, 1 H), 8.01(m, 2 H), 7.78(m, 2 H), 6.89(m, 2 H), 5.80(br, 1 H), 5.31(q, 1H), 4.58(d, 1H, J = 14.2 Hz), 3.65(d, 1 H, J = 14.2 Hz), 3.35(q, 2 H), 2.53(s, 3 H), 1.42(t, 3 H), 1.35(d, 3 H, J = 6.8 Hz) |
| 194 | 5-nitro-3-ethyl-2H-indazol-2-yl | 8.13(s, 1 H), 7.94(m, 2 H), 7.75(s, 1 H), 7.44(m, 2 H), 6.83(m, 2 H), 5.33(q, 1 H), 4.76(d, 1 H, J = 14.2 Hz), 3.76(d, 1 H, J = 14.1 Hz), 3.68(q, 2 H), 1.53(t, 3 H), 1.42(d, 3 H, J = 6.8 Hz) |
| 195 | 5-nitro-3-ethyl-1H-indazol-1-yl | 8.18(s, 1 H), 8.03(m, 2 H), 7.80(m, 2 H), 6.79(m, 2 H), 5.98(br, 1 H), 5.51(q, 1 H), 4.58(d, 1 H, J = 14.2 Hz), 3.45(d, 1 H, J = 14.2 Hz), 3.45(q, 2 H), 1.52(t, 3 H), 1.41(d, 3 H, J = 6.8 Hz) |
| 196 | 5-chloro-3-ethyl-2H-indazol-2-yl | 8.09(s, 1 H), 7.88(m, 2 H), 7.72(s, 1 H), 7.24(m, 1 H), 6.83(m, 2 H), 5.33(q, 1 H), 4.76(d, 1 H, J = 14.2 Hz), 3.76(d, 1 H, J = 14.1 Hz), 3.68(q, 2 H), 1.53(t, 3 H), 1.38(d, 3 H, J = 6.8 Hz) |

TABLE 5-continued
| Ex. | Het | $^1$H-NMR(300 MHz, CDCl$_3$) δ |
|---|---|---|
| 197 | 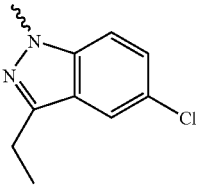 | 8.12(s, 1 H), 7.98(m, 2 H), 7.80(m, 2 H), 6.79(m, 2 H), 5.98(br, 1 H), 5.51(q, 1 H), 4.58(d, 1 H, J = 14.2 Hz), 3.45(d, 1 H, J = 14.2 Hz), 3.45(q, 2 H), 1.52(t, 3 H), 1.36(d, 3 H, J = 6.8 Hz) |
| 198 | 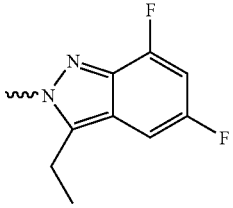 | 8.11(s, 1 H), 7.85(m, 2 H), 7.75(s, 1 H), 7.20(m, 1 H), 6.81(m, 2 H), 5.23(q, 1 H), 4.71(d, 1 H, J = 14.2 Hz), 3.88(d, 1 H, J = 14.1 Hz), 3.28(q, 2 H), 1.41(t, 3 H), 1.37(d, 3 H, J = 6.8 Hz) |
| 199 | 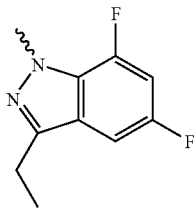 | 8.11(s, 1 H), 8.03(m, 2 H), 7.78(m, 2 H), 6.89(m, 2 H), 5.80(br, 1 H), 5.31(q, 1 H), 4.58(d, 1 H, J = 14.2 Hz), 3.65(d, 1 H, J = 14.2 Hz), 3.35(q, 2 H), 1.42(t, 3 H), 1.35(d, 3 H, J = 6.8 Hz) |
| 200 | 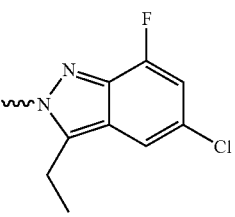 | 8.09(s, 1 H), 7.91(m, 2 H), 7.78(s, 1 H), 7.20(m, 1 H), 6.81(m, 2 H), 5.23(q, 1 H), 4.71(d, 1 H, J = 14.2 Hz), 3.88(d, 1 H, J = 14.1 Hz), 3.28(q, 2 H), 1.41(t, 3 H), 1.37(d, 3 H, J = 6.8 Hz) |
| 201 | 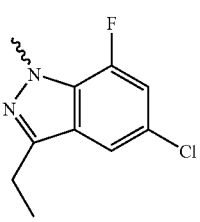 | 8.11(s, 1 H), 8.03(m, 2 H), 7.80(m, 2 H), 6.89(m, 2 H), 5.80(br, 1 H), 5.31(q, 1 H), 4.58(d, 1 H, J = 14.2 Hz), 3.65(d, 1 H, J = 14.2 Hz), 3.35(q, 2 H), 1.42(t, 3 H), 1.35(d, 3 H, J = 6.8 Hz) |
| 202 | 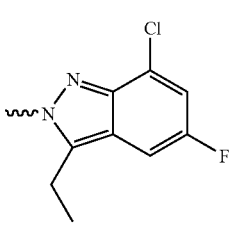 | 8.15(s, 1 H), 7.95(m, 2 H), 7.75(s, 1 H), 7.20(m, 1 H), 6.81(m, 2 H), 5.23(q, 1 H), 4.71(d, 1 H, J = 14.2 Hz), 3.88(d, 1 H, J = 14.1 Hz), 3.28(q, 2 H), 1.41(t, 3 H), 1.35(d, 3 H, J = 6.8 Hz) |
| 203 | 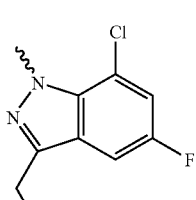 | 8.18(s, 1 H), 8.03(m, 2 H), 7.78(m, 2 H), 6.89(m, 2 H), 5.80(br, 1 H), 5.31(q, 1 H), 4.58(d, 1 H, J = 14.2 Hz), 3.65(d, 1 H, J = 14.2 Hz), 3.35(q, 2 H), 1.40(t, 3 H), 1.33(d, 3 H, J = 6.8 Hz) |

TABLE 5-continued

| Ex. | Het | $^1$H-NMR(300 MHz, CDCl$_3$) δ |
|---|---|---|
| 204 | 7-Cl, 5-Cl, 3-ethyl-2H-indazol-2-yl | 8.09(s, 1 H), 7.91(m, 2 H), 7.78(s, 1 H), 7.20(m, 1 H), 6.81(m, 2 H), 5.23(q, 1 H), 4.71(d, 1 H, J = 14.2 Hz), 3.88(d, 1 H, J = 14.1 Hz), 3.28(q, 2 H), 1.41(t, 3 H), 1.37(d, 3 H, J = 6.8 Hz) |
| 205 | 7-Cl, 5-Cl, 3-ethyl-1H-indazol-1-yl | 8.13(s, 1 H), 8.03(m, 2 H), 7.80(m, 2 H), 6.89(m, 2 H), 5.80(br, 1 H), 5.31(q, 1 H), 4.48(d, 1 H, J = 14.2 Hz), 3.65(d, 1 H, J = 14.2 Hz), 3.35(q, 2 H), 1.42(t, 3 H), 1.36(d, 3 H, J = 6.8 Hz) |
| 206 | 7-methyl, 5-F, 3-ethyl-2H-indazol-2-yl | 8.11(s, 1 H), 7.85(m, 2 H), 7.75(s, 1 H), 7.20(m, 1 H), 6.81(m, 2 H), 5.23(q, 1 H), 4.71(d, 1 H, J = 14.2 Hz), 3.88(d, 1 H, J = 14.1 Hz), 3.28(q, 2 H), 2.56(s, 3 H), 1.41(t, 3 H), 1.37(d, 3 H, J = 6.8 Hz) |
| 207 | 7-methyl, 5-F, 3-ethyl-1H-indazol-1-yl | 8.11(s, 1 H), 8.03(m, 2H), 7.78(m, 2 H), 6.89(m, 2 H), 5.80(br, 1 H), 5.31(q, 1 H), 4.58(d, 1 H, J = 14.2 Hz), 3.65(d, 1 H, J = 14.2 Hz), 3.35(q, 2 H), 2.55(s, 3 H), 1.42(t, 3 H), 1.35(d, 3 H, J = 6.8 Hz) |
| 208 | 7-methyl, 5-Cl, 3-ethyl-2H-indazol-2-yl | 8.10(s, 1 H), 7.85(m, 2 H), 7.75(s, 1 H), 7.20(m, 1 H), 6.81(m, 2 H), 5.23(q, 1 H), 4.71(d, 1 H, J = 14.2 Hz), 3.88(d, 1 H, J = 14.1 Hz), 3.28(q, 2 H), 2.56(s, 3 H), 1.41(t, 3 H), 1.35(d, 3 H, J = 6.8 Hz) |
| 209 | 7-methyl, 5-Cl, 3-ethyl-1H-indazol-1-yl | 8.11(s, 1 H), 8.03(m, 2 H), 7.78(m, 2 H), 6.89(m, 2 H), 5.80(br, 1 H), 5.31(q, 1 H), 4.58(d, 1 H, J = 14.2 Hz), 3.65(d, 1 H, J = 14.2 Hz), 3.33(q, 2 H), 2.55(s, 3 H), 1.42(t, 3 H), 1.34(d, 3 H, J = 6.8 Hz) |
| 210 | 6-F, 5-Cl, 3-ethyl-2H-indazol-2-yl | 8.13(s, 1 H), 7.88(m, 1 H), 7.75(s, 1 H), 7.20(m, 2 H), 6.81(m, 2 H), 5.23(q, 1 H), 4.71(d, 1 H, J = 14.2 Hz), 3.88(d, 1 H, J = 14.1 Hz), 3.28(q, 2 H), 1.41(t, 3 H), 1.39(d, 3 H, J = 6.8 Hz) |

TABLE 5-continued

| Ex. | Het | ¹H-NMR(300 MHz, CDCl₃) δ |
|---|---|---|
| 211 | 5-chloro-6-fluoro-3-ethyl-1H-indazol-1-yl | 8.15(s, 1 H), 7.59(m, 2 H), 7.78(m, 2 H), 6.89(m, 2 H), 5.80(br, 1 H), 5.22(q, 1 H), 4.58(d, 1 H, J = 14.2 Hz), 3.65(d, 1 H, J = 14.2 Hz), 3.35(q, 2 H), 1.42(t, 3 H), 1.37(d, 3 H, J = 6.8 Hz) |
| 212 | 5-fluoro-6-methyl-3-ethyl-2H-indazol-2-yl | 8.13(s, 1 H), 7.88(m, 2 H), 7.75(s, 1 H), 7.20(m, 1 H), 6.81(m, 2 H), 5.23(q, 1 H), 4.71(d, 1 H, J = 14.2 Hz), 3.88(d, 1 H, J = 14.1 Hz), 3.28(q, 2 H), 2.55(s, 3 H), 1.39(t, 3 H), 1.36(d, 3 H, J = 6.8 Hz) |
| 213 | 5-fluoro-6-methyl-3-ethyl-1H-indazol-1-yl | 8.11(s, 1 H), 8.03(m, 2 H), 7.78(m, 2 H), 6.89(m, 2 H), 5.80(br, 1 H), 5.31(q, 1 H), 4.58(d, 1 H, J = 14.2 Hz), 3.65(d, 1 H, J = 14.2 Hz), 3.35(q, 2 H), 2.45(s, 3 H), 1.42(t, 3 H), 1.35(d, 3 H, J = 6.8 Hz) |
| 214 | 5-chloro-6-methyl-3-ethyl-2H-indazol-2-yl | 8.18(s, 1 H), 8.06(m, 2 H), 7.75(s, 1 H), 7.20(m, 1 H), 6.81(m, 2 H), 5.23(q, 1 H), 4.71(d, 1 H, J = 14.2 Hz), 3.88(d, 1 H, J = 14.1 Hz), 3.28(q, 2 H), 2.56(s, 3 H), 1.41(t, 3 H), 1.35(d, 3 H, J = 6.8 Hz) |
| 215 | 5-chloro-6-methyl-3-ethyl-1H-indazol-1-yl | 8.21(s, 1 H), 8.12(m, 2 H), 7.91(m, 2 H), 6.89(m, 2 H), 5.80(br, 1 H), 5.33(q, 1 H), 4.58(d, 1 H, J = 14.2 Hz), 3.65(d, 1 H, J = 14.2 Hz), 3.33(q, 2 H), 2.55(s, 3 H), 1.39(t, 3 H), 1.33(d, 3 H, J = 6.8 Hz) |
| 216 | 6-bromo-3-ethyl-2H-indazol-2-yl | 8.19(s, 1 H), 7.86(m, 2 H), 7.75(s, 1 H), 7.20(m, 2 H), 6.81(m, 2 H), 5.23(q, 1 H), 4.71(d, 1 H, J = 14.2 Hz), 3.88(d, 1 H, J = 14.1 Hz), 3.28(q, 2 H), 1.43(t, 3 H), 1.37(d, 3 H, J = 6.8 Hz) |
| 217 | 6-bromo-3-methyl-1H-indazol-1-yl | 8.20(s, 1 H), 8.03(m, 2 H), 7.78(m, 3 H), 6.89(m, 2 H), 5.80(br, 1 H), 5.31(q, 1 H), 4.58(d, 1 H, J = 14.2 Hz), 3.65(d, 1 H, J = 14.2 Hz), 3.35(q, 2 H), 1.42(t, 3 H), 1.35(d, 3 H, J = 6.8 Hz) |
| 218 | 7-bromo-3-methyl-2H-indazol-2-yl | 8.22(s, 1 H), 7.96(m, 2 H), 7.75(s, 1 H), 7.20(m, 2 H), 6.81(m, 2 H), 5.23(q, 1 H), 4.71(d, 1 H, J = 14.2 Hz), 3.88(d, 1 H, J = 14.1 Hz), 3.28(q, 2 H), 1.43(t, 3 H), 1.37(d, 3 H, J = 6.8 Hz) |

TABLE 5-continued

| Ex. | Het | ¹H-NMR(300 MHz, CDCl₃) δ |
|---|---|---|
| 219 | 7-bromo-3-ethyl-1H-indazol-1-yl | 8.20(s, 1 H), 8.03(m, 2 H), 7.78(m, 3 H), 6.89(m, 2 H), 5.80(br, 1 H), 5.31(q, 1 H), 4.58(d, 1 H, J = 14.2 Hz), 3.67(d, 1 H, J = 14.2 Hz), 3.41(q, 2 H), 1.40(t, 3 H), 1.36(d, 3 H, J = 6.8 Hz) |
| 220 | 5-chloro-3-ethyl-6-methyl-1H-indazol-1-yl | 8.15(s, 1 H), 7.88(m, 2 H), 7.81(s, 1 H), 7.35(m, 2 H), 6.81(m, 2 H), 5.21(q, 1 H), 4.81(d, 1 H, J = 14.2 Hz), 3.85(d, 1 H, J = 14.1 Hz), 3.31(q, 2 H), 1.45(t, 3 H), 1.35(d, 3 H, J = 6.8 Hz) |
| 221 | 5-chloro-3-ethyl-6-methyl-2H-indazol-2-yl | 8.20(s, 1 H), 8.03(m, 2 H), 7.78(m, 3 H), 6.89(m, 2 H), 5.80(br, 1 H), 5.31(q, 1 H), 4.58(d, 1 H, J = 14.2 Hz), 3.65(d, 1 H, J = 14.2 Hz), 3.35(q, 2 H), 1.44(t, 3 H), 1.33(d, 3 H, J = 6.8 Hz) |
| 222 | 6-bromo-3-methyl-1H-indazol-1-yl | 8.21(s, 1 H), 8.11(s, 1 H), 7.82(m, 1 H), 7.53(m, 1 H), 7.15(m, 2 H), 6.65(m, 2 H), 5.03(q, 1 H), 4.73(d, 1 H), 3.32(d, 1 H), 1.51(d, 3 H) |
| 223 | 6-bromo-3-ethyl-2H-indazol-2-yl | 8.35(s, 1 H), 8.21(s, 1 H), 7.53(m, 1 H), 7.31(m, 3 H), 6.60(m, 1 H), 5.52(br, 1 H), 5.07(q, 1 H), 4.71(d, 1 H), 3.30(d, 1 H), 1.49(d, 3 H) |
| 224 | 7-bromo-3-methyl-2H-indazol-2-yl | 8.19(s, 1 H), 8.18(s, 1 H), 7.91(m, 1 H), 7.62(m, 1 H), 7.15(m, 2 H), 6.65(m, 2 H), 5.03(q, 1 H), 4.73(d, 1 H), 3.32(d, 1 H), 1.53(d, 3 H) |
| 225 | 7-bromo-3-ethyl-1H-indazol-1-yl | 8.26(s, 1 H), 8.22(s, 1 H), 7.93(m, 1 H), 7.71(m, 3 H), 6.85(m, 2 H), 5.51(br, 1 H), 5.07(q, 1 H), 4.71(d, 1 H), 3.30(d, 1 H), 1.52(d, 3 H) |
| 226 | 5-bromo-3-fluoro-1H-indazol-1-yl | 8.21(s, 1 H), 8.11(s, 1 H), 7.82(m, 1 H), 7.53(m, 1 H), 7.15(m, 2 H), 6.65(m, 2 H), 5.03(q, 1 H), 4.73(d, 1 H), 3.32(d, 1 H), 1.51(d, 3 H) |

TABLE 5-continued
| Ex. | Het | ¹H-NMR(300 MHz, CDCl₃) δ |
|---|---|---|
| 227 | 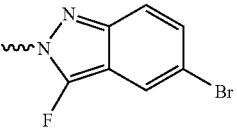 | 8.35(s, 1 H), 8.21(s, 1 H), 7.53(m, 1 H), 7.31(m, 3 H), 6.60(m, 2 H), 5.52(br, 1 H), 5.07(q, 1 H), 4.71(d, 1 H), 3.30(d, 1 H), 1.49(d, 3 H) |
| 228 | 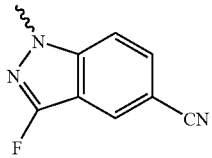 | 8.19(s, 1 H), 8.08(s, 1 H), 7.75(m, 1 H), 7.51(m, 1 H), 7.12(m, 2 H), 6.65(m, 2 H), 5.03(q, 1 H), 4.73(d, 1 H), 3.32(d, 1 H), 1.39(d, 3 H) |
| 229 | 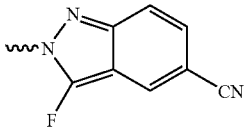 | 8.31(s, 1 H), 8.21(s, 1 H), 7.53(m, 1 H), 7.31(m, 3 H), 6.60(m, 2 H), 5.81(br, 1 H), 5.07(q, 1 H), 4.71(d, 1 H), 3.30(d, 1 H), 1.37(d, 3 H) |
| 230 | 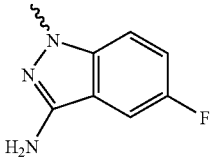 | 8.15(s, 1 H), 8.01(s, 1 H), 7.71(m, 1 H), 7.15(m, 1 H), 7.05(m, 2 H), 6.65(m, 2 H), 5.03(q, 1 H), 4.73(d, 1 H), 3.32(d, 1 H), 1.51(d, 3 H) |
| 231 | 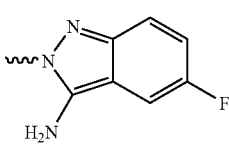 | 8.21(s, 1 H), 8.12(s, 1 H), 7.75(m, 1 H), 7.31(m, 3 H), 6.60(m, 2 H), 5.81(br, 1 H), 5.07(q, 1 H), 4.71(d, 1 H), 3.30(d, 1 H), 1.49(d, 3 H) |
| 232 | 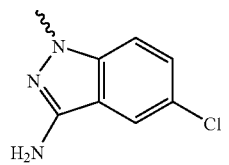 | 8.13(s, 1 H), 7.96(s, 1 H), 7.73(m, 1 H), 7.15(m, 1 H), 7.05(m, 2 H), 6.81(m, 2 H), 5.03(q, 1 H), 4.73(d, 1 H), 3.32(d, 1 H), 1.53(d, 3 H) |
| 233 | 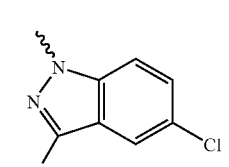 | 8.19(s, 1 H), 8.08(s, 1 H), 7.78(m, 1 H), 7.41(m, 3 H), 6.89(m, 2 H), 5.81(br, 1 H), 5.07(q, 1 H), 4.71(d, 1 H), 3.30(d, 1 H), 1.51(d, 3 H) |

Example 234

(2R,3R)-2-(2,4-difluorophenyl)-3-(5-nitro-1H-indazol-1-yl)-1-(1H-1,2,4-triazol-1-yl)butan-2-ol The same procedure as in Example 50, except that 5-nitroindazole was used, was conducted to produce the title compound.

$^1$H-NMR (300 MHz, CDCl$_3$) δ 8.79 (s, 1H), 8.36 (m, 2H), 7.92 (s, 1H), 7.64 (m, 3H), 6.83 (m, 2H), 5.74 (br, 1H), 5.43 (q, 1H), 4.88 (d, 1H, J=14.2 Hz), 3.76 (d, 1H, J=14.2 Hz), 1.49 (d, 3H, J=7.0 Hz).

Example 235

(2R,3R)-2-(2,4-difluorophenyl)-3-(5-nitro-2H-indazol-2-yl)-1-(1H-1,2,4-triazol-1-yl)butan-2-ol The crude product of Example 234 was purified by chromatography on silica gel to give the title compound (Yield 43%).

1H-NMR (300 MHz, CDCl$_3$) d8.81 (s, 1H), 8.36 (m, 2H), 7.92 (s, 1H), 7.64 (m, 3H), 6.83 (m, 2H), 5.92 (br, 1H), 5.43 (q, 1H), 4.88 (d, 1H, J=14.2 Hz), 3.68 (d, 1H, J=14.2 Hz), 1.47 (d, 3H, J=6.8 Hz).

Example 236

(2R,3R)-3-(5-amino-1H-indazol-1-yl)-2-(2,4-difluorophenyl)-1-(1H-1,2,4-triazol-1-yl)butan-2-ol With the exception that (2R,3R)-2-(2,4-difluorophenyl)-3-(5-nitro-1H-indazol-1-yl)-1-(1H-1,2,4-triazol-1-yl)butan-2-ol was used, the same procedure as in Example 6 was conducted to produce the title compound. (Yield 90%)

$^1$H-NMR (300 MHz, CDCl$_3$) δ 7.98 (s, 1H), 7.91 (s, 1H), 7.58 (m, 2H), 7.48 (d, 1H, J=8.9 Hz), 7.25 (m, 1H), 7.17 (m, 1H), 6.83 (m, 2H), 6.05 (br, 1H, —OH), 5.37 (q, 1H), 4.76 (d, 1H, J=15.1 Hz), 3.60 (d, 1H, J=14.2 Hz), 1.38 (d, 3H, J=6.9 Hz).

Example 237

(2R,3R)-3-(5-amino-2H-indazol-2-yl)-2-(2,4-difluorophenyl)-1-(1H-1,2,4-triazol-1-yl)butan-2-ol With the exception that (2R,3R)-2-(2,4-difluorophenyl)-3-(5-nitro-2H-indazol-2-yl)-1-(1H-1,2,4-triazol-1-yl)butan-2-ol was used, the same procedure as in Example 6 was conducted to produce the title compound. (Yield 87%)

$^1$H-NMR (300 MHz, CDCl$_3$) δ 8.02 (s, 1H), 7.91 (s, 1H), 7.58 (m, 2H), 7.48 (d, 1H, J=8.9 Hz), 7.25 (m, 1H), 7.17 (m, 1H), 6.83 (m, 2H), 6.06 (br, 1H, —OH), 5.36 (q, 1H), 4.76 (d, 1H), 3.58 (d, 1H), 1.35 (d, 3H, J=6.9 Hz).

Example 238

(2R,3R)-3-(5-(benzylamino)-1H-indazol-2-yl)-2-(2,4-difluorophenyl)-1-(1H-1,2,4-triazol-1-yl)butan-2-ol With the exception that (2R,3R)-3-(5-amino-1H-indazol-1-yl)-2-(2,4-difluorophenyl)-1-(1H-1,2,4-triazol-1-yl)butan-2-ol was used, the same procedure as in Example 9 was conducted to produce the title compound.

$^1$H-NMR (300 MHz, CDCl$_3$) δ 7.89 (d, 2H), 7.55 (m, 1H), 7.36 (m, 8H), 6.94 (s, 1H), 6.80 (m, 2H), 6.09 (br, 1H, —OH), 5.32 (q, 1H), 4.74 (d, 1H), 4.69 (s, 2H), 3.54 (d, 1H, J=14.2 Hz), 1.33 (d, 3H, J=6.8 Hz).

Example 239 to 314

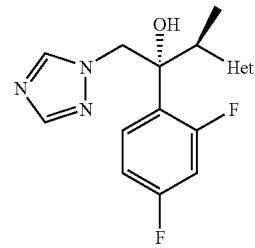

Compounds of the chemical formula above, wherein Het is as listed in Table 6 below, were synthesized according to procedures similar to that of Example 238.

TABLE 6

| Ex. | Het | $^1$H-NMR(300 MHz, CDCl$_3$) δ |
|---|---|---|
| 239 | 5-(2-nitrobenzylamino)-1H-indazol-1-yl | 8.10(d, 1 H), 7.89(d, 2 H), 7.70(d, 1 H), 7.59(m, 3 H), 7.43(m, 2 H), 6.98(m, 1 H), 6.81(m, 2 H), 6.68(s, 1 H), 6.08(br, 1 H), 5.33(q, 1 H), 4.78(s, 2 H), 4.73(d, 1 H, J = 14.2 Hz), 3.53(d, 1 H, J = 14.2 Hz), 1.34(d, 3 H, J = 6.8 Hz) |
| 240 | 5-(3-chlorobenzylamino)-1H-indazol-1-yl | 7.91(d, 2 H), 7.56(m, 2 H), 7.41(m, 2 H), 7.28(m, 2 H), 6.98(m, 1 H), 6.82(m, 4 H), 6.11(br, 1 H, —OH), 4.74(d, 1 H, J = 14.2 Hz), 4.38(s, 2 H), 3.54(d, 1 H, J = 14.2 Hz), 1.35(d, 3 H, J = 6.8 Hz) |

TABLE 6-continued

| Ex. | Het | $^1$H-NMR(300 MHz, CDCl$_3$) δ |
|---|---|---|
| 241 | 1H-indazol-5-yl-NH-CH(CH$_3$)-3-CF$_3$-phenyl (indazole-NH-CH$_2$-Ar(3-CF$_3$)) | 7.94(d, 2 H), 7.55(m, 8 H), 7.17(m, 1 H), 6.82(m, 2 H), 6.03(br, 1 H, —OH), 5.34(q, 1 H), 4.75(d, 1 H, J = 14.0 Hz), 4.68(s, 2 H), 3.55(d, 1 H, J = 14.3 Hz), 1.38(d, 3 H, J = 7.7 Hz) |
| 242 | indazole-NH-CH$_2$-Ar(3-NO$_2$) | 8.13(m, 3 H), 7.89(m, 2 H), 7.62(m, 4 H), 7.26(m, 1 H), 6.90(m, 2 H), 6.00(br, 1 H), 5.34(q, 1 H), 4.72(m, 3 H), 3.58(d, 1 H), 1.34(d, 3 H) |
| 243 | indazole-NH-CH$_2$-Ar(4-Br) | 7.97(s, 1 H), 7.88(s, 1 H), 7.57(m, 3 H), 7.47(m, 2 H), 7.30(m, 2 H), 7.14(m, 2 H), 6.80(m, 2 H), 5.97(br, 1 H, —OH), 5.34(q, 1 H), 4.74(d, 1 H, J = 14.4 Hz), 4.36(s, 2 H), 3.56(d, 1 H, J = 14.3 Hz), 1.37(d, 3 H, J = 6.8 Hz) |
| 244 | indazole-NH-CH$_2$-Ar(4-F) | 7.91(d, 2 H), 7.54(m, 2 H), 7.39(m, 3 H), 7.22(m, 1 H), 6.98(m, 3 H), 6.83(m, 2 H), 6.11(br, 1 H), 5.35(q, 1 H), 4.74(d, 1 H, J = 14.3 Hz), 3.54(d, 1 H, J = 14.2 Hz), 1.35(d, 3 H, J = 6.8 Hz) |
| 245 | indazole-NH-CH$_2$-Ar(4-Cl) | 7.96(s, 1 H), 7.89(s, 1 H), 7.53(m, 2 H), 7.43(d, 1 H, J = 9.0 Hz), 7.32(m, 4 H), 7.03(d, 1 H, J = 8.6 Hz), 6.88(br, 1 H), 6.80(m, 2 H), 6.06(br, 1 H, —OH), 5.34(q, 1 H), 4.74(d, 1 H, J = 15.2 Hz), 3.54(d, 1 H, J = 14.2 Hz), 1.36(d, 3 H, J = 6.8 Hz) |
| 246 | indazole-NH-CH$_2$-Ar(4-CF$_3$) | 7.98(s, 1 H), 7.89(s, 1 H), 7.49(m, 8 H), 7.12(m, 1 H), 6.80(m, 2 H), 5.98(br, 1 H, —OH), 5.34(q, 1 H), 4.75(d, 1 H, J =14.8 Hz), 4.67(s, 2 H), 3.56(d, 1 H, J = 14.3 Hz), 1.36(d, 3 H, J = 6.8 Hz) |
| 247 | indazole-NH-CH$_2$-Ar(4-OCF$_3$) | 7.95(s, 1 H), 7.89(s, 1 H), 7.56(m, 2 H), 7.43(m, 3 H), 7.19(d, 2 H, J = 8.0 Hz), 7.0(dd, 1 H), 6.83(m, 3 H), 6.07(br, 1 H, —OH), 5.33(q, 1 H), 4.74(d, 1 H, J = 15.2 Hz), 4.40(s, 2 H), 3.54(d, 1 H, J = 14.2 Hz), 1.35(d, 3 H, J = 6.8 Hz) |

TABLE 6-continued

| Ex. | Het | $^1$H-NMR(300 MHz, CDCl$_3$) δ |
|---|---|---|
| 248 | indazol-5-yl-NH-CH$_2$-C$_6$H$_4$-4-NO$_2$ | 7.98(s, 1 H), 7.89(s, 1 H), 7.56(m, 2 H), 7.43(m, 3 H), 7.19(d, 2 H, J = 8.0Hz), 7.0(dd, 1 H), 6.83(m, 3 H), 6.07(br, 1 H, —OH), 5.33(q, 1 H), 4.74(d, 1 H), 4.40(s, 2 H), 3.44(d, 1 H), 1.38(d, 3 H, J = 6.8 Hz) |
| 249 | indazol-5-yl-NH-CH$_2$-C$_6$H$_4$-4-NH$_2$ | 8.03(s, 1 H), 7.91(s, 1 H), 7.56(m, 2 H), 7.43(m, 3 H), 7.19(d, 2 H), 7.13(m, 1 H), 6.85(m, 3 H), 6.07(br, 1 H, —OH), 5.33(q, 1 H), 4.74(d, 1 H), 4.40(s, 2 H), 3.44(d, 1 H), 1.45(d, 3 H) |
| 250 | indazol-5-yl-NH-CH$_2$-C$_6$H$_3$-2,4-F$_2$ | 7.95(s, 1 H), 7.92(s, 1 H), 7.55(m, 2 H), 7.41(m, 3 H), 7.26(s, 1 H), 7.18(d, 1 H, J = 8.3 Hz), 7.11(m, 1 H), 6.78(m, 2 H), 6.02(br, 1 H, —OH), 5.33(q, 1 H), 4.74(d, 1 H, J = 14.2 Hz), 4.46(s, 2 H), 3.54(d, 1 H), 1.33(d, 3 H, J = 6.8 Hz) |
| 251 | indazol-5-yl-NH-CH$_2$-C$_6$H$_3$-2,4-Cl$_2$ | 7.94(s, 1 H), 7.89(s, 1 H), 7.55(m, 2 H), 7.41(m, 3 H), 7.26(s, 1 H), 7.18(d, 1 H, J = 8.3 Hz), 7.00(d, 1 H, J = 9.0 Hz), 6.78(m, 2 H), 6.07(br, 1 H, —OH), 5.33(q, 1 H), 4.74(d, 1 H, J = 14.2 Hz), 4.46(s, 2 H), 3.54(d, 1 H, J = 14.2 Hz), 1.35(d, 3 H, J = 6.8 Hz) |
| 252 | indazol-5-yl-NH-CH$_2$-C$_6$H$_3$-2-NO$_2$-4-Cl | 8.09(s, 1 H), 7.89(s, 2 H), 7.68(m, 2 H), 7.55(m, 3 H), 7.42(d, 1 H, J = 8.9 Hz), 6.97(d, 1 H, J = 8.9 Hz), 6.80(m, 1 H), 6.05(br, 1 H, —OH), 5.31(q, 1 H), 4.73(m, 3 H), 3.53(d, 1 H, J= 14.3 Hz), 1.34(d, 3 H, J = 6.4 Hz) |
| 253 | indazol-5-yl-NH-CH$_2$-C$_6$H$_3$-2,6-F$_2$ | 8.03(s, 1 H), 7.89(s, 1 H), 7.55(m, 2 H), 7.41(m, 3 H), 7.21(s, 1 H), 7.18(d, 1 H, J = 8.3 Hz), 7.00(m, 1 H), 6.78(m, 2 H), 6.03(br, 1 H, —OH), 5.33(q, 1 H), 4.74(d, 1 H, J = 14.2 Hz), 4.46(s, 2 H), 3.54(d, 1 H, J = 14.2 Hz), 1.35(d, 3 H, J = 6.8 Hz) |
| 254 | indazol-5-yl-NH-CH$_2$-C$_6$H$_3$-2,6-Cl$_2$ | 8.02(s, 1 H), 7.89(s, 1 H), 7.55(m, 2 H), 7.41(m, 3 H), 7.21(s, 1 H), 7.18(d, 1 H, J = 8.3 Hz), 7.03(m, 1 H), 6.86(m, 2 H), 6.03(br, 1 H, —OH), 5.33(q, 1 H), 4.74(d, 1 H, J = 14.2 Hz), 4.46(s, 2 H), 3.54(d, 1 H, J = 14.2 Hz), 1.33(d, 3 H, J = 6.8 Hz) |

TABLE 6-continued

| Ex. | Het | ¹H-NMR(300 MHz, CDCl₃) δ |
|---|---|---|
| 255 | (1H-indazol-5-yl)-NH-CH₂-(2-chloro-6-fluorophenyl) | 7.99(s, 1 H), 7.90(s, 1 H), 7.55(m, 2 H), 7.40(d, 1 H, J = 9.0 Hz), 7.20(m, 2 H), 7.1(s, 1 H), 7.04(m, 2 H), 6.82(m, 2 H), 5.32(q, 1 H), 4.73(d, 1 H, J = 14.3 Hz), 4.55(s, 2 H), 3.54(d, 1 H, J = 14.2 Hz), 1.34(d, 3 H, J = 6.8 Hz) |
| 256 | (2H-indazol-5-yl)-NH-CH₂-(3,4-dichlorophenyl) | 7.95(s, 1 H), 7.89(s, 1 H), 7.55(m, 4 H), 7.43(m, 2 H), 7.03(m, 1 H), 6.81(m, 3 H), 6.05(s, 1 H), 5.32(q, 1 H), 4.74(d, 1 H, J = 14.4 Hz), 3.55(d, 1 H, J = 14.2 Hz), 1.36(d, 3 H, J = 6.9 Hz) |
| 257 | (1H-indazol-5-yl)-NH-CH₂-(3,4-dimethylphenyl) | 8.09(s, 1 H), 7.92(s, 1 H), 7.65(m, 4 H), 7.43(m, 2 H), 7.03(m, 1 H), 6.81(m, 3 H), 6.12(s, 1 H), 5.32(q, 1 H), 4.74(d, 1 H, J = 14.4 Hz), 3.55(d, 1 H, J = 14.2 Hz), 3.34(s, 3 H), 3.31(s, 3 H), 1.39(d, 3 H, J = 6.8 Hz) |
| 258 | (1H-indazol-5-yl)-NH-CH₂-(3,5-difluorophenyl) | 7.94(s, 1 H), 7.90(s, 1 H), 7.54(m, 2 H), 7.42(d, 1 H, J = 9.0 Hz), 6.97(m, 2 H), 6.76(m, 2 H), 6.70(m, 1 H), 6.07(br, 1 H, —OH), 5.33(q, 1 H), 4.74(d, 1 H, J = 14.3 Hz), 4.40(s, 2 H), 3.55(d, 1 H, J = 14.2 Hz), 1.35(d, 3 H, J = 6.8 Hz) |
| 259 | (1H-indazol-5-yl)-NH-CH₂-(3,5-dimethoxyphenyl) | 7.93(s, 1 H), 7.87(d, 2 H), 7.55(m, 2 H), 7.44(m, 2 H), 7.30(d, 2 H), 7.14(dd, 1 H), 6.94(d, 1 H), 6.78(m, 2 H), 5.32(q, 1 H), 4.75(d, 1 H), J = 15.1 Hz), 4.65(s, 2 H), 3.58(d, 1 H, J = 14.2 Hz), 1.35(d, 3 H, J = 6.8 Hz) |
| 260 | (1H-indazol-5-yl)-N(CH₂-phenyl)₂ | 7.90(d, 2 H), 7.54(m, 2 H), 7.36(m, 10 H), 7.19(m, 1 H), 6.8(m, 3 H), 6.09(br, 1 H), 5.31(q, 1 H), 4.73(d, 1 H), 4.69(s, 4 H), 3.54(d, 1 H, J = 14.2 Hz), 1.33(d, 3 H, J = 6.8 Hz) |

TABLE 6-continued

| Ex. | Het | $^1$H-NMR(300 MHz, CDCl$_3$) δ |
|---|---|---|
| 261 | indazol-5-yl-N,N-bis(2-nitrobenzyl) | 8.23(d, 2 H), 7.91(d, 2 H), 7.57(m, 8 H), 7.42(d, 1 H), 6.97(m, 1 H), 6.81(m, 3 H), 5.31(q, 1 H), 5.30(s, 4H), 4.7(d, 1 H, J = 15.3 Hz), 3.54(d, 1 H, J = 14.3 Hz), 1.35(d, 3 H, J = 6.8 Hz) |
| 262 | indazol-5-yl-N,N-bis(3-chlorobenzyl) | 7.91(d, 2 H), 7.56(m, 2 H), 7.42(d, 1 H), 7.20(m, 9 H), 6.91(s, 1 H), 6.8(m, 2 H), 6.07(br, 1 H, —OH), 5.32(q, 1 H), 4.75(d, 1 H, J = 15.2 Hz), 4.63(s, 2 H), 3.57(d, 1 H, J = 14.2 Hz), 1.35(d, 3 H, J = 6.8 Hz) |
| 263 | indazol-5-yl-N,N-bis(3-trifluoromethylbenzyl) | 7.92(d, 1 H), 7.50(m, 1 H), 7.16(m, 1 H), 6.96(m, 1 H), 6.80(m, 2 H), 6.05(br, 1 H, —OH), 5.33(q, 1 H), 4.78(d, 1 H, J = 14.3 Hz), 3.58(d, 1 H, J = 14.3 Hz), 1.36(d, 3 H, J = 6.8 Hz) |
| 264 | indazol-5-yl-N,N-bis(3-nitrobenzyl) | 8.13(m, 3 H), 7.9(m, 2 H), 7.52(m, 8 H), 7.16(m, 1 H), 6.95(m, 1 H), 6.81(m, 2 H), 6.00(br, 1 H), 5.33(q, 1 H), 4.75(m, 5 H), 3.58(d, 1 H, J = 14.2 Hz), 1.35(d, 3 H, J = 6.8 Hz) |
| 265 | indazol-5-yl-N,N-bis(4-fluorobenzyl) | 7.9(d, 2 H), 7.56(m, 2 H), 7.42(d, 1 H, J = 9.2 Hz), 7.23(m, 5 H), 7.01(m, 4 H), 6.98(s, 1 H), 6.82(m, 2 H), 6.06(br, 1 H, —OH), 5.32(q, 1 H), 4.74(d, 1 H, J = 15.0 Hz), 4.59(s, 4 H), 3.55(d, 1 H, J = 14.2 Hz), 1.35(d, 3 H, J = 6.8 Hz) |

TABLE 6-continued

| Ex. | Het | $^1$H-NMR(300 MHz, CDCl$_3$) δ |
|---|---|---|
| 266 | [indazole-N(CH$_2$-4-ClC$_6$H$_4$)$_2$] | 7.91(d, 2 H), 7.55(m, 2 H), 7.42(d, 1 H, J = 9.1 Hz), 7.25(m, 8 H), 7.13(m, 1 H), 6.95(s, 1 H), 6.8(m, 2 H), 6.04(br, 1 H, —OH), 5.31(q, 1 H), 4.74(d, 1 H, J = 14.2 Hz), 4.59(s, 4 H), 3.55(d, 1 H, J = 14.2 Hz, 1.35(d, 3 H, J = 6.8 Hz) |
| 267 | [indazole-N(CH$_2$-4-BrC$_6$H$_4$)$_2$] | 7.91(d, 2 H), 7.55(m, 2 H), 7.43(m, 5 H), 7.14(m, 5 H), 6.94(s, 1H), 6.91(m, 2 H), 6.04(br, 1 H, —OH), 5.31(m, 1 H), 4.74(d, 1 H, J = 14.3 Hz), 4.57(s, 4 H), 3.55(d, 1 H, J = 14.2 Hz), 1.35(d, 3 H, J = 6.8 Hz) |
| 268 | [indazole-N(CH$_2$-4-CF$_3$C$_6$H$_4$)$_2$] | 7.92(d, 2 H), 7.59(m, 5 H), 7.55(m, 1 H), 7.43(m, 5 H), 7.12(m, 1 H), 6.93(m, 1 H), 6.80(m, 2 H), 5.32(q, 1 H), 4.75(d, 1 H, J = 15.0 Hz), 4.71(s, 4 H), 3.56(d, 1 H, J = 14.2 Hz), 1.35(d, 3 H, J = 6.8 Hz) |
| 269 | [indazole-N(CH$_2$-4-CNC$_6$H$_4$)$_2$] | 7.91(d, 2 H), 7.64(d, 3 H), 7.54(m, 3 H), 7.44(d, 1 H), 7.4(d, 4 H0, 7.06(dd, 1 H), 6.88(m, 1 H), 6.8(m, 2 H), 5.98(br, 1 H, —OH), 5.32(q, 1 H), 4.74(d, 1 H, J = 15.0 Hz) 4.69(s, 4 H), 3.55(d, 1 H, J = 14.2 Hz), 1.35(d, 3 H, J = 6.8 Hz) |

TABLE 6-continued

| Ex. | Het | $^1$H-NMR(300 MHz, CDCl$_3$) δ |
|---|---|---|
| 270 | *indazol-5-yl-N(CH$_2$-C$_6$H$_4$-NO$_2$)$_2$* (bis(4-nitrobenzyl)) | 8.21(d, 4 H), 8.12(s, 1 H), 7.94(s, 1 H), 7.64(s, 1 H), 7.52(m, 6 H), 7.10(dd, 1 H), 6.92(m, 1 H), 6.81(m, 2 H), 5.32(q, 1 H), 4.77(m, 5 H), 3.60(d, 1 H, J = 14.1 Hz), 1.35(d, 3 H, J = 6.9 Hz) |
| 271 | *indazol-5-yl-N(CH$_2$-C$_6$H$_4$-NO$_2$)$_2$* | 8.20(d, 4 H), 7.93(s, 2 H), 7.58(s, 1 H), 7.50(m, 6 H), 7.10(dd, 1 H), 6.90(m, 1 H), 6.79(m, 2 H), 5.99(br, 1 H, —OH), 5.32(q, 1 H), 4.75(m, 5 H), 3.56(d, 1 H, J = 14.2 Hz), 1.35(d, 3 H, J = 6.9 Hz) |
| 272 | *indazol-5-yl-N(CH$_2$-C$_6$H$_4$-OCF$_3$)$_2$* | 7.93(d, 2 H), 7.57(s, 1 H), 7.55(m, 1 H0, 7.44(d, 1 H, J = 9.2 Hz), 7.32(m, 4 H), 7.16(m, 5 H), 6.99(s, 1 H), 6.81(m, 2 H), 6.16(br, 1 H, —OH), 5.32(q, 1 H), 4.75(d, 1 H, J = 14.6 Hz), 4.64(s, 4 H), 3.56(d, 1 H, J = 14.2Hz), 1.35(d, 3 H, J = 6.8 Hz) |
| 273 | *indazol-5-yl-N(CH$_2$-C$_6$H$_4$-CO$_2$Me)$_2$* | 8.0(d, 4 H), 7.91(d, 2 H), 7.54(m, 2 H), 7.39(m, 5 H), 7.12(dd, 1 H), 6.93(s, 1 H), 6.8(m, 2 H), 6.04(br, 1 H, —OH), 5.31(q, 1 H), 4.73(m, 5 H), 4.0(s, 6 H), 3.55(d, 1 H, J = 14.2 Hz), 1.33(d, 3 H, J = 6.8 Hz) |

TABLE 6-continued
| Ex. | Het | $^1$H-NMR(300 MHz, CDCl$_3$) δ |
|---|---|---|
| 274 | 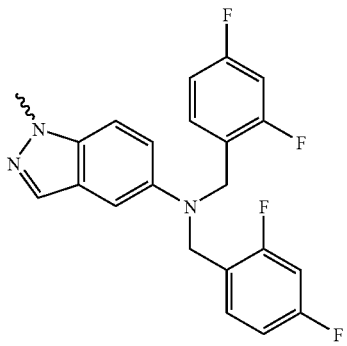 | 7.94(s, 1 H), 7.90(s, 1 H), 7.55(m, 2 H), 7.43(d, 1 H, J = 9.2 Hz), 7.26(m, 2 H), 7.14(m, 1 H), 6.98(s, 1 H), 6.81(m, 6 H), 6.03(br, 1 H, —OH), 5.32(q, 1 H), 4.74(d, 1 H, J = 14.4 Hz), 4.64(s, 4 H), 3.55(d, 1 H, J = 14.2 Hz), 1.35 (d, 3 H, J = 6.8 Hz) |
| 275 | 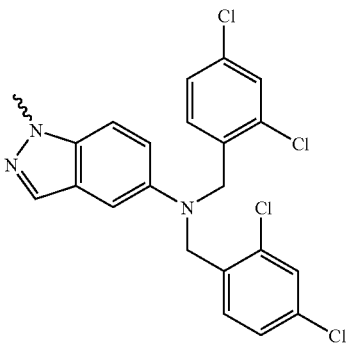 | 8.29(s, 1 H), 7.95(s, 1 H), 7.70(s, 1 H), 7.52(m, 1 H), 7.42(m, 3 H), 7.22(m, 5 H), 6.98(m, 1 H), 6.83(m, 2 H), 5.30(q, 1 H), 4.79(d, 1 H, J = 14.3 Hz), 3.61(d, 1 H, J = 14.2 Hz), 1.33(d, 3 H, J = 6.8 Hz) |
| 276 | 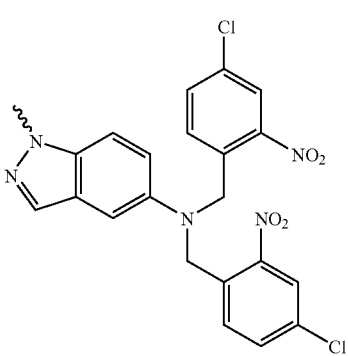 | 8.14(m, 3 H), 7.94(s, 1 H), 7.57(m, 8 H), 6.91(d, 1 H, J = 9.1 Hz), 5.32(q, 1 H), 5.04(s, 4 H), 4.77(d, 1 H, J = 14.6 Hz), 3.58 (d, 1 H, J = 14.2 Hz), 1.35(d, 3 H, J = 6.6 Hz) |
| 277 | 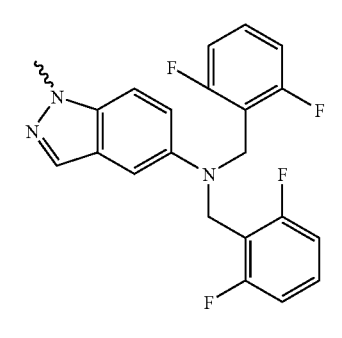 | 7.95(s, 1 H), 7.90(s, 1 H), 7.52(m, 2 H), 7.36(s, 2 H), 7.25(m, 1 H), 7.16(m, 2 H), 6.81(m, 6 H), 6.08(br, 1 H, —OH), 5.29(q, 1 H), 4.71(d, 1 H, J = 14.3 Hz), 4.61(s, 4 H), 3.53(d, 1 H, J = 14.2 Hz), 1.31(d, 3 H, J = 6.7 Hz) |

TABLE 6-continued

| Ex. | Het | $^1$H-NMR(300 MHz, CDCl$_3$) δ |
|---|---|---|
| 278 | indazol-5-yl-N,N-bis(2,6-dichlorobenzyl) | 7.99(s, 1 H), 7.93(s, 1 H), 7.55(m, 2 H), 7.41(s, 1 H), 7.27(m, 6 H), 7.09(m, 2 H), 6.82(m, 2 H), 6.07(br, 1 H, —OH), 5.32(q, 1 H), 4.73(d, 1 H, J = 14.2 Hz), 4.51(s, 4 H), 3.52(d, 1 H, J = 14.2 Hz), 1.35(d, 3 H, J = 6.8 Hz) |
| 279 | indazol-5-yl-N,N-bis(2-chloro-6-fluorobenzyl) | 8.30(s, 1 H), 7.98(s, 1 H), 7.70(s, 1 H), 7.25(m, 1 H), 7.35(d, 3 H), 7.13(m, 4 H), 6.88(m, 4 H), 5.30(q, 1 H), 4.77(d, 1 H, J = 14.4 Hz), 4.57(s, 4 H), 3.61(d, 1 H, J = 14.2 Hz), 1.31(d, 3 H, J = 6.8 Hz) |
| 280 | indazol-5-yl-N,N-bis(4-methyl-3-nitrobenzyl) | 7.91(d, 2 H), 7.55(m, 2 H), 7.38(d, 1 H, J = 9.2 Hz), 7.14(m, 1 H), 6.96(s, 1 H), 6.81(m, 2 H), 6.47(s, 4 H), 6.36(s, 2 H), 6.09(br, 1 H,—OH), 5.31(q, 1 H), 4.73(d, 1 H, J = 14.7 Hz), 4.61(s, 4 H), 3.75(s, 6 H), 3.55(d, 1 H, J = 14.2 Hz), 1.34(d, 3 H, J = 6.9 Hz) |
| 281 | indazol-5-yl-N,N-bis(3,4-dichlorobenzyl) | 7.96(d, 2 H), 7.55(m, 2 H), 7.41(m, 5 H), 7.12(m, 3 H), 6.94(m, 1 H), 6.80(m, 2 H), 6.07(br, 1 H), 5.32(q, 1 H), 4.76(d, 1 H, J = 14.4 Hz), 4.57(s, 4 H), 3.59(d, 1 H, J = 14.2 Hz), 1.35(d, 3 H, J = 6.8 Hz) |

TABLE 6-continued

| Ex. | Het | ¹H-NMR(300 MHz, CDCl₃) δ |
|---|---|---|
| 282 | (1H-indazol-5-yl)-N,N-bis(3,4-dimethylbenzyl) | 7.98(d, 2 H), 7.85(m, 2 H), 7.51(m, 5 H), 7.21(m, 3 H), 6.94(m, 1 H), 6.80(m, 2 H), 6.07(br, 1 H), 5.32(q, 1 H), 4.76(d, 1 H, J = 14.4 Hz), 4.57(s, 4 H), 3.59(d, 1 H, J = 14.2 Hz), 3.54(s, 6 H), 3.51(s, 6 H), 1.35(d, 3 H, J = 6.8 Hz) |
| 283 | (1H-indazol-5-yl)-N,N-bis(3,5-difluorobenzyl) | 7.95(s, 2 H), 7.55(m, 2 H), 7.44(d, 1 H, J = 9.2 Hz), 7.07(dd, 1 H), 6.89(m, 1 H), 6.82(m, 6 H), 6.72(m, 2 H), 6.07(br, 1 H, —OH), 5.33(q, 1 H), 4.76(d, 1 H, J = 14.3 Hz), 4.63(s, 4 H), 3.60(d, 1 H, J = 14.2 Hz), 1.35(d, 3 H, J = 6.8 Hz) |
| 284 | (1H-indazol-5-yl)-N,N-bis(3,5-dimethoxybenzyl) | 8.24(s, 1 H), 7.97(s, 1 H), 7.82(s, 2 H), 7.70(s, 1 H), 7.51(m, 4 H), 7.32(d, 2 H), 7.20(m, 1 H), 7.10(s, 1 H), 6.83(m, 2 H), 5.32(q, 1 H), 4.79(d, 1 H, J = 14.1 Hz), 4.68(s, 4 H), 2.56(s, 6 H), 1.35(d, 3 H, J = 6.8 Hz) |
| 285 | (1H-indazol-5-yl)-N,N-bis(pentafluorobenzyl) | 7.90(s, 2 H), 7.52(m, 2 H), 7.38(m, 1 H), 7.08(m, 2 H), 6.82(m, 2 H), 6.13(br, 1 H, —OH), 5.32(q, 1 H), 4.75(d, 1 H, J = 14.5 Hz), 4.64(s, 4 H), 3.56(d, 1 H, J = 14.2 Hz), 1.34(d, 3 H, J = 6.7 Hz) |

TABLE 6-continued
| Ex. | Het | $^1$H-NMR(300 MHz, CDCl$_3$) δ |
|---|---|---|
| 286 | 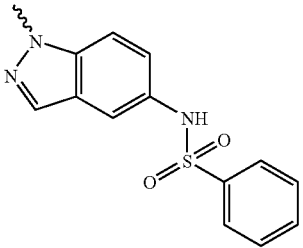 | 8.14(s, 1 H), 7.96(s, 3 H), 7.82(s, 1 H), 7.70(m, 1 H), 7.6(m, 3 H), 7.48(m, 1 H), 7.2(m, 1 H), 7.01(m, 1 H), 6.82(m, 2 H), 5.92(br, 1 H), 4.83(d, 1 H, J = 8.6 Hz), 3.78(d, 1 H, J = 9.6 Hz), 1.44(d, 3 H, J = 7.0 Hz) |
| 287 | 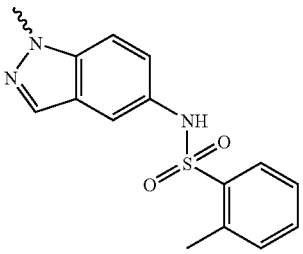 | 8.14(s, 1 H), 8.04(d, 2 H), 7.63(m, 2 H), 7.51(m, 2 H), 7.27(m, 3 H), 6.97(m, 1 H), 6.81(m, 2 H), 5.86(br, 1 H), 5.38(q, 1 H), 4.81(d, 1 H, J = 14.3 Hz), 3.68(d, 1 H, J = 14.2 Hz), 2.37(s, 3 H), 1.42(d, 3 H, J = 6.7 Hz) |
| 288 | 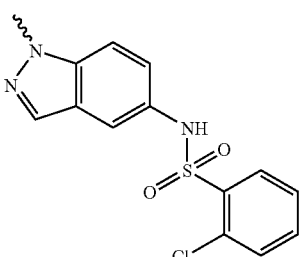 | 8.15(s, 1 H), 7.97(s, 1 H), 7.81(s, 1 H), 7.60(s, 1 H), 7.51(m, 5 H), 7.18(m, 1 H), 6.99(m, 1 H), 6.79(m, 2 H), 5.86(br, 1 H), 5.37(q, 1 H), 4.79(d, 1 H, J = 14.3 Hz), 3.66(d, 1 H, J = 14.2 Hz), 1.4(d, 3 H, J = 6.9 Hz) |
| 289 | 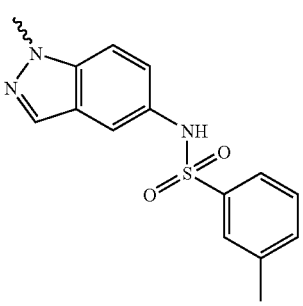 | 8.14(s, 1 H), 7.98(s, 1 H), 7.81(s, 1 H), 7.71(d, 2 H), 7.62(s, 1 H), 7.46(m, 3 H), 7.20(m, 1 H), 7.0(m, 1 H), 6.8(m, 2 H), 5.92(br, 1 H), 5.39(q, 1 H), 4.83(d, 1 H, J = 14.0 Hz), 3.77(d, 1 H, J = 7.5 Hz), 2.45(s, 3 H), 1.41(d, 3 H, J = 6.3 Hz) |
| 290 | 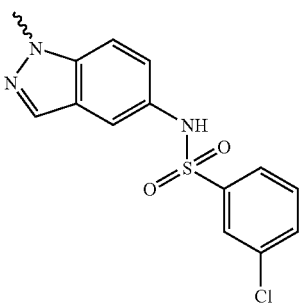 | 8.16(s, 1 H), 7.99(m, 4 H), 7.63(s, 1 H), 7.52(m, 2 H), 7.25(m, 3 H), 7.06(m, 1 H), 6.83(m, 2 H), 5.91(br, 1 H), 5.41(q, 1 H), 4.86(d, 1 H), 3.78(d, 1 H), 1.44(d, 3 H) |

TABLE 6-continued

| Ex. | Het | $^1$H-NMR(300 MHz, CDCl$_3$) δ |
|---|---|---|
| 291 | *indazol-5-yl-NH-SO$_2$-C$_6$H$_4$-CH$_3$* | 8.18(s, 1 H), 8.08(s, 1 H), 7.92(m, 1 H), 7..86(m, 1 H), 7.67(m, 2 H), 7.56(m, 3 H), 7.2(m, 1 H), 7.08(m, 1 H), 6.83(m, 2 H), 5.9(br, 1 H), 5.4(q, 1 H), 4.87(d, 1 H, J = 14.6 Hz). 3.8(d, 1 H, J = 14.3 Hz), 1.44(d, 3 H, J = 7.4 Hz) |
| 292 | *indazol-5-yl-NH-SO$_2$-C$_6$H$_4$-F* | 8.16(s, 1 H), 7.99(m, 4 H), 7.63(s, 1 H), 7.52(m, 2 H), 7.25(m, 3 H), 7.06(m, 1 H), 6.83(m, 2 H), 5.87(br, 1 H), 5.38(q, 1 H), 4.86(d, 1 H, J = 14.3 Hz), 3.78(d, 1 H, J = 13.4 Hz), 1.44(d, 3 H, J = 7.1 Hz) |
| 293 | *indazol-5-yl-NH-SO$_2$-C$_6$H$_4$-Cl* | 8.17(s, 1 H), 8.06(s, 1 H), 7.9(m, 2 H), 7.65(s, 1 H), 7.57(m, 4 H), 7.48(d, 1 H), 7.06(dd, 1 H), 6.83(m, 2 H), 5.88(br, 1 H), 5.39(q, 1 H), 4.86(d, 1 H, J = 14.6 Hz), 3.8(d, 1 H, J = 14.2 Hz), 1.44(d, 3 H, J = 7.0 Hz) |
| 294 | *indazol-5-yl-NH-SO$_2$-C$_6$H$_4$-Br* | 8.17(s, 1 H), 7..97(s, 1 H), 7.84~7.70(m, 6 H), 7.56(m, 2 H), 7.06(dd, 1H), 6.82(m, 2 H), 5.86(br, 1 H), 5.39(q, 1 H), 4.86(d, 1 H, J = 14.8 Hz), 3.78(d, 1 H, J = 14.1 Hz), 1.44(d, 3 H, J = 7.0 Hz) |
| 295 | *indazol-5-yl-NH-SO$_2$-C$_6$H$_4$-NO$_2$* | 8.45(m, 3 H), 8.18(m, 3 H), 7.94(s, 1 H), 7.59(m, 2 H), 7.5(d, 1 H), 7.04(dd, 1 H), 6.82(m, 2 H), 5.79(br, 1 H), 5.4(q, 1 H), 4.89(d, 1 H, J = 14.6 Hz), 3.82(d, 1 H, J = 14.3 Hz), 1.48(d, 3 H, J = 6.9 Hz) |

TABLE 6-continued

| Ex. | Het | $^1$H-NMR(300 MHz, CDCl$_3$) δ |
|---|---|---|
| 296 | indazol-5-yl-NH-SO$_2$-C$_6$H$_4$-CF$_3$ | 8.18(s, 1 H), 8.12(m, 2 H), 7.99(s, 1 H), 7.87(m, 2 H), 7.64(s, 1 H), 7.56(m, 2 H), 7.5(d, 1 H), 7.06(dd, 1 H), 6.82(m, 2 H), 5.85(br, 1 H), 5.4(q, 1 H), 4.88(d, 1 H, J = 14.6 Hz), 3.81(d, 1 H, J = 14.3 Hz), 1.46(d, 3 H, J = 6.9 Hz) |
| 297 | indazol-5-yl-NH-SO$_2$-C$_6$H$_4$-tBu | 8.15(s, 2 H), 7.88(d, 2 H), 7.72(s, 1 H), 7.6~7.47(m, 5 H), 7.14(m, 1 H), 6.84(m, 2 H), 5.97(br, 1 H), 5.4(q, 1 H), 4.86(d, 1 H, J = 14.3 Hz), 3.79(d, 1 H, J = 14.6 Hz), 1.42(d, 3 H, J = 6.3 Hz), 1.39(s, 9 H) |
| 298 | indazol-5-yl-NH-SO$_2$-C$_6$H$_4$-OMe | 8.14(s, 1 H),, 7.99(s, 1 H), 7.88(d, 2 H), 7.63(s, 1 H), 7.57(m, 1 H), 7.50(m, 2 H), 7.18(m, 1 H), 7.00(m, 2 H), 6.83(m, 2 H), 5.93(br, 1 H), 5.38(q, 1 H), 4.83(m, 1 H), 3.92(s, 3 H), 3.78(d, 1 H), 1.41(d, 3 H, J = 7.0 Hz) |
| 299 | indazol-5-yl-NH-SO$_2$-C$_6$H$_3$-2,3-Cl$_2$ | 8.20(s, 1 H), 8.12(d, 1 H), 7.89(d, 1 H), 7.76(d, 1 H), 7.68(s, 1 H), 7.55(m, 2 H), 7.39(m, 2 H), 7.21(m, 1 H), 6.83(m, 2 H), 5.91(br, 1 H), 5.39(q, 1 H), 4.85(d, 1 H, J = 14.6 Hz), 3.71(d, 1 H, J = 9.3 Hz), 1.42(d, 3 H, J = 6.8 Hz) |
| 300 | indazol-5-yl-NH-SO$_2$-C$_6$H$_3$-2,5-Cl$_2$ | 8.2(s, 1 H), 8.16(m, 1 H), 8.06(s, 1 H), 7.64(s, 1 H), 7.56(m, 2 H), 7.42(m, 2H), 7.2(m, 1 H), 6.82(m, 2 H), 5.86(br, 1 H), 5.39(q, 1 H), 4.83(d, 1 H, J = 14.5 Hz), 3.69(d, 1 H, J = 14.2 Hz), 1.43(d, 3 H, J = 6.9 Hz) |

TABLE 6-continued

| Ex. | Het | $^1$H-NMR(300 MHz, CDCl$_3$) δ |
|---|---|---|
| 301 | indazol-5-yl-NH-SO$_2$-(2,4-dichlorophenyl) | 8.15(m, 3 H), 7.83(d, 1 H), 7.69(s, 1 H), 7.55(m, 3 H), 7.41(m, 3 H), 6.83(m, 2 H), 5.93(br, 1 H), 5.39(q, 1 H), 4.84(d, 1 H, J = 14.6 Hz), 3.72(d, 1 H, J = 5.9 Hz), 1.42(d, 3 H, J = 6.7 Hz) |
| 302 | indazol-5-yl-NH-SO$_2$-(3,4-dichlorophenyl) | 8.16(m, 3 H), 7.83(d, 1 H), 7.69(s, 1 H), 7.52(d, 2 H), 7.42(m, 3 H), 6.83(m, 2 H), 5.93(br, 1 H), 5.39(q, 1 H), 4.84(d, 1 H, J = 14.6 Hz), 3.72(d, 1 H, J = 5.9 Hz), 1.42(d, 3 H, J = 6.71 Hz) |
| 303 | indazol-5-yl-NH-SO$_2$-(3,5-dichlorophenyl) | 8.22(s, 1 H), 8.05(s, 1 H), 7.83(m, 3 H), 7.70(t, 3 H), 7.63(m, 3 H), 7.23(m, 1 H), 7.09(dd, 1 H), 6.84(m, 2 H), 5.87(br, 1 H), 5.43(q, 1 H), 4.87(d, 1 H, J = 14.5 Hz), 3.81(d, 1 H, J = 14.2 Hz), 1.46(d, 3 H, J = 6.9 Hz) |
| 304 | indazol-5-yl-NH-SO$_2$-(naphth-1-yl) | 8.37(t, 1 H), 8.11(m, 2 H), 8.04(s, 1 H), 7.97(d, 1 H), 7.92(t, 1 H), 7.51(m, 3 H), 7.32(d, 1 H), 7.16(m, 2 H), 7.02(m, 1 H), 6.81(m, 2 H), 5.82(br, 1 H), 5.32(q, 1 H), 4.75(d, 1 H, J = 14.6 Hz), 3.61(d, 1 H, J = 14.2 Hz), 1.38(d, 3 H, J = 6.9 Hz) |
| 305 | indazol-5-yl-NH-SO$_2$-(3-methylphenyl) | 8.12(s, 1 H), 8.02(s, 1 H), 7.96(m, 1 H), 7.83(s, 1 H), 7.71(m, 1 H), 7.66(s, 1 H), 7.53(m, 2 H), 7.37(m, 1 H), 7.18(m, 1 H), 6.99(m, 1 H), 6.75(m, 2 H), 5.93(br, 1 H), 5.42(q, 1 H), 4.95(s, 2 H), 4.82(d, 1 H, J = 14.4 Hz), 3.65(1 H, d, J = 14.2 Hz), 2.35(s, 3 H), 1.40(d, 3 H, J = 6.9 Hz) |

TABLE 6-continued

| Ex. | Het | $^1$H-NMR(300 MHz, CDCl$_3$) δ |
|---|---|---|
| 306 | [indazol-5-yl-NH-CH$_2$-CH(CH$_3$)-CH$_3$ isobutyl] | 8.08(s, 1 H), 7.88(d, 2 H), 7.58(m, 4 H), 6.81(m, 2 H), 5.85(br, 1 H, —OH), 5.37(q, 1 H), 4.77(d, 1 H, J = 14.3 Hz), 3.57(d, 1 H, J = 14.2 Hz), 3.02(d, 2 H), 1.83(m, 1 H), 1.48(m, 2 H), 1.01(d, 6 H) |
| 307 | [indazol-5-yl-NH-CH$_2$-CH$_2$-CH(CH$_3$)$_2$ isopentyl] | 8.06(s, 1 H), 7.88(d, 2 H), 7.58(m, 4 H), 6.81(m, 2 H), 5.85(br, 1 H, —OH), 5.37(q, 1 H), 4.77(d, 1 H, J = 14.3 Hz), 3.57(d, 1 H, J = 14.2 Hz), 3.06(d, 2 H), 2.07(m, 1 H), 1.01(d, 6 H) |
| 308 | [indazol-5-yl-NH-CH$_2$-CH(Et)$_2$ 2-ethylbutyl] | 8.08(s, 1 H), 7.88(d, 2 H), 7.58(m, 4 H), 6.81(m, 2 H), 5.85(br, 1 H, —OH), 5.37(q, 1 H), 4.77(d, 1 H, J = 14.3 Hz), 3.57(d, 1 H, J = 14.2 Hz), 3.17(d, 2 H, J = 6.5 Hz), 1.85(m, 1 H), 1.47(q, 4 H), 1.38(d, 3 H, J = 6.8 Hz), 0.87(t, 6 H) |
| 309 | [indazol-5-yl-NH-CH$_2$-cyclohexyl] | 7.98(s, 1 H), 7.89(s, 1 H), 7.54(m, 2 H), 7.42(d, 1 H), 6.89(m, 2 H), 6.81(m, 2 H), 6.09(br, 1 H), 5.33(q, 1 H), 5.33(d, 1 H), 4.74(d, 1 H), 3.53(d, 1 H), 3.01(d, 2 H), 1.86(m, 4 H), 1.35(d, 3 H), 1.23(m, 3 H), 1.03(m, 3 H) |
| 310 | [indazol-5-yl-N(CH$_3$)$_2$] | 8.06(s, 1 H), 7.88(d, 2 H), 7.58(m, 4 H), 6.81(m, 2 H), 5.85(br, 1 H, —OH), 5.37(q, 1 H), 4.77(d, 1 H, J = 14.3 Hz), 3.57(d, 1 H, J = 14.2 Hz), 2.85(s, 6 H) |
| 311 | [indazol-5-yl-N(isobutyl)$_2$] | 7.97(s, 1 H), 7.90(s, 1 H), 7.54(m, 2 H), 7.42(d, 1 H), 7.14(d, 1 H), 6.82(m, 3 H), 6.14(br, 1 H), 5.32(q, 1 H), 4.75(d, 1 H), 3.54(d, 1 H), 3.13(d, 2 H), 2.05(m, 4 H), 1.35(d, 3 H), 0.93(d, 14 H) |

TABLE 6-continued

| Ex. | Het | ¹H-NMR(300 MHz, CDCl₃) δ |
|---|---|---|
| 312 | (structure: indazole-N(CH₂CH₂CH(CH₃)₂)₂) | 7.97(s, 1 H), 7.90(s, 1 H), 7.56(m, 2 H), 7.43(m, 1 H), 7.11(m, 1 H), 6.84(m, 3 H), 6.15(br, 1 H, —OH), 5.34(m, 1 H), 4.75(d, 1 H, J = 14.9 Hz), 3.55(d, 1 H, J = 14.3 Hz), 3.30(t, 4 H), 1.63(m, 2 H), 1.47(m, 4 H), 1.35(d, 3 H, J = 6.8 Hz), 0.95 (d, 12 H) |
| 313 | (structure: indazole-N(CH₂CH(Et)₂)₂) | 7.97(s, 1 H), 7.91(s, 1 H), 7.55(m, 2 H), 7.41(d, 1 H), 7.13(m, 1 H), 6.89(s, 1 H), 6.82(m, 2 H), 6.17(br, 1 H, —OH), 5.33(q, 1 H), 4.76(d, 1 H, J = 14.3 Hz), 3.68(d, 1 H, J = 14.2 Hz), 3.19(d, 4 H, J = 7.0 Hz), 1.71(m, 2 H), 1.34(m, 12 H), 0.89(t, 12 H) |
| 314 | (structure: indazole-N(CH₂-cyclohexyl)₂) | 7.97(s, 1 H), 7.91(s, 1 H), 7.55(m, 2 H), 7.41(d, 1 H), 7.09(d, 1 H), 6.81(m, 3 H), 6.16(br, 1 H), 5.32(q, 1 H), 4.75(d, 1 H), 3.55(d, 1 H), 3.15(d, 4 H), 1.73(m, 10 H), 1.34(d, 3 H), 1.15(m, 6 H), 0.91 (m, 4 H) |

Example 315

(2R,3R)-3-(5-((4-chlorobenzyl)(ethyl)amino)-1H-indazol-2-yl)-2-(2,4-difluorophenyl)-1-(1H-1,2,4-triazol-1-yl)butan-2-ol To a solution of (2R,3R)-3-(5-(4-chlorobenzylamino)-1H-indazol-2-yl)-2-(2,4-difluorophenyl)-1-(1H-1,2,4-triazol-1-yl)butan-2-ol (0.043 g, 0.08 mmol), prepared in Example 244, in N,N'-dimethylformamide (0.5 ml) was added diisopropylethylamine (0.015 ml, 0.08 mmol), followed by stirring for 30 min. The reaction solution was further stirred at 80° C. for 18 hours after the addition of bromoethane (0.019 ml, 0.17 mmol) thereto. The reaction product was diluted with ethyl acetate (10 ml) and washed with saturated ammonium chloride solution (10 ml), and then with brine (10 ml). The organic layer was dried over anhydrous magnesium sulfate and concentrated using vacuum evaporation. The crude product was purified by chromatography on silica gel to give the title compound.

¹H-NMR (300 MHz, CDCl₃) δ 7.91 (d, 2H), 7.56 (m, 2H), 7.41 (m, 2H), 7.28 (m, 2H), 6.98 (m, 1H), 6.82 (m, 4H), 6.11 (br, 1H, —OH), 4.74 (d, 1H, 0=14.2 Hz), 4.38 (s, 2H), 3.54 (d, 1H, J=14.2 Hz), 3.39 (q, 2H), 1.35 (d, 3H, J=6.8 Hz), 1.13 (t, 3H).

Examples 316 to 346

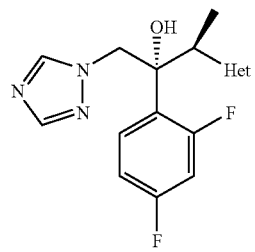

Compounds of the chemical formula above, wherein Het is as listed in Table 7 below, were synthesized according to procedures similar to that of Example 315.

TABLE 7

| Ex. | Het | ¹H-NMR(300 MHz, CDCl₃) δ |
|---|---|---|
| 316 | 1H-indazol-5-yl with N(iPr)(CH₂-4-ClC₆H₄) | 7.91(d, 2 H), 7.56(m, 2 H), 7.41(m, 2 H), 7.28(m, 2 H), 6.98(m, 1 H), 6.82(m, 4 H), 6.11(br, 1 H, —OH), 4.74(d, 1 H, J = 14.2 Hz), 4.38(s, 2 H), 3.54 (d, 1 H, J = 14.2 Hz), 2.97(m, 1 H), 1.35(d, 3 H, J = 6.8 Hz), 1.18(d, 6 H) |
| 317 | 1H-indazol-5-yl with N(n-Pr)(CH₂-4-ClC₆H₄) | 7.91(d, 2 H), 7.56(m, 2 H), 7.41(m, 2 H), 7.28(m, 2 H), 6.98(m, 1 H), 6.82(m, 4 H), 6.11(br, 1 H, —OH), 4.74(d, 1 H, J = 14.2 Hz), 4.38(s, 2 H), 3.54(d, 1 H, J = 14.2 Hz), 3.35(m, 2 H), 1.35(d, 3 H, J = 6.8 Hz), 1.56(m, 2 H), 0.96(t, 3 H) |
| 318 | 1H-indazol-5-yl with N(iBu)(CH₂-4-ClC₆H₄) | 7.91(d, 2 H), 7.56(m, 2 H), 7.41(m, 2 H), 7.28(m, 2 H), 6.98(m, 1 H), 6.82(m, 4 H), 6.11(br, 1 H, —OH), 4.74(d, 1H, J = 14.2 Hz), 4.38(s, 2 H), 3.54(d, 1 H, J = 14.2 Hz), 3.31(m, 2 H), 2.07(m, 1 H), 1.35(d, 3 H, J = 6.8 Hz), 1.01(d, 6 H) |
| 319 | 1H-indazol-5-yl with N(isopentyl)(CH₂-4-ClC₆H₄) | 7.91(d, 2 H), 7.56(m, 2 H), 7.41(m, 2 H), 7.28(m, 2 H), 6.98(m, 1 H), 6.82(m, 4 H), 6.11(br, 1 H, —OH), 4.74(d, 1 H, J = 14.2 Hz), 4.38(s, 2 H), 3.54(d, 1 H, J = 14.2 Hz), 3.35(m, 2 H), 1.83(m, 1 H), 1.48(m, 2 H), 1.35(d, 3 H, J = 6.8 Hz), 1.01(d, 6 H) |
| 320 | 1H-indazol-5-yl with N(2-ethylbutyl)(CH₂-4-ClC₆H₄) | 7.91(d, 2 H), 7.56(m, 2 H), 7.41(m, 2 H), 7.28(m, 2 H), 6.98(m, 1 H), 6.82(m, 4 H), 6.11(br, 1 H, —OH), 4.74(d, 1 H, J = 14.2 Hz), 4.38(s, 2 H), 3.54(d, 1 H, J = 14.2 Hz), 3.31(d, 2 H), 1.71(m, 1 H), 1.35(d, 3 H, J = 6.8 Hz), 1.29(m, 4 H), 0.96(t, 6 H) |
| 321 | 2H-indazol-5-yl with N(2-ethylhexyl)(CH₂-4-ClC₆H₄) | 7.91(d, 2 H), 7.56(m, 2 H), 7.41(m, 2 H), 7.28(m, 2 H), 6.98(m, 1 H), 6.82(m, 4 H), 6.11(br, 1 H, —OH), 4.74(d, 1 H, J = 14.2 Hz), 4.38(s, 2 H), 3.54(d, 1 H, J = 14.2 Hz), 3.31(d, 2 H), 1.71(m, 1 H), 1.35(d, 3 H, J = 6.8 Hz), 1.33(m, 4 H), 1.29(m, 4 H), 0.96(t, 6 H) |

TABLE 7-continued

| Ex. | Het | $^1$H-NMR(300 MHz, CDCl$_3$) δ |
|---|---|---|
| 322 | indazol-5-yl-N(cyclopentyl)(4-chlorobenzyl) | 7.91(d, 2 H), 7.56(m, 2 H), 7.41(m, 2 H), 7.28(m, 2 H), 6.98(m, 1 H), 6.82(m, 4 H), 6.11(br, 1 H, —OH), 4.74(d, 1 H, J = 14.2 Hz), 4.38(s, 2 H), 3.54(d, 1 H, J = 14.2 Hz), 2.64(m, 1 H), 1.83(m, 3 H), 1.56(m, 3 H), 1.48(m, 2 H), 1.35(d, 3 H, J = 6.8 Hz) |
| 323 | indazol-5-yl-N(cyclohexylmethyl)(4-chlorobenzyl) | 7.91(d, 2H), 7.56(m, 2 H), 7.41(m, 2 H), 7.28(m, 2 H), 6.98(m, 1 H), 6.82(m, 4 H), 6.11(br, 1 H, —OH), 4.74(d, 1 H, J = 14.2 Hz), 4.38(s, 2 H), 3.54(d, 1 H, J = 14.2 Hz), 3.31(d, 2 H), 1.67~1.39(m, 10 H), 1.35(d, 3 H, J = 6.8 Hz) |
| 324 | indazol-5-yl-N(tert-butyl)(4-chlorobenzyl) | 7.91(d, 2 H), 7.56(m, 2 H), 7.41(m, 2 H), 7.28(m, 2 H), 6.98(m, 1 H), 6.82(m, 4 H), 6.11(br, 1 H, —OH), 4.74(d, 1 H, J = 14.2 Hz), 4.38(s, 2 H), 3.54(d, 1 H, J = 14.2 Hz), 1.35(d, 3 H, J = 6.8 Hz), 1.23(s, 9 H) |
| 325 | indazol-5-yl-N(2-hydroxyethyl)(4-chlorobenzyl) | 7.91(d, 2 H), 7.56(m, 2 H), 7.41(m, 2 H), 7.28(m, 2 H), 6.98(m, 1 H), 6.82(m, 4 H), 6.11(br, 1 H, —OH), 4.74(d, 1 H, J = 14.2 Hz), 4.38(s, 2 H), 3.54(d, 1 H, J = 14.2 Hz), 3.39(q, 2 H), 1.35(d, 3 H, J = 6.8 Hz), 1.28(t, 3 H) |
| 326 | indazol-5-yl-N(sec-butyl)(4-chlorobenzyl) | 7.91(d, 2 H), 7.56(m, 2 H), 7.41(m, 2 H), 7.28(m, 2 H), 6.98(m, 1 H), 6.82(m, 4 H), 6.11(br, 1 H, —OH), 4.74(d, 1 H, J = 14.2 Hz), 4.38(s, 2 H), 3.54(d, 1 H, J = 14.2 Hz), 1.35(d, 3 H, J = 6.8 Hz) |
| 327 | indazol-5-yl-N(tert-pentyl)(4-chlorobenzyl) | 7.91(d, 2 H), 7.56(m, 2 H), 7.41(m, 2 H), 7.28(m, 2 H), 6.98(m, 1 H), 6.82(m, 4 H), 6.11(br, 1 H, —OH), 4.74(d, 1 H, J = 14.2 Hz), 4.38(s, 2 H), 3.54(d, 1 H, J = 14.2 Hz), 2.79(m, 1 H), 1.52(m, 2 H), 1.35(d, 3 H, J = 6.8 Hz), 1.23(d, 3 H), 0.96(t, 3 H) |

TABLE 7-continued

| Ex. | Het | $^1$H-NMR(300 MHz, CDCl$_3$) δ |
|---|---|---|
| 328 | (indazole-N-benzyl(4-Cl)-N-propyl-1,3-dioxolane) | 7.91(d, 2 H), 7.56(m, 2 H), 7.41(m, 2 H), 7.28(m, 2 H), 6.98(m, 1 H), 6.82(m, 4 H), 6.11(br, 1 H, —OH), 4.89(m, 1 H), 4.74(d, 1 H, J = 14.2 Hz), 4.38(s, 2 H), 3.94(m, 4 H), 3.54(d, 1 H, J = 14.2 Hz), 3.35 (m, 2 H), 1.82(m, 2 H), 1.35(d, 3 H, J = 6.8 Hz) |
| 329 | (indazole-N-benzyl(4-Cl)-N-propyl-1,3-dioxane) | 7.91(d, 2 H), 7.56(m, 2 H), 7.41(m, 2 H), 7.28(m, 2 H), 6.98(m, 1 H), 6.82(m, 4 H), 6.11(br, 1 H, —OH), 4.89(m, 1 H), 4.74(d, 1 H, J = 14.2 Hz), 4.38(s, 2 H), 3.94(m, 6 H), 3.54(d, 1 H, J = 14.2 Hz), 3.35(m, 2 H), 1.82(m, 2 H), 1.35(d, 3 H, J = 6.8 Hz) |
| 330 | (indazole-N-benzyl(4-Cl)-N-(3-hydroxypropyl)) | 7.91(d, 2 H), 7.56(m, 2 H), 7.41(m, 2 H), 7.28(m, 2 H), 6.98(m, 1 H), 6.82(m, 4 H), 6.11(br, 1 H, —OH), 4.74(d, 1 H, J = 14.2 Hz), 4.38(s, 2 H), 3.54(d, 1 H, J = 14.2 Hz), 3.53(m, 2 H), 3.35(m, 2 H), 1.71(m, 2 H), 1.35(d, 3 H, J = 6.8 Hz) |
| 331 | (indazole-N,N-dipropyl) | 8.23(s, 1 H), 7.90(s, 1 H), 7.58(m, 3 H), 7.41(m, 1 H), 7.12(m, 1 H), 6.81(m, 2 H), 6.15(br, 1 H), 5.33(m, 1 H), 4.75(d, 1 H), 3.55(d, 1 H), 3.13(m, 4 H), 2.04(m, 1 H), 1.53(m, 2 H), 1.36(d, 3 H), 0.92(m, 9 H) |
| 332 | (indazole-N-neopentyl-N-isobutyl) | 8.23(s, 1 H), 7.90(s, 1 H), 7.58(m, 3 H), 7.41(m, 1 H), 7.12(m, 1 H), 6.81(m, 2 H), 6.15(br, 1 H), 5.33(m, 1 H), 4.75(d, 1 H), 3.55(d, 1 H), 3.31(d, 2H), 3.27(s, 2 H), 2.07(m, 1 H), 1.36(d, 3 H), 1.06(s, 9 H), 1.01(d, 6 H) |

TABLE 7-continued
| Ex. | Het | ¹H-NMR(300 MHz, CDCl₃) δ |
|---|---|---|
| 333 | 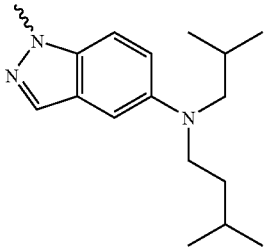 | 7.90(s, 1 H), 7.56(m, 4 H), 7.11(m, 1 H), 6.83(m, 3 H), 6.15(br, 1 H), 5.32(m, 1 H), 4.75(d, 1 H), 3.53(d, 1 H), 3.33(m, 2 H), 3.08(m, 2 H), 2.02(m, 1 H), 1.57(m, 1 H), 1.36(m, 2 H), 1.34(d, 3 H), 0.90(d, 6 H), 0.89(d, 6 H) |
| 334 | 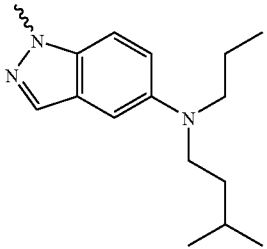 | 8.23(s, 1 H), 7.90(s, 1 H), 7.58(m, 3 H), 7.41(m, 1 H), 7.12(m, 1 H), 6.81(m, 2 H), 6.15(br, 1 H), 5.33(m, 1 H), 4.75(d, 1 H), 3.55(d, 1 H), 3.35(m, 4 H), 1.83(m, 1 H), 1.48(m, 4 H), 1.36(d, 3 H), 1.01(m, 9 H) |
| 335 | 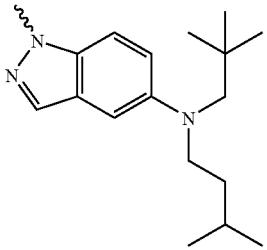 | 8.23(s, 1 H), 7.90(s, 1 H), 7.58(m, 3 H), 7.41(m, 1 H), 7.12(m, 1 H), 6.81(m, 2 H), 6.15(br, 1 H), 5.33(m, 1 H), 4.75(d, 1H), 3.55(d, 1 H), 3.35(m, 2 H), 3.27(s, 2H), 1.83(m, 1 H), 1.48(m, 2 H), 1.36(d, 3 H), 1.06(s, 9 H), 1.01(d, 6 H) |
| 336 | 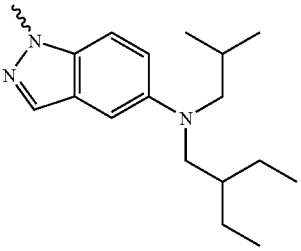 | 7.98(s, 1 H), 7.91(s, 1 H), 7.59(s, 2 H), 7.39(m, 1 H), 7.14(m, 1 H), 6.80(m, 3 H), 6.14(br, 1 H), 5.33(m, 1 H), 4.77(d, 1 H), 3.58(d, 1 H), 3.16(m, 4 H), 3.13(m, 2 H), 2.05(m, 1 H), 1.72(m, 1 H), 1.65(m, 4 H), 1.43(d, 3 H), 0.89(m, 12 H) |
| 337 | 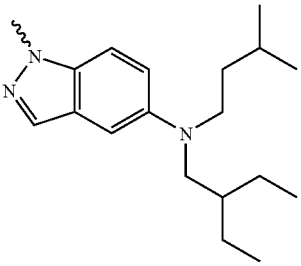 | 7.97(s, 1 H), 7.90(s, 1 H), 7.56(m, 2 H), 7.42(m, 1 H), 7.12(m, 1 H), 6.82(m, 3 H), 6.15(br, 1 H), 5.33(m, 1 H), 4.75(d, 1 H), 3.55(d, 1 H), 3.32(m, 2 H), 3.13(m, 2 H), 1.67(m, 2 H), 1.43(m, 6 H), 1.34(d, 3 H), 0.93(m, 12 H) |
| 338 | 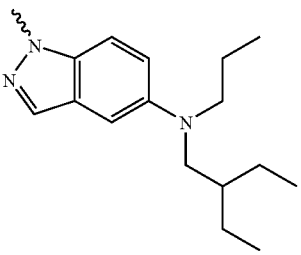 | 7.97(s, 1 H), 7.90(s, 1 H), 7.56(m, 3 H), 7.40(m, 1 H), 7.12(m, 1 H), 6.8(m, 2 H), 6.15(br, 1 H), 5.33(m, 1 H), 4.75(d, 1 H), 3.55(d, 1 H), 3.27(m, 2 H), 3.17(m, 2 H), 1.68(m, 1 H), 1.59(m, 2 H), 1.42(m, 4 H), 1.34(d, 3 H), 0.91(t, 9 H) |

TABLE 7-continued
| Ex. | Het | $^1$H-NMR(300 MHz, CDCl$_3$) δ |
|---|---|---|
| 339 | 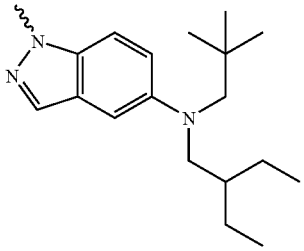 | 8.23(s, 1 H), 7.90(s, 1 H), 7.58(m, 3 H), 7.41(m, 1 H), 7.12(m, 1 H), 6.81(m, 2 H), 6.15(br, 1 H), 5.33(m, 1 H), 4.75(d, 1 H), 3.55(d, 1 H), 3.31(d, 2 H), 3.27(s, 2 H), 1.71(m, 1 H), 1.36(d, 3 H), 1.29(m, 4 H), 1.06(s, 9 H), 1.01(m, 6 H) |
| 340 | 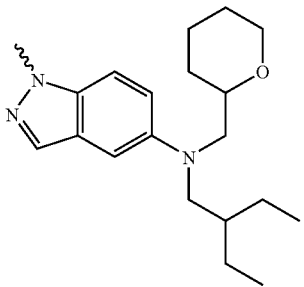 | 8.23(s, 1 H), 7.90(s, 1 H), 7.58(m, 3 H), 7.41(m, 1 H), 7.12(m, 1 H), 6.81(m, 2 H), 6.15(br, 1 H), 5.33(m, 1 H), 4.75(d, 1 H), 3.55(d, 1 H), 1.36(d, 3 H) |
| 341 | 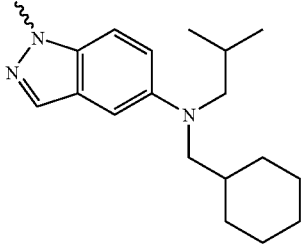 | 8.23(s, 1 H), 7.90(s, 1 H), 7.58(m, 3 H), 7.41(m, 1 H), 7.12(m, 1 H), 6.81(m, 2 H), 6.15(br, 1 H), 5.33(m, 1 H), 4.75(d, 1 H), 3.55(d, 1 H), 3.31(m, 4 H), 2.07(m, 1 H), 1.67(m, 1 H), 1.52~1.43(m, 10 H), 1.36(d, 3 H), 1.01(d, 6 H) |
| 342 | 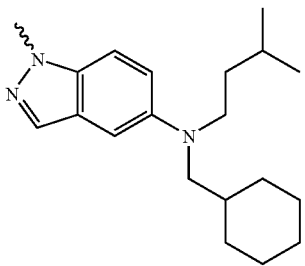 | 7.97(s, 1 H), 7.90(s, 1 H), 7.59(m, 3 H), 7.40(m, 1 H), 7.10(m, 1 H), 6.81(m, 2 H), 6.15(br, 1 H), 5.36(m, 1 H), 4.78(d, 1 H), 3.55(d, 1 H), 3.33(m, 2 H), 3.1(m, 2 H), 1.71(m, 6 H), 1.48(m, 2 H), 1.36(d, 3 H), 1.21(m, 4 H), 0.96(m, 5 H), 0.85(d, 3 H) |
| 343 | 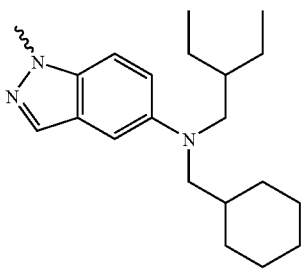 | 8.17(s, 1 H), 7.91(s, 1H), 7.93(m, 2 H), 7.18(m, 2 H), 6.87(m, 3 H), 5.35(m, 1 H), 4.79(d, 1 H), 3.64(d, 1 H), 3.19(m, 4 H), 1.86(m, 6 H), 1.38(d, 3 H), 1.15(m, 8 H), 0.83(m, 8 H) |

TABLE 7-continued

| Ex. | Het | ¹H-NMR(300 MHz, CDCl₃) δ |
|---|---|---|
| 344 | (indazole-N-propyl-N-cyclohexylmethyl structure) | 7.97(s, 1 H), 7.91(s, 1 H), 7.57(m, 2 H), 7.38(m, 1 H), 7.09(m, 1 H), 6.80(m, 3 H), 6.15(br, 1 H), 5.34(m, 1 H), 4.77(d, 1 H), 3.54(d, 1 H), 3.28(m, 2 H), 3.13(m, 2 H), 1.82(m, 7 H), 1.34(d, 3 H), 1.19(m, 4 H), 0.89(m, 5 H) |
| 345 | (indazole-N-neopentyl-N-cyclohexylmethyl structure) | 8.23(s, 1 H), 7.90(s, 1 H), 7.58(m, 3 H), 7.41(m, 1 H), 7.12(m, 1 H), 6.81(m, 2 H), 6.15(br, 1 H), 5.33(m, 1 H), 4.75(d, 1 H), 3.55(d, 1 H), 3.31(m, 4 H), 1.67(m, 1 H), 152~1.43(m, 10 H), 1.36(d, 3 H), 1.01(s, 9 H) |
| 346 | (indazole-N-(tetrahydropyranylmethyl)-N-cyclohexylmethyl structure) | 8.23(s, 1 H), 7.90(s, 1 H), 7.58(m, 3 H), 7.41(m, 1 H), 7.12(m, 1 H), 6.81(m, 2 H), 6.15(br, 1 H), 5.33(m, 1 H), 4.75(d, 1 H), 3.83(m, 1 H), 3.61(m, 2 H), 3.55(d, 1 H), 3.31(m, 2 H), 1.67(m, 1 H), 1.62~1.35(m, 18 H), 1.36(d, 3 H) |

Example 347 tert-Butyl 4-(1-((2R,3R)-3-(2,4-difluorophenyl)-3-hydroxy-4-(1H-1,2,4-triazol-1-yl)butan-2-yl)-1H-indazol-5-ylamino)piperidine-1-carboxylate To a solution of (2R,3R)-3-(5-amino-1H-indazol-1-yl)-2-(2,4-difluorophenyl)-1-(1H-1,2,4-triazol-1-yl)butan-2-ol (0.419 g, 1.09 mmol) and tert-butyl 4-oxo-1-piperidine carboxylate (0.22 g, 1.09 mmol) in absolute ethanol (2 ml) was added titanium (IV) isopropoxide (0.358 ml, 1.20 mmol), and the solution was stirred at room temperature for 2 hours. The addition of sodium cyanotrihydridoborate (0.137 g, 2.18 mmol) to the solution was followed by stirring at room temperature for 18 hours. The reaction was terminated by adding 10% sodium hydroxide solution (2 ml) before extraction with dichloromethane (20 ml). The organic layer was dried over anhydrous magnesium sulfate and evaporated in a vacuum to concentrate it. The crude product was purified by chromatography on silica gel to give the title compound (Yield 52%).

¹H-NMR (300 MHz, CDCl₃) δ 8.08 (s, 1H), 7.88 (s, 1H), 7.55 (m, 5H), 6.82 (m, 2H), 6.00 (br, 1H), 5.37 (q, 1H), 4.72 (d, 1H), 4.08 (m, 2H), 3.59 (d, 1H), 3.29 (m, 1H), 2.31 (m, 2H), 2.2 (m, 2H), 1.82 (m, 2H), 1.47 (s, 9H), 1.36 (d, 3H).

Examples 348 to 367

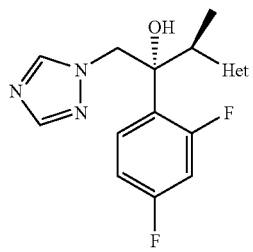

Procedures similar to that of Example 347 were conducted to synthesize the compound of the chemical formula above, Het being as listed in Table 8 below.

TABLE 8

| Ex. | Het | ¹H-NMR(300 MHz, CDCl₃) δ |
|---|---|---|
| 348 | indazol-1-yl-NH-piperidin-4-yl (NH) | 8.12(s, 1 H), 8.02(s, 1 H), 7.57(m, 2 H), 7.50(d, 1 H, J = 9.0 Hz), 7.42(s, 1 H), 7.17(dd, 1 H), 6.83(m, 2 H), 6.01(br, 1 H), 5.37(q, 1 H), 4.77(d, 1 H, J = 15.1 Hz), 4.06(m, 2 H), 3.78(m, 2 H), 3.60(d, 1 H, J = 14.2 Hz), 2.26(d, 2 H, J = 13.2 Hz), 2.02(m, 2 H), 1.29(d, 3 H, J = 6.8 Hz) |
| 349 | indazol-1-yl-NH-tetrahydropyran-4-yl | 8.02(s, 1 H), 7.91(s, 1 H), 7.57(m, 2 H), 7.50(d, 1 H, J = 9.0 Hz), 7.42(s, 1 H), 7.17(dd, 1 H), 6.83(m, 2 H), 6.01(br, 1 H), 5.37(q, 1 H), 4.77(d, 1 H, J = 15.1 Hz), 4.06(m, 2 H), 3.78(m, 2 H), 3.60(d, 1 H, J = 14.2 Hz), 2.26(d, 2 H, J = 13.2 Hz), 2.02(m, 2 H), 1.40(d, 3 H, J = 6.8 Hz) |
| 350 | indazol-2-yl-NH-tetrahydropyran-4-yl | 8.07(s, 1 H), 7.91(s, 1 H), 7.57(m, 2 H), 7.50(d, 1 H, J = 9.0 Hz), 7.42(s, 1 H), 7.17(dd, 1 H), 6.83(m, 2 H), 6.01(br, 1 H), 5.37(q, 1 H), 4.77(d, 1 H, J = 15.1 Hz), 4.06(m, 2 H), 3.78(m, 2 H), 3.60(d, 1 H, J = 14.2Hz), 2.26(d, 2 H, J = 13.2 Hz), 2.02(m, 2 H), 1.38(d, 3 H, J = 6.8 Hz) |
| 351 | indazol-1-yl-NH-tetrahydrothiopyran-4-yl | 8.06(s, 1 H), 7.84(m, 1 H), 7.50(m, 1 H), 6.97(m, 1 H), 6.76(m, 4 H), 5.34(q, 1 H), 4.75(d, 1 H), 3.55(d, 1 H), 3.30(m, 1 H), 2.63(m, 4 H), 2.44(m, 2 H), 1.83(m, 2 H) |
| 352 | indazol-2-yl-NH-cyclopentyl | 7.95(s, 1 H), 7.89(s, 1 H), 7.53(m, 2 H), 7.37(d, 1 H, J = 9.0 Hz), 6.90(dd, 1 H), 6.81(m, 3 H), 6.14(s, 1 H, —OH), 5.30(q, 1 H), 4.73(d, 1 H, J = 14.2 Hz), 3.81(m, 1 H), 3.55(d, 1 H, J = 14.2 Hz), 2.06(m, 2 H), 1.72(m, 4 H), 1.67(m, 2 H), 1.34(d, 3 H, J = 6.8 Hz) |
| 353 | indazol-1-yl-NH-cyclopentyl | 8.08(s, 1 H), 7.89(s, 1 H), 7.53(m, 2 H), 7.37(d, 1 H, J = 9.0Hz), 6.90(dd, 1 H), 6.81(m, 3 H), 6.14(s, 1 H, —OH), 5.30(q, 1 H), 4.73(d, 1 H, J = 14.2 Hz), 3.81(m, 1 H), 3.55(d, 1 H, J = 14.2 Hz), 2.06(m, 2 H), 1.72(m, 4 H), 1.67(m, 2 H), 1.32(d, 3 H, J = 6.8 Hz) |
| 354 | indazol-1-yl-NH-(1-ethylpiperidin-4-yl) | 8.12(s, 1 H), 8.02(s, 1 H), 7.57 (m, 2 H), 7.50(d, 1 H, J = 9.0 Hz), 7.42(s, 1 H), 7.17(dd, 1 H), 6.83(m, 2 H), 6.01(br, 1 H), 5.37(q, 1 H), 4.77(d, 1 H, J = 15.1 Hz), 4.06(m, 2 H), 3.78(m, 2 H), 3.60(d, 1 H, J = 14.2 Hz), 2.40(q, 2 H), 2.26(d, 2 H, J = 13.2 Hz), 2.02(m, 2 H), 1.29(d, 3 H, J = 6.8 Hz), 1.00(t, 3 H) |
| 355 | indazol-1-yl-NH-(1-acetylpiperidin-4-yl) | 8.12(s, 1 H), 8.02(s, 1 H), 7.57(m, 2 H), 7.50(d, 1 H, J = 9.0 Hz), 7.42(s, 1 H), 7.17(dd, 1 H), 6.83(m, 2 H), 6.01(br, 1 H), 5.37(q, 1 H), 4.77(d, 1 H, J = 15.1 Hz), 4.06(m, 2 H), 3.78(m, 2 H), 3.60(d, 1 H, J = 14.2 Hz), 2.26(d, 2 H, J = 13.2 Hz), 2.02(m, 2 H), 2.01(s, 3 H), 1.29(d, 3 H, J = 6.8 Hz) |
| 356 | indazol-1-yl-NH-(1-isopropylpiperidin-4-yl) | 8.12(s, 1 H), 8.02(s, 1 H), 7.57(m, 2 H), 7.50(d, 1 H, J = 9.0 Hz), 7.42(s, 1 H), 7.17(dd, 1 H), 6.83(m, 2 H), 6.01(br, 1 H), 5.37(q, 1 H), 4.77(d, 1 H, J = 15.1 Hz), 4.06(m, 2 H), 3.78(m, 2 H), 3.60(d, 1 H, J = 14.2 Hz), 2.97(m, 1 H), 2.26(d, 2 H, J = 13.2 Hz), 2.02(m, 2 H), 1.29(d, 3 H, J = 6.8 Hz), 1.05(d, 6H) |

TABLE 8-continued

| Ex. | Het | $^1$H-NMR(300 MHz, CDCl$_3$) δ |
|---|---|---|
| 357 | | 7.96 (m, 1 H), 7.89(s, 1 H), 7.54(m, 2 H), 7.38(m, 1 H), 6.99(m, 1 H), 6.80(m, 3 H), 6.12(br, 1 H, —OH), 5.32(q, 1 H), 4.74(d, 1 H, J = 14.3 Hz), 3.55(d, 1 H, J = 14.1 Hz), 2.12(m, 1 H), 1.73~1.12(m, 10 H), 1.06(d, 3 H, J = 6.5 Hz) |
| 358 | | 7.93(s, 1 H), 7.89(s, 1 H), 7.52(m, 2 H), 7.36(d, 1 H, J = 9.0 Hz), 6.92(m, 1 H), 6.79(m, 3 H), 6.14(s, 1 H), 5.30(q, 1 H), 4.73(d, 1 H, J = 14.5 Hz), 3.54(d, 1 H, J = 14.5 Hz), 2.14(m, 1 H), 1.93(m, 1 H), 1.75(m, 3 H), 1.56(m, 1 H), 1.42(m, 1 H), 1.33(d, 1 H, J = 6.8 Hz), 1.22(m, 3 H), 0.86(d, 3 H, J = 6.5 Hz) |
| 359 | | 7.95(d, 1 H), 7.89(s, 1 H), 7.55(m, 2 H), 7.40(m, 1 H), 6.94(m, 1 H), 6.80(m, 3 H), 6.13(br, 1 H, —OH), 5.32(q, 1 H), 4.74(d, 1 H, J = 14.2 Hz), 3.55(d, 1 H, J = 14.2 Hz), 2.14(m, 1 H), 1.92~1.18(m, 12 H), 0.98(d, 3 H) |
| 360 | | 7.96(d, 1 H), 7.89(s, 1 H), 7.55(m, 2 H), 7.40(m, 1 H), 6.98(m, 1 H), 6.82(m, 3 H), 6.09(br, 1 H, —OH), 5.33(q, 1 H), 4.74(d, 1 H, J = 14.2 Hz), 3.59(m, 1 H), 3.57(d, 1 H, J = 14.7 Hz), 3.27(m, 1 H), 2.18~1.43(m, 7 H), 1.35(d, 3 H, J = 6.9 Hz), 0.85(d, 6 H) |
| 361 | | 7.94(s, 1 H), 7.90(s, 1 H), 7.55(m, 2 H), 7.37(m, 1 H), 6.94(m, 1 H), 6.80(m, 3 H), 6.14(br, 1 H), 5.32(q, 1 H), 4.74(d, 1 H, J = 14.2 Hz), 3.79(m, 1 H), 3.58(m, 2 H), 2.14(m, 1 H), 1.95(m, 2 H), 1.75(m, 4 H), 1.35(d, 3 H), 0.89(d, 6 H) |
| 362 | | 7.95(d, 1 H), 7.89(d, 1 H), 7.55(m, 2 H), 7.38(m, 1 H), 6.98(m, 1 H), 6.82(m, 3 H), 6.13(br, 1 H), 5.32(q, 1 H), 4.74(d, 1 H, J = 14.1 Hz), 3.53(m, 2 H), 3.21(m, 1 H), 1.98(m, 3 H), 1.80(m, 3 H), 1.58(m, 2 H), 1.35(d, 3 H), 0.85(s, 9 H) |
| 363 | | 7.98(d, 1 H), 7.89(d, 1 H), 7.56(m, 2 H), 7.44(m, 1 H), 7.23(m, 7 H), 6.81(m, 2 H), 6.13(br, 1 H), 5.34(q, 1 H), 4.75(d, 1 H, J = 14.6 Hz), 3.69(m, 2 H), 3.56(d, 1 H, J = 14.3 Hz), 2.51(m, 4 H), 1.95(m, 4 H), 1.36(d, 3 H, J = 6.9 Hz) |
| 364 | | 8.12(s, 1 H), 8.02(s, 1 H), 7.57(m, 2 H), 7.50(d, 1 H, J = 9.0 Hz), 7.42(s, 1 H), 7.17(dd, 1 H), 6.83(m, 2 H), 6.01(br, 1 H), 5.37(q, 1 H), 4.77(d, 1 H, J = 15.1 Hz), 4.06(m, 2 H), 3.78(m, 2 H), 3.60(d, 1 H, J = 14.2 Hz), 2.40(q, 2 H), 2.26(d, 2 H, J = 13.2 Hz), 2.02(m, 2 H), 1.32(d, 3 H, J = 6.8 Hz), 1.00(t, 3 H) |
| 365 | | 8.15(s, 1 H), 8.02(s, 1 H), 7.57(m, 2 H), 7.50(d, 1 H, J = 9.0 Hz), 7.42(s, 1 H), 7.17(dd, 1 H), 6.83(m, 2 H), 6.01(br, 1 H), 5.37(q, 1 H), 4.77(d, 1 H, J = 15.1 Hz), 4.06(m, 2 H), 3.78(m, 2 H), 3.60(d, 1 H, J = 14.2 Hz), 2.40(q, 2 H), 2.26(d, 2 H, J = 13.2 Hz), 2.02(m, 2 H), 1.29(d, 3 H, J = 6.8 Hz), 1.00(t, 3 H) |

TABLE 8-continued

| Ex. | Het | $^1$H-NMR(300 MHz, CDCl$_3$) δ |
|---|---|---|
| 366 | (structure: indazole-NH-piperidine-N-C(O)-phenyl) | 7.95(s, 1 H), 7.89(s, 1 H), 7.58–7.40(m, 9 H), 7.03(m, 1 H), 6.82(m, 2 H), 6.08(br, 1 H), 5.33(q, 1 H), 4.74(d, 1 H), 3.96(m, 1 H), 3.59(m, 2 H), 3.48(m, 1 H), 3.32(m, 2 H), 1.89(m, 2 H), 1.57(m, 2 H), 1.35(d, 3 H, J = 6.9 Hz) |
| 367 | (structure: indazole-NH-tetrahydrothiopyran dioxide) | 8.02(s, 1 H), 7.91(s, 1 H), 7.57(m, 2 H), 7.50(d, 1 H, J = 9.0 Hz), 7.42(s, 1 H), 7.17(dd, 1 H), 6.83(m, 2 H), 6.01(br, 1 H), 5.37(q, 1 H), 4.77(d, 1 H, J = 15.1 Hz), 4.06(m, 2 H), 3.78(m, 2 H), 3.60(d, 1 H, J = 14.2 Hz), 2.26(d, 2 H, J = 13.2 Hz), 2.02(m, 2 H), 1.39(d, 3 H, J = 6.8 Hz) |

Example 368

(2R,3R)-3-(5-(4-chlorobenzylamino)-3-methyl-2H-indazol-1-yl)-2-(2,4-difluorophenyl)-1-(1H-1,2,4-triazol-1-yl)butan-2-ol With the exception that (2R,3R)-3-(5-amino-3-methyl-2H-indazol-1-yl)-2-(2,4-difluorophenyl)-1-(1H-1,2,4-triazol-1-yl)butan-2-ol, obtained in Example 108, was used, the same procedure as in Example 9 was conducted to synthesize the title compound.

$^1$H-NMR (300 MHz, CDCl$_3$) δ 8.13 (s, 1H), 7.89 (s, 1H), 7.53 (d, 2H), 7.37 (d, 2H), 7.25 (m, 4H), 6.82 (m, 2H), 5.36 (m, 1H), 4.79 (d, 1H), 4.05 (s, 2H), 3.57 (d, 1H), 2.69 (s, 3H), 1.39 (d, 3H).

Examples 369 to 397

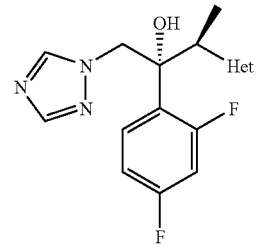

Procedures similar to that of Example 368 were conducted to synthesize compounds of the chemical formula above, Het being as listed in Table 9, below.

TABLE 9

| Ex. | Het | $^1$H-NMR(300 MHz, CDCl$_3$) δ |
|---|---|---|
| 369 | (3-methyl-2H-indazol-5-yl connected via N2, with NH-CH$_2$-4-fluorophenyl at 5-position) | 8.09(s, 1 H), 7.78(s, 1 H), 7.45(d, 2 H), 7.37(d, 2 H), 7.25(m, 4 H), 6.82(m, 2 H), 5.36(m, 1 H), 4.79(d, 1 H), 4.05(s, 2 H), 3.57(d, 1 H), 2.69(s, 3 H), 1.39(d, 3 H) |
| 370 | (3-methyl-1H-indazol-5-yl connected via N1, with NH-CH$_2$-4-fluorophenyl at 5-position) | 8.13(s, 1 H), 7.89(s, 1 H), 7.53(d, 2 H), 7.37(d, 2 H), 7.25(m, 4 H), 6.82(m, 2 H), 5.36(m, 1 H), 4.79(d, 1 H), 4.05(s, 2 H), 3.52(d, 1 H), 2.71(s, 3 H), 1.37(d, 3 H) |

TABLE 9-continued

| Ex. | Het | $^1$H-NMR(300 MHz, CDCl$_3$) δ |
|---|---|---|
| 371 | [3-methyl-1H-indazol-5-yl linked via N1 to CH$_2$-(4-chlorophenyl)NH-] | 8.13(s, 1 H), 7.91(s, 1 H), 7.53(d, 2 H), 7.37(d, 2 H), 7.25(m, 4 H), 6.82(m, 2 H), 5.36(m, 1 H), 4.79(d, 1 H), 4.05(s, 2 H), 3.57(d, 1 H), 2.69(s, 3 H), 1.35(d, 3 H) |
| 372 | [3-methyl-2H-indazol-5-yl linked via N2; NH-CH$_2$-(2,4-dichlorophenyl)] | 8.13(s, 1 H), 7.91(s, 1 H), 7.53(d, 2 H), 7.37(d, 2 H), 7.25(m, 3 H), 6.82(m, 2 H), 5.36(m, 1 H), 4.79(d, 1 H), 4.05(s, 2 H), 3.57(d, 1 H), 2.69(s, 3 H), 1.35(d, 3 H) |
| 373 | [3-methyl-1H-indazol-5-yl; NH-CH$_2$-(2,4-dichlorophenyl)] | 8.11(s, 1 H), 7.91(s, 1 H), 7.53(d, 2 H), 7.37(d, 2 H), 7.25(m, 3 H), 6.82(m, 2 H), 5.36(m, 1 H), 4.79(d, 1 H), 4.05(s, 2 H), 3.57(d, 1 H), 2.69(s, 3 H), 1.33(d, 3 H) |
| 374 | [3-methyl-2H-indazol-6-yl; NH-CH$_2$-(4-chlorophenyl)] | 8.12(s, 1 H), 7.89(s, 1 H), 7.53(d, 2 H), 7.37(d, 2 H), 7.25(m, 4 H), 6.82(m, 2 H), 5.36(m, 1 H), 4.79(d, 1 H), 4.05(s, 2 H), 3.57(d, 1 H), 2.69(s, 3 H), 1.39(d, 3 H) |
| 375 | [3-methyl-1H-indazol-6-yl; NH-CH$_2$-(4-chlorophenyl)] | 8.15(s, 1 H), 7.91(s, 1 H), 7.38(d, 2 H), 7.37(d, 2 H), 7.25(m, 4 H), 6.82(m, 3 H), 5.26(m, 1 H), 4.79(d, 1 H), 4.05(s, 2 H), 3.57(d, 1 H), 2.69(s, 3 H), 1.37(d, 3 H) |
| 376 | [7-fluoro-3-methyl-2H-indazol-5-yl; NH-CH$_2$-(4-chlorophenyl)] | 8.15(s, 1 H), 7.91(s, 1 H), 7.38(d, 1 H), 7.37(d, 2 H), 7.25(m, 4 H), 6.82(m, 2 H), 5.36(m, 1 H), 4.79(d, 1 H), 4.05(s, 2 H), 3.57(d, 1 H), 2.69(s, 3 H), 1.37(d, 3 H) |

TABLE 9-continued

| Ex. | Het | ¹H-NMR(300 MHz, CDCl₃) δ |
|---|---|---|
| 377 | (1H-indazol-1-yl, 7-fluoro-3-methyl-5-[(4-chlorobenzyl)amino]) | 8.18(s, 1 H), 7.91(s, 1 H), 7.38(d, 1 H), 7.37(d, 2 H), 7.25(m, 4 H), 6.82(m, 2 H), 5.36(m, 1 H), 4.79(d, 1 H), 4.05(s, 2 H), 3.57(d, 1 H), 2.69(s, 3 H), 1.35(d, 3 H) |
| 378 | (2H-indazol-2-yl, 7-chloro-3-methyl-5-[(4-chlorobenzyl)amino]) | 8.12(s, 1 H), 7.91(s, 1 H), 7.38(d, 1 H), 7.37(d, 2 H), 7.25(m, 4 H), 6.82(m, 2 H), 5.36(m, 1 H), 4.79(d, 1 H), 4.05(s, 2 H), 3.57(d, 1 H), 2.69(s, 3 H), 1.37(d, 3 H) |
| 379 | (1H-indazol-1-yl, 7-chloro-3-methyl-5-[(4-chlorobenzyl)amino]) | 8.14(s, 1 H), 7.91(s, 1 H), 7.38(d, 1 H), 7.37(d, 2 H), 7.25(m, 4 H), 6.82(m, 2 H), 5.36(m, 1 H), 4.79(d, 1 H), 4.05(s, 2 H), 3.57(d, 1 H), 2.69(s, 3 H), 1.35(d, 3 H) |
| 380 | (2H-indazol-2-yl, 6-fluoro-3-methyl-5-[(4-chlorobenzyl)amino]) | 8.15(s, 1 H), 7.91(s, 1 H), 7.38(d, 1 H), 7.37(d, 2 H), 7.25(m, 4 H), 6.82(m, 2 H), 5.36(m, 1 H), 4.79(d, 1 H), 4.05(s, 2 H), 3.57(d, 1 H), 2.69(s, 3 H), 1.37(d, 3 H) |
| 381 | (1H-indazol-1-yl, 6-fluoro-3-methyl-5-[(4-chlorobenzyl)amino]) | 8.18(s, 1 H), 7.91(s, 1 H), 7.38(d, 1 H), 7.37(d, 2 H), 7.25(m, 4 H), 6.82(m, 2 H), 5.36(m, 1 H), 4.79(d, 1 H), 4.05(s, 2 H), 3.57(d, 1 H), 2.69(s, 3 H), 1.35(d, 3 H) |
| 382 | (2H-indazol-2-yl, 3-ethyl-6-[(4-chlorobenzyl)amino]) | 8.12(s, 1 H), 7.89(s, 1 H), 7.53(d, 2 H), 7.37(d, 2 H), 7.25(m, 4 H), 6.82(m, 2 H), 5.36(m, 1 H), 4.79(d, 1 H), 4.05(s, 2 H), 3.61(q, 2 H), 3.57(d, 1 H), 2.69(s, 3 H), 1.39(d, 3 H) |
| 383 | (1H-indazol-1-yl, 3-ethyl-6-[(4-chlorobenzyl)amino]) | 8.15(s, 1 H), 7.91(s, 1 H), 7.38(d, 2 H), 7.37(d, 2 H), 7.25(m, 4 H), 6.82(m, 2 H), 5.36(m, 1 H), 4.79(d, 1 H), 4.05(s, 2 H), 3.69(q, 2 H), 3.57(d, 1 H), 2.69(s, 3 H), 1.37(d, 3 H) |

TABLE 9-continued

| Ex. | Het | $^1$H-NMR(300 MHz, CDCl$_3$) δ |
|---|---|---|
| 384 | 3-ethyl-2H-indazol-5-yl N-(4-chlorobenzyl), N2-substituted | 8.09(s, 1 H), 7.89(s, 1 H), 7.53(d, 2 H), 7.37(d, 2 H), 7.25(m, 4 H), 6.82(m, 2 H), 5.36(m, 1 H), 4.79(d, 1 H), 4.05(s, 2 H), 3.61(q, 2 H), 3.57(d, 1 H), 2.69(s, 3 H), 1.39(d, 3 H) |
| 385 | 3-ethyl-1H-indazol-5-yl N-(4-chlorobenzyl), N1-substituted | 8.11(s, 1 H), 7.91(s, 1 H), 7.38(d, 2 H), 7.37(d, 2 H), 7.25(m, 4 H), 6.82(m, 2 H), 5.36(m, 1 H), 4.79(d, 1 H), 4.05(s, 2 H), 3.69(q, 2 H), 3.57(d, 1 H), 2.69(s, 3 H), 1.37(d, 3 H) |
| 386 | 7-fluoro-3-ethyl-2H-indazol-5-yl N-(4-chlorobenzyl), N2-substituted | 8.15(s, 1 H), 7.91(s, 1 H), 7.38(d, 1 H), 7.37(d, 2 H), 7.25(m, 4 H), 6.82(m, 2 H), 5.36(m, 1 H), 4.79(d, 1 H), 4.05(s, 2 H), 3.57(d, 1 H), 2.71(s, 3 H), 1.37(d, 3 H) |
| 387 | 7-fluoro-3-ethyl-1H-indazol-5-yl N-(4-chlorobenzyl), N1-substituted | 8.18(s, 1 H), 7.91(s, 1 H), 7.38(d, 1 H), 7.37(d, 2 H), 7.25(m, 4 H), 6.82(m, 2 H), 5.36(m, 1 H), 4.79(d, 1 H), 4.05(s, 2 H), 3.57(d, 1 H), 2.73(s, 3 H), 1.35(d, 3 H) |
| 388 | 7-chloro-3-ethyl-2H-indazol-5-yl N-(4-chlorobenzyl), N2-substituted | 8.11(s, 1 H), 7.91(s, 1 H), 7.38(d, 1 H), 7.37(d, 2 H), 7.25(m, 4 H), 6.82(m, 2 H), 5.36(m, 1 H), 4.79(d, 1 H), 4.05(s, 2 H), 3.57(d, 1 H), 2.71(s, 3 H), 1.39(d, 3 H) |
| 389 | 7-chloro-3-ethyl-1H-indazol-5-yl N-(4-chlorobenzyl), N1-substituted | 8.13(s, 1 H), 7.93(s, 1 H), 7.41(d, 1 H), 7.37(d, 2 H), 7.25(m, 4 H), 6.82(m, 2 H), 5.36(m, 1 H), 4.79(d, 1 H), 4.05(s, 2 H), 3.57(d, 1 H), 2.73(s, 3 H), 1.37(d, 3 H) |
| 390 | 6-fluoro-3-ethyl-2H-indazol-5-yl N-(4-chlorobenzyl), N2-substituted | 8.15(s, 1 H), 7.91(s, 1 H), 7.38(d, 1 H), 7.37(d, 2 H), 7.25(m, 4 H), 6.82(m, 2 H), 5.36(m, 1 H), 4.79(d, 1 H), 4.05(s, 2 H), 3.57(d, 1 H), 2.71(s, 3 H), 1.37(d, 3 H) |

TABLE 9-continued

| Ex. | Het | $^1$H-NMR(300 MHz, CDCl$_3$) δ |
|---|---|---|
| 391 | (3-ethyl-6-fluoro-1H-indazol-5-yl)-(4-chlorobenzyl)amine structure | 8.18(s, 1 H), 7.91(s, 1 H), 7.38(d, 1 H), 7.37(d, 2 H), 7.25(m, 4 H), 6.82(m, 2 H), 5.36(m, 1 H), 4.79(d, 1 H), 4.05(s, 2 H), 3.57(d, 1 H), 2.73(s, 3 H), 1.35(d, 3 H) |
| 394 | N,N-bis(4-fluorobenzyl)-3-methyl-1H-indazol-5-amine structure | 8.13(s, 1 H), 7.97(s, 1 H), 7.54(d, 2 H), 7.4(d, 2 H), 7.32(s, 1 H), 6.82(m, 2 H), 6.08(br, 1 H), 5.36(m, 1 H), 4.76(d, 1 H), 4.19(s, 2 H), 3.58(d, 1 H), 2.61(s, 3 H), 1.38(d, 3 H) |
| 395 | N,N-bis(4-trifluoromethylbenzyl)-3-methyl-1H-indazol-5-amine structure | 8.11(s, 1 H), 7.97(s, 1 H), 7.54(d, 2 H), 7.4(d, 2 H), 7.3(s, 1 H), 6.82(m, 2 H), 6.08(br, 1 H), 5.35(m, 1 H), 4.76(d, 1 H), 4.19(s, 2 H), 3.58(d, 1 H), 2.61(s, 3 H), 1.36(d, 3 H) |
| 396 | N,N-bis(2,4-difluorobenzyl)-3-methyl-1H-indazol-5-amine structure | 8.05(s, 1 H), 7.93(s, 1 H), 7.56(m, 2 H), 7.36(m, 2 H), 6.81(m, 5 H), 5.33(m, 1 H), 4.75(d, 1 H), 4.23(s, 2 H), 3.55(d, 1 H), 2.47(s, 3 H), 1.36(d, 3 H) |

TABLE 9-continued

| Ex. | Het | $^1$H-NMR(300 MHz, CDCl$_3$) δ |
|---|---|---|
| 397 | (structure: 1H-indazol-3-methyl-5-yl linked via N to two 2,4-dichlorobenzyl groups) | 8.16(s, 1 H), 7.56(m, 3 H), 7.48(s, 2 H), 7.24(m, 3 H), 6.82(m, 3 H), 5.84(br, 1 H), 5.34(m, 1 H), 4.78(d, 1 H), 4.76(s, 2 H), 3.61(d, 1 H), 2.81(s, 3 H), 1.42(d, 3 H) |

Example 398

(2R,3R)-3-(5-(4-chlorobenzylamino)-1H-indazol-2-yl)-2-(2,4-difluorophenyl)-1-(1H-1,2,4-triazol-1-yl)butan-2-ol HCl (2R,3R)-3-(5-(4-chlorobenzylamino)-1H-indazol-2-yl)-2-(2,4-difluorophenyl)-1-(1H-1,2,4-triazol-1-yl)butan-2-ol (0.2 g), obtained in Example 245, was dissolved with a mixture of diethyl ether (2 ml) and ethyl acetate (0.2 ml) and hydrochloric acid gas was injected for 5 to 10 sec into the solution at 0° C. Following the addition of diethyl ether (10 ml), the reaction solution was stirred for 10 min at 0° C. and then for 30 min at room temperature. The product was filtered and dried in a vacuum to give the title compound (Yield 95%).

$^1$H-NMR (300 MHz, DMSO-d$_6$) δ 7.96 (s, 1H), 7.89 (s, 1H), 7.53 (m, 2H), 7.43 (d, 1H, J=9.0 Hz), 7.32 (m, 4H), 7.03 (d, 1H, J=8.6 Hz), 6.88 (br, 1H), 6.80 (m, 2H), 6.06 (br, 1H, —OH), 5.34 (q, 1H), 4.74 (d, 1H, J=15.2 Hz), 3.54 (d, 1H, J=14.2 Hz), 1.36 (d, 3H, J=6.8 Hz).

Formulation Example 1

Tablet (2R,3R)-3-(5-(4-chlorobenzylamino)-1H-indazol-2-yl)-2-(2,4-difluorophenyl)-1-(1H-1,2,4-triazol-1-yl)butan-2-ol (50 mg), prepared in Example 245, and magnesium stearate (20 mg) were granulated with soluble starch (35 mg). Then the granules were dried and mixed with lactose (65 mg) and corn starch (30 mg) for 30 min using a mechanical shaker and a mixer. The mixture was pressed into tablets.

Formulation Example 2

Liquids

A solution of (2R,3R)-3-(5-(4-chlorobenzylamino)-1H-indazol-2-yl)-2-(2,4-difluorophenyl)-1-(1H-1,2,4-triazol-1-yl)butan-2-ol hydrochloride (1 g), obtained in Example 398, and sodium chloride (9 g) in saline (1000 ml) was sterilized and filtered and the filtrate was charged into 50 ml vials for intravenous injection.

Test Example 1

Assay for Antifungal Activity

Fungal strains to be tested were inoculated onto Sabouraud dextrose agar, YM agar, and potato dextrose agar and cultured at 35° C. for two to three days. Individual single colonies of the yeast fungi selected out of the cultured strains were suspended in 5 ml of 0.85% sterile saline, followed by correction to adjust the absorbance thereof at 530 nm to 0.108. The suspensions were diluted serially by 1:50 and then 1:20 in RPMI 1640 media to prepare liquid inocula ranging in cell count from $1.0 \times 10^3$ to $5.0 \times 10^3$ CFU/ml. As for filamentous fungi, their spores were suspended in 0.85% sterile saline and the suspensions were corrected with sterile saline to show optical transmittance at 530 nm of 80 to 82%. A dilution of 1:50 was made with RPMI 1640 media to prepare liquid inocula having cell counts from $0.4 \times 10^2$ to $5 \times 10^4$ CFU/ml.

Antifungal samples were prepared by diluting the compounds of the present inventions in RPMI 1640 media to serial concentrations from 0.0625 to 32 μg/ml. As a vehicle, DMSO was contained in a final concentration of 1% (V/V) in the antifungal samples. 0.1 ml of each of the dilutions in series was added to equal volume of each of the fungal inocula.

At the concentrations provided, the fungi were observed with the naked eye for the growth of all yeasts except for *Cryptococcus neoformans* after 24 hours, and for the growth of filamentous fungi after 48 hours, and as well as using the growth indicator alamarBlue, concentrations of the compounds at which 90% of the fungi were inhibited compared to the negative control were determined.

All tests were conducted in duplicate for each test group, and the results are given in Table 10, below.

TABLE 10

In vitro Assay for Antifungal Activity (MIC$_{90}$ µg/ml)

| | Examples | | | | | | Fluconazole |
|---|---|---|---|---|---|---|---|
| | 50 | 56 | 60 | 72 | 100 | 106 | |
| Candida albicans ATCC 32033 | ≦0.015 | ≦0.015 | ≦0.015 | 0.031 | ≦0.015 | 0.031 | 1 |
| Candida glabrata ATCC 34138 | 2 | 2 | 2 | 8 | 8 | 8 | >32 |
| Candida krusei ATCC 6258 | 0.5 | 1 | 1 | 8 | 4 | 4 | >8 |
| Cryptococcus neoformans ATCC 4065 | 0.063 | 0.125 | 1 | 1 | 0.25 | 0.5 | 8 |
| Aspergillus fumigatus ATCC MYA-1163 | 4 | 0.5 | 0.5 | 4 | 16 | 8 | >128 |
| Aspergillus flavus ATCC MYA-1004 | 2 | 2 | 1 | 8 | 16 | 8 | >128 |
| Aspergillus terreus ATCC 28301 | 4 | 2 | 1 | 4 | 16 | 4 | >128 |
| Aspergillus niger ATCC 9142 | 8 | 2 | 1 | 8 | >16 | 16 | >128 |

| | Examples | | | | | | |
|---|---|---|---|---|---|---|---|
| | 234 | 244 | 245 | 247 | 250 | 309 | 310 |
| Candida albicans ATCC 32033 | ≦0.015 | ≦0.015 | ≦0.015 | ≦0.015 | ≦0.015 | ≦0.015 | 0.063 |
| Candida glabrata ATCC 34138 | 4 | 8 | 4 | 8 | 8 | 8 | 8 |
| Candida krusei ATCC 6258 | 0.5 | 0.5 | 0.5 | 0.5 | 0.5 | 1 | 1 |
| Cryptococcus neoformans ATCC 4065 | 0.125 | 0.25 | 0.125 | 0.25 | 0.25 | 0.5 | 0.5 |
| Aspergillus fumigatus ATCC MYA-1163 | 2 | 0.5 | 0.5 | 1 | 1 | 8 | 2 |
| Aspergillus flavus ATCC MYA-1004 | 1 | 0.5 | 0.5 | 1 | 0.5 | 2 | 1 |
| Aspergillus terreus ATCC 28301 | 2 | 1 | 0.5 | 2 | 2 | 4 | 2 |
| Aspergillus niger ATCC 9142 | 2 | 2 | 2 | 4 | 4 | 16 | 2 |

Test Examples 2

In Vivo Assay for Antifungal Activity

Azole compounds synthesized in Examples in accordance with the present invention were assayed for antifungal activity in vivo. *Candida albicans* (ATCC 36082) was grown in YM broth on a rotary shaker (200 rpm, 26° C.) for about 12 hours to a concentration of $2.5 \times 10^7$ CFU/ml and used to infect ICR mice at a dose of 0.2 ml/head via caudal veins. Suspensions or solutions of the azole compounds in a 25% beta-hydroxypropyl methylcellulose base were orally administered at a dose of 20 mg/kg to respective infected ICR mice in groups of 10, the condition and body weights of the mice were monitored, and autopsies were finally conducted. For a negative control, the vehicle alone was used while fluconazole was administered to a positive control. The mice were inoculated once with the fungal preparation on the day of commencement of the administration. The test materials of interest and the positive control material were orally administered to the inoculated mice once a day for seven days from day 0 to day 6, with the first oral administration made five hours after the fungal inoculation (day 0). The periods of time for which the infected mice lived were counted.

The number of mice which survived the fungal infection for 21 days following the inoculation was represented as % survival for each test group, and the results are given in Table 11, below. All members of the negative control were dead 8 days after the fungal infection, while all of the groups administered with Compound 50 were dead 18 days after the fungal infection.

TABLE 11

In vivo Assay for Antifungal Activity (% Survival on Day 21)

| Ex. 50 | Ex. 60 | Ex. 234 | Ex. 245 | Ex. 310 | Fluconazole | (—) Control |
|--------|--------|---------|---------|---------|-------------|-------------|
| 0%     | 10%    | 40%     | 40%     | 40%     | 20%         | 0%          |

Test Example 3

Assay for Cytotoxicity in Human Hepatocytes

The azole compounds synthesized in Examples in accordance with the present invention were assayed in vitro for cytotoxicity in human hepatocytes. HepG2 cells were aliquoted at a population of $5 \times 10^4$ counts per well of 96-well plates and grown at 37° C. in a 5% $CO_2$ incubator for 1 day. The culture medium in each well was replaced with a fresh medium containing the compounds of interest, followed by overnight incubation in the incubator. Following the addition of 100 µl of a 100 µg/ml Neutral red solution into each well, the cells were stained for 3 hours in the incubator and fixed in 1% formaldehyde with 1% $CaCl_2$. The cells were destained in 1% glacial acetic acid plus 50% ethanol, followed by measurement for absorbance at 540 nm. Cytotoxicity was expressed as percentages of optical density relative to that of the control, treated with none of the compounds. All tests were conducted in triplicate for each group, and the results are given in Table 12, below.

TABLE 12

| Ex. 30 | Ex. 39 | Ex. 50 | Ex. 52 | Ex. 68 | Ex. 69 | Ex. 240 | Ex. 245 | Ex. 314 |
|--------|--------|--------|--------|--------|--------|---------|---------|---------|
| 7.2%   | 3.0%   | 5.2%   | 5.6%   | 2.4%   | 1.6%   | 5.2%    | 9.9%    | 1.6%    |

Test Example 4

Assay for Acute Toxicity

From acute cytotoxicity tests using suspensions of compounds 50, 60, 234, 245, and 310 according to the present invention in an aqueous 25% beta-hydroxypropyl methylcellulose base or polyethylene glycol 400, mice were observed to suffer from no toxic syndromes, including severe changes to living states and organs, to a dose of 1000 mg/kg for two weeks upon oral administration.

INDUSTRIAL APPLICABILITY

As described hereinbefore, the triazole derivatives represented by Chemical Formula 1 or pharmaceutically acceptable salts thereof are very useful as active ingredients for antifungal agents because they have excellent inhibitory activity against a broad spectrum of fungi and show far higher therapeutic effects on fungal infection and far lower hepatotoxicity than do conventional drugs in addition to being safe to the body, high doses being allowable for oral administration.

The invention claimed is:

1. A compound represented by the following chemical formula 1, an isomer thereof, or a pharmaceutically acceptable salt thereof:

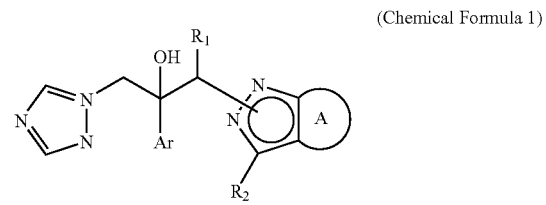

(Chemical Formula 1)

wherein,

Ar is a phenyl substituted with at least one halogen or $C_1$-$C_4$ haloalkyl;

$R_1$ is hydrogen, one or two fluorine atoms, or $C_1$-$C_3$ lower alkyl;

$R_2$ is hydrogen, halogen, $C_1$-$C_3$ lower alkyl, $C_1$-$C_4$ haloalkyl, $C_1$-$C_4$ alkoxy, nitro, cyano, amino, hydroxy, —$NR_3R_4$, —$CONR_3R_4$, —$CH_2$—OCO—$R_3$, —CO—$R_3$—COOR$_3$, —C(=$NR_4$)NHR$_3$, or —C(=$NR_4$)OR$_3$;

A is a benzene ring or a 5- or 6-membered heterocyclic ring containing one or more heteroatoms selected from among N, O and S, and may be non-fused or fused with a benzene ring or a 5- or 6-membered heterocyclic ring containing one or more heteroatoms selected from among N, O and S, with no or at least one substituent X therein, X being hydrogen, $C_1$-$C_4$ alkyl, $C_3$-$C_6$ cycloalkyl, $C_1$-$C_4$ haloalkyl, $C_1$-$C_4$ alkoxy, $C_1$-$C_4$ haloalkoxy, halogen, nitro, cyano, hydroxy, benzyloxy, hydroxymethyl, —$NR_3R_4$, —$NR_3COR_4$, —$NR_3SO_2R_4$, —$CONR_3R_4$, —$CH_2$—OCO—$R_3$, —CO—$R_3$, —COOR$_3$, —$SO_zR_3$, —C(=$NR_4$)NHR$_3$, —C(=$NR_4$)OR$_3$, or a 5-, 6-, or 7-membered heterocyclic ring containing at least one heteroatom selected from among N, O and S;

$R_3$ is hydrogen, $C_1$-$C_4$ alkyl, $C_3$-$C_6$ cycloalkyl, a 5- or 6-membered heterocyclic ring containing at least one heteroatom selected from among N, O and S, —$CH_2COR_4$, —$CH_2CONR_4$ or aryl $C_1$-$C_4$ alkyl, the aryl moiety being a phenyl group non-substituted or substituted with at least one halogen, $C_1$-$C_4$ alkyl, $C_1$-$C_4$ haloalkyl, $C_1$-$C_4$ alkoxy, $C_1$-$C_4$ haloalkoxy, nitro, cyano, hydroxy, benzyloxy, phenyl or hydroxymethyl, or being a bicyclic ring in which a 5- or 6-membered heterocyclic ring containing at least one heteroatom selected from among N, O and S is fused to a benzene ring;

$R_4$ is hydrogen, $C_1$-$C_4$ alkyl, $C_3$-$C_6$ cycloalkyl, —COR$_3$, —COCF$_3$, —CHR$_7$NHR$_3$R$_4$, —CHR$_7$COR$_3$, or the same aryl $C_1$-$C_4$ alkyl as defined in $R_3$;

$R_5$ is hydrogen, —CONH$_2$, —COCH$_3$, —CN, —SO$_2$NHR$_3$, —SO$_2$R$_3$, —OR$_3$, —OCOR$_3$ or —($C_1$-$C_4$ alkyl)-NH$_2$;

$R_6$ is $C_1$-$C_4$ alkyl;

$R_7$ is an α- or β-amino acid residue, whether D or L type, selected from 20 amino acid residues; and z is 0, 1 or 2;

wherein the nitrogen atom of position 1 or 2 in the pyrazole ring is bonded to the propanol substituted with the triazole ring, Ar and $R_1$.

2. The compound, the isomer, or the pharmaceutically acceptable salt as defined in claim 1, wherein, Ar is phenyl substituted with two or more halogens or $C_1$-$C_4$ haloalkyl;

$R_1$ is hydrogen, one or two fluorine atoms, or a $C_1$-$C_3$ lower alkyl;

$R_2$ is hydrogen, halogen, $C_1$-$C_3$ lower alkyl, $C_1$-$C_4$ haloalkyl, $C_1$-$C_4$ alkoxy, nitro, cyano, amino, hydroxy, $NR_3R_4$, —$CONR_3R_4$, —$CH_2$—OCO—$R_3$—CO—$R_3$, —$COOR_3$, —C (=$NR_4$)$NHR_3$, —C(=$NR_4$)$OR_3$;

A is a benzene ring or a 5- or 6-membered heterocyclic ring containing one or more heteroatoms selected from among N, O and S, and may be non-fused or fused with a benzene ring or a 5- or 6-membered heterocyclic ring containing one or more heteroatoms selected from among N, O and S, with no or at least one substituent X therein, X being hydrogen, $C_1$-$C_4$ alkyl, $C_3$-$C_6$ cycloalkyl, $C_1$-$C_4$ haloalkyl, $C_1$-$C_4$ alkoxy, $C_1$-$C_4$ haloalkoxy, halogen, nitro, cyano, hydroxy, benzyloxy, —$NR_3R_4$, —$NR_3COR_4$, —$NR_3SO_2R_4$, —$CONR_3R_4$, —$CH_2$—OCO—$R_3$, —CO—$R_3$, —$OCOR_3$, —$SO_2R_3$, —C(=$NR_4$)$NHR_3$, —C(=$NR_4$)$OR_3$, or a 5-, 6-, or 7-membered heterocyclic ring containing at least one heteroatom selected from among N, O and S;

$R_3$ is hydrogen, $C_1$-$C_4$ alkyl, $C_3$-$C_6$ cycloalkyl, a 5- or 6-membered heterocyclic ring containing at least one heteroatom selected from among N, O and S, —$CH_2COR_4$, $CH_2CONR_4$ or aryl $C_1$-$C_4$ alkyl, the aryl moiety being a phenyl group non-substituted or substituted with at least one halogen, $C_1$-$C_4$ alkyl, $C_1$-$C_4$ haloalkyl, $C_1$-$C_4$ alkoxy, $C_1$-$C_4$ haloalkoxy, nitro, cyano, hydroxy, benzyloxy, phenyl or hydroxymethyl, or being a bicyclic ring in which a 5- or 6-membered heterocyclic ring containing at least one heteroatom selected from among N, O and S is fused to a benzene ring;

$R_4$ is hydrogen, $C_1$-$C_4$ alkyl, $C_3$-$C_6$ cycloalkyl, —$COR_3$, —$COCF_3$, —$CHR_7NHR_3R_4$, —$CHR_7COR_3$ or the same aryl $C_1$-$C_4$ alkyl as defined in $R_3$;

$R_5$ is hydrogen, —$CONH_2$, —$COCH_3$, —CN, —$SO_2NHR_3$, —$SO_2R_3$, —$OR_3$, —$OCOR_3$ or —($C_1$-$C_4$ alkyl)-$NH_2$;

$R_6$ is $C_1$-$C_4$ alkyl;

$R_7$ is an α- or β-amino acid residue, whether D or L type, selected from 20 amino acid residues; and z is 0, 1 or 2;

wherein the nitrogen atom of position 1 or 2 in the pyrazole ring is bonded to the propanol substituted with the triazole ring, Ar and $R_1$.

3. The compound as defined in claim 1, wherein the compound is selected from the group consisting of:

1) 2-(2,4-difluorophenyl)-1-(1H-indazol-1-yl)-3-(1H-1,2,4-triazol-1-yl)propan-2-ol, 2) 2-(2,4-difluorophenyl)-1-(2H-indazol-2-yl)-3-(1H-1,2,4-triazol-1-yl)propan-2-ol, 3) 2-(2,4-difluorophenyl)-1-(5-nitro-1H-indazol-1-yl)-3-(1H-1,2,4-triazol-1-yl)propan-2-ol, 4) 2-(2,4-difluorophenyl)-1-(5-nitro-2H-indazol-2-yl)-3-(1H-1,2,4-triazol-1-yl)propan-2-ol, 5) 2-(2,4-difluorophenyl)-1-(6-nitro-2H-indazol-2-yl)-3-(1H-1,2,4-triazol-1-yl)propan-2-ol, 6) (5-amino-1H-indazol-1-yl)-2-(2,4-difluorophenyl)-3-(1H-1,2,4-triazol-1-yl)propan-2-ol, 7) (5-amino-2H-indazol-2-yl)-2-(2,4-difluorophenyl)-3-(1H-1,2,4-triazol-1-yl)propan-2-ol, 8) (6-amino-2H-indazol-2-yl)-2-(2,4-difluorophenyl)-3-(1H-1,2,4-triazol-1-yl)propan-2-ol, 9) 1-(5-(Benzylamino)-1H-indazol-1-yl)-2-(2,4-difluorophenyl)-3-(1H-1,2,4-triazol-1-yl)propan-2-ol, 10) 1-(5-(2-chlorobenzylamino)-1H-indazol-1-yl)-2-(2,4-difluorophenyl)-3-(1H-1,2,4-triazol-1-yl)propan-2-ol, 11) 1-(5-(2-chlorobenzylamino)-2H-indazol-2-yl)-2-(2,4-difluorophenyl)-3-(1H-1,2,4-triazol-1-yl)propan-2-ol, 12) 2-(2,4-difluorophenyl)-1-(1H-1,2,4-triazol-1-yl)-3-(5-(2-(trifluoromethyl)benzylamino)-1H-indazol-1-yl)propan-2-ol, 13) 2-(2,4-difluorophenyl)-1-(1H-1,2,4-triazol-1-yl)-3-(5-(2-(trifluoromethyl)benzylamino)-2H-indazol-2-yl)propan-2-ol, 14) 1-(5-(biphenyl-2-ylmethylamino)-1H-indazol-1-yl)-2-(2,4-difluorophenyl)-3-(1H-1,2,4-triazol-1-yl)propan-2-ol, 15) 2-(2,4-difluorophenyl)-1-(5-(4-fluorobenzylamino)-2H-indazol-2-yl)-3-(1H-1,2,4-triazol-1-yl)propan-2-ol, 16) 1-(5-(4-chlorobenzylamino)-1H-indazol-1-yl)-2-(2,4-difluorophenyl)-3-(1H-1,2,4-triazol-1-yl)propan-2-ol, 17) 1-(5-(4-chlorobenzylamino)-2H-indazol-2-yl)-2-(2,4-difluorophenyl)-3-(1H-1,2,4-triazol-1-yl)propan-2-ol, 18) 1-(5-(4-bromobenzylamino)-2H-indazol-2-yl)-2-(2,4-difluorophenyl)-3-(1H-1,2,4-triazol-1-yl)propan-2-ol, 19) 2-(2,4-difluorophenyl)-1-(1H-1,2,4-triazol-1-yl)-3-(5-(4-(trifluoromethyl)benzylamino)-2H-indazol-2-yl)propan-2-ol, 20) 4-((1-(2-(2,4-difluorophenyl)-2-hydroxy-3-(1H-1,2,4-triazol-1-yl)propyl)-2H-indazol-5-ylamino)methyl)benzonitrile, 21) 2-(2,4-difluorophenyl)-1-(5-(4-nitrobenzylamino)-2H-indazol-2-yl)-3-(1H-1,2,4-triazol-1-yl)propan-2-ol, 22) 2-(2,4-difluorophenyl)-1-(1H-1,2,4-triazol-1-yl)-3-(5-(4-(trifluoromethoxy)benzylamino)-2H-indazol-2-yl)propan-2-ol, 23) 1-(5-(2,4-difluorobenzylamino)-1H-indazol-1-yl)-2-(2,4-difluorophenyl)-3-(1H-1,2,4-triazol-1-yl)propan-2-ol, 24) 1-(5-(2,4-difluorobenzylamino)-2H-indazol-2-yl)-2-(2,4-difluorophenyl)-3-(1H-1,2,4-triazol-1-yl)propan-2-ol, 25) 1-(5-(2,4-dichlorobenzylamino)-1H-indazol-1-yl)-2-(2,4-difluorophenyl)-3-(1H-1,2,4-triazol-1-yl)propan-2-ol, 26) 1-(5-(2,4-bis(trifluoromethyl)benzylamino)-2H-indazol-2-yl)-2-(2,4-difluorophenyl)-3-(1H-1,2,4-triazol-1-yl)propan-2-ol, 27) 1-(5-(2,6-difluorobenzylamino)-2H-indazol-2-yl)-2-(2,4-difluorophenyl)-3-(1H-1,2,4-triazol-1-yl)propan-2-ol, 28) 1-(5-(2,6-dichlorobenzylamino)-2H-indazol-2-yl)-2-(2,4-difluorophenyl)-3-(1H-1,2,4-triazol-1-yl)propan-2-ol, 29) 1-(5-(2-chloro-6-fluorobenzylamino)-2H-indazol-2-yl)-2-(2,4-difluorophenyl)-3-(1H-1,2,4-triazol-1-yl)propan-2-ol, 30) 1-(6-(2-chlorobenzylamino)-2H-indazol-2-yl)-2-(2,4-difluorophenyl)-3-(1H-1,2,4-triazol-1-yl)propan-2-ol, 31) 2-(2,4-difluorophenyl)-1-(6-(4-fluorobenzylamino)-2H-indazol-2-yl)-3-(1H-1,2,4-triazol-1-yl)propan-2-ol, 32) 1-(6-(4-chlorobenzylamino)-2H-indazol-2-yl)-2-(2,4-difluorophenyl)-3-(1H-1,2,4-triazol-1-yl)propan-2-ol,
33) 1-(6-(4-bromobenzylamino)-2H-indazol-2-yl)-2-(2,4-difluorophenyl)-3-(1H-1,2,4-triazol-1-yl)propan-2-ol,
34) 2-(2,4-difluorophenyl)-1-(1H-1,2,4-triazol-1-yl)-3-(6-(4-(trifluoromethyl)benzylamino)-2H-indazol-2-yl)propan-2-ol,
35) 4-((2-(2-(2,4-difluorophenyl)-2-hydroxy-3-(1H-1,2,4-triazol-1-yl)propyl)-2H-indazol-6-ylamino)methyl)benzonitrile,
36) 1-(6-(2,4-dichlorobenzylamino)-2H-indazol-2-yl)-2-(2,4-difluorophenyl)-3-(1H-1,2,4-triazol-1-yl)propan-2-ol,
37) 1-(6-(2,6-difluorobenzylamino)-2H-indazol-2-yl)-2-(2,4-difluorophenyl)-3-(1H-1,2,4-triazol-1-yl)propan-2-ol,
38) 1-(6-(2,6-dichlorobenzylamino)-2H-indazol-2-yl)-2-(2,4-difluorophenyl)-3-(1H-1,2,4-triazol-1-yl)propan-2-ol,
39) 1-(6-(2-chloro-6-fluorobenzylamino)-2H-indazol-2-yl)-2-(2,4-difluorophenyl)-3-(1H-1,2,4-triazol-1-yl)propan-2-ol,
40) 2-(2,4-difluorophenyl)-2-hydroxy-3-(1H-1,2,4-triazol-1-yl)propyl)-3-methyl-1H-indazol-4-ol,
41) 2-(2,4-difluorophenyl)-1-(4-(4-fluorobenzyloxy)-3-methyl-1H-indazol-1-yl)-3-(1H-1,2,4-triazol-1-yl)propan-2-ol,
42) 1-(4-(4-chlorobenzyloxy)-3-methyl-1H-indazol-1-yl)-2-(2,4-difluorophenyl)-3-(1H-1,2,4-triazol-1-yl)propan-2-ol,
43) 4-((1-(2-(2,4-difluorophenyl)-2-hydroxy-3-(1H-1,2,4-triazol-1-yl)propyl)-3-methyl-1H-indazol-4-yloxy)methyl)benzonitrile,
44) (E)-3-(4-bromophenyl)-N-1-(2-(2,4-difluorophenyl)-2-hydroxy-3-(1H-1,2,4-triazol-5-yl)acetamide,
45) (2S)-2-Amino-N-1-(2-(2,4-difluorophenyl)-2-hydroxy-3-(1H-1,2,4-triazol-1-yl)propyl)-1H-indazol-5-yl)-3-phenylpropaneamide,
46) 2-(1-(2-(2,4-difluorophenyl)-2-hydroxy-3-(1H-1,2,4-triazol-1-yl)propyl)-1H-indazol-5-yl)amino)-N-(2,6-dimethylphenyl)acetamide,
47) 2-(3-(1-(2-(2,4-difluorophenyl)-2-hydroxy-3-(1H-1,2,4-triazol-1-yl)propyl)-1H-indazol-5-ylamino)-2-oxopropyl)-4,5,6,7-tetrahydrobenzo[b]thiophene-3-carbonitrile,
48) 2-((2-(2-(2,4-difluorophenyl)-2-hydroxy-3-(1H-1,2,4-triazol-1-yl)propyl)-1H-indazol-5-yl)amino)-1-(4-phenylpiperazin-1-yl)ethanone,
49) Methyl 2-((2-(2-(2,4-difluorophenyl)-2-hydroxy-3-(1H-1,2,4-triazol-1-yl)propyl)-1H-indazol-5-yl)amino)acetate,
50) (2R,3R)-2-(2,4-difluorophenyl)-3-(1H-indazol-1-yl)-1-(1H-1,2,4-triazol-1-yl)butan-2-ol,
51) (2R,3R)-2-(2,4-difluorophenyl)-3-(2H-indazol-2-yl)-1-(1H-1,2,4-triazol-1-yl)butan-2-ol,
52) (2R,3R)-3-(3-chloro-1H-indazol-1-yl)-2-(2,4-difluorophenyl)-1-(1H-1,2,4-triazol-1-yl)butan-2-ol,
53) (2R,3R)-2-(2,4-difluorophenyl)-3-(3-fluoro-7-(trifluoromethyl)-1H-indazol-1-yl)-1-(1H-1,2,4-triazol-1-yl)butan-2-ol,
54) (2R,3R)-2-(2,4-difluorophenyl)-3-(3-fluoro-7-(trifluoromethyl)-2H-indazol-2-yl)-1-(1H-1,2,4-triazol-1-yl)butan-2-ol,
55) (2R,3R)-2-(2,4-difluorophenyl)-3-(5-iodo-1H-indazol-1-yl)-1-(1H-1,2,4-triazol-1-yl)butan-2-ol,
56) (2R,3R)-2-(2,4-difluorophenyl)-3-(5-fluoro-1H-indazol-1-yl)-1-(1H-1,2,4-triazol-1-yl)butan-2-ol,
57) (2R,3R)-3-(5-chloro-2H-indazol-2-yl)-2-(2,4-difluorophenyl)-1-(1H-1,2,4-triazol-1-yl)butan-2-ol,
58) (2R,3R)-3-(5-bromo-1H-indazol-1-yl)-2-(2,4-difluorophenyl)-1-(1H-1,2,4-triazol-1-yl)butan-2-ol,
59) (2R,3R)-3-(5-bromo-2H-indazol-2-yl)-2-(2,4-difluorophenyl)-1-(1H-1,2,4-triazol-1-yl)butan-2-ol,
60) 1-((2R,3R)-3-(2,4-difluorophenyl)-3-hydroxy-4-(1H-1,2,4-triazol-1-yl)butan-2-yl)-1H-indazole-5-carbonitrile,
61) (2R,3R)-2-(2,4-difluorophenyl)-3-(3-iodo-5-nitro-1H-indazol-1-yl)-1-(1H-1,2,4-triazol-1-yl)butan-2-ol,
62) (2R,3R)-2-(2,4-difluorophenyl)-3-(3-methyl-1H-indazol-1-yl)-1-(1H-1,2,4-triazol-1-yl)butan-2-ol,
63) (2R,3R)-2-(2,4-difluorophenyl)-3-(3-methyl-2H-indazol-2-yl)-1-(1H-1,2,4-triazol-1-yl)butan-2-ol,
64) (2R,3R)-2-(2,4-difluorophenyl)-3-(4-fluoro-3-methyl-1H-indazol-1-yl)-1-(1H-1,2,4-triazol-1-yl)butan-2-ol,
65) (2R,3R)-2-(2,4-difluorophenyl)-3-(4-fluoro-3-methyl-2H-indazol-2-yl)-1-(1H-1,2,4-triazol-1-yl)butan-2-ol,
66) (2R,3R)-3-(4-chloro-3-methyl-1H-indazol-1-yl)-2-(2,4-difluorophenyl)-1-(1H-1,2,4-triazol-1-yl)butan-2-ol,
67) (2R,3R)-3-(4-chloro-3-methyl-2H-indazol-2-yl)-2-(2,4-difluorophenyl)-1-(1H-1,2,4-triazol-1-yl)butan-2-ol,
68) (2R,3R)-2-(2,4-difluorophenyl)-3-(3-methyl-4-(trifluoromethyl)-1H-indazol-1-yl)-1-(1H-1,2,4-triazol-1-yl)butan-2-ol,
69) (2R,3R)-2-(2,4-difluorophenyl)-3-(3-methyl-4-(trifluoromethyl)-2H-indazol-2-yl)-1-(1H-1,2,4-triazol-1-yl)butan-2-ol,
70) (2R,3R)-2-(2,4-difluorophenyl)-3-(5-fluoro-3-methyl-1H-indazol-1-yl)-1-(1H-1,2,4-triazol-1-yl)butan-2-ol,
71) (2R,3R)-2-(2,4-difluorophenyl)-3-(5-fluoro-3-methyl-2H-indazol-2-yl)-1-(1H-1,2,4-triazol-1-yl)butan-2-ol,
72) (2R,3R)-2-(2,4-difluorophenyl)-3-(3-methyl-5-(trifluoromethyl)-1H-indazol-1-yl)-1-(1H-1,2,4-triazol-1-yl)butan-2-ol,
73) (2R,3R)-2-(2,4-difluorophenyl)-3-(3-methyl-5-(trifluoromethyl)-2H-indazol-2-yl)-1-(1H-1,2,4-triazol-1-yl)butan-2-ol,
74) (2R,3R)-2-(2,4-difluorophenyl)-3-(6-fluoro-3-methyl-1H-indazol-1-yl)-1-(1H-1,2,4-triazol-1-yl)butan-2-ol,
75) (2R,3R)-2-(2,4-difluorophenyl)-3-(6-fluoro-3-methyl-2H-indazol-2-yl)-1-(1H-1,2,4-triazol-1-yl)butan-2-ol,
76) (2R,3R)-2-(2,4-difluorophenyl)-3-(3-methyl-6-(trifluoromethyl)-1H-indazol-1-yl)-1-(1H-1,2,4-triazol-1-yl)butan-2-ol,
77) (2R,3R)-2-(2,4-difluorophenyl)-3-(3-methyl-6-(trifluoromethyl)-2H-indazol-2-yl)-1-(1H-1,2,4-triazol-1-yl)butan-2-ol,
78) (2R,3R)-3-(4,6-difluoro-3-methyl-1H-indazol-1-yl)-2-(2,4-difluorophenyl)-1-(1H-1,2,4-triazol-1-yl)butan-2-ol,
79) (2R,3R)-3-(4,6-difluoro-3-methyl-2H-indazol-2-yl)-2-(2,4-difluorophenyl)-1-(1H-1,2,4-triazol-1-yl)butan-2-ol,
80) (2R,3R)-3-(4-chloro-6-fluoro-3-methyl-1H-indazol-1-yl)-2-(2,4-difluorophenyl)-1-(1H-1,2,4-triazol-1-yl)butan-2-ol,
81) (2R,3R)-3-(4-chloro-6-fluoro-3-methyl-2H-indazol-2-yl)-2-(2,4-difluorophenyl)-1-(1H-1,2,4-triazol-1-yl)butan-2-ol, 82) (2R,3R)-3-(5,6-difluoro-3-methyl-1H-indazol-1-yl)-2-(2,4-difluorophenyl)-1-(1H-1,2,4-triazol-1-yl)butan-2-ol,
83) (2R,3R)-3-(5,6-difluoro-3-methyl-2H-indazol-2-yl)-2-(2,4-difluorophenyl)-1-(1H-1,2,4-triazol-1-yl)butan-2-ol,
84) (2R,3R)-3-(6-chloro-5-fluoro-3-methyl-1H-indazol-1-yl)-2-(2,4-difluorophenyl)-1-(1H-1,2,4-triazol-1-yl)butan-2-ol,
85) (2R,3R)-3-(6-chloro-5-fluoro-3-methyl-2H-indazol-2-yl)-2-(2,4-difluorophenyl)-1-(1H-1,2,4-triazol-1-yl)butan-2-ol,
86) (2R,3R)-3-(4-chloro-3,7-dimethyl-1H-indazol-1-yl)-2-(2,4-difluorophenyl)-1-(1H-1,2,4-triazol-1-yl)butan-2-ol,
87) (2R,3R)-3-(4-chloro-3,7-dimethyl-2H-indazol-2-yl)-2-(2,4-difluorophenyl)-1-(1H-1,2,4-triazol-1-yl)butan-2-ol,
88) (2R,3R)-3-(6,7-difluoro-3-methyl-1H-indazol-1-yl)-2-(2,4-difluorophenyl)-1-(1H-1,2,4-triazol-1-yl)butan-2-ol,
89) (2R,3R)-3-(6,7-difluoro-3-methyl-2H-indazol-2-yl)-2-(2,4-difluorophenyl)-1-(1H-1,2,4-triazol-1-yl)butan-2-ol,
90) (2R,3R)-2-(2,4-difluorophenyl)-1-(1H-1,2,4-triazol-1-yl)-3-(5,6,7-trifluoro-3-methyl-1H-indazol-1-yl)butan-2-ol,
91) (2R,3R)-2-(2,4-difluorophenyl)-1-(1H-1,2,4-triazol-1-yl)-3-(5,6,7-trifluoro-3-methyl-2H-indazol-2-yl)butan-2-ol,
92) (2R,3R)-2-(2,4-difluorophenyl)-3-(4,5,6,7-tetrafluoro-3-methyl-1H-indazol-1-yl)-1-(1H-1,2,4-triazol-1-yl)butan-2-ol,
93) (2R,3R)-2-(2,4-difluorophenyl)-3-(4,5,6,7-tetrafluoro-3-methyl-2H-indazol-2-yl)-1-(1H-1,2,4-triazol-1-yl)butan-2-ol,
94) (2R,3R)-2-(2,4-difluorophenyl)-3-(3-ethyl-1H-indazol-1-yl)-1-(1H-1,2,4-triazol-1-yl)butan-2-ol,
95) (2R,3R)-3-(5-bromo-7-chloro-3-ethyl-2H-indazol-2-yl)-2-(2,4-difluorophenyl)-1-(1H-1,2,4-triazol-1-yl)butan-2-ol,
96) (2R,3R)-2-(2,4-difluorophenyl)-3-(3-ethyl-4-fluoro-1H-indazol-1-yl)-1-(1H-1,2,4-triazol-1-yl)butan-2-ol,
97) (2R,3R)-2-(2,4-difluorophenyl)-3-(3-ethyl-4-fluoro-2H-indazol-2-yl)-1-(1H-1,2,4-triazol-1-yl)butan-2-ol,
98) (2R,3R)-2-(2,4-difluorophenyl)-3-(3-ethyl-5-fluoro-1H-indazol-1-yl)-1-(1H-1,2,4-triazol-1-yl)butan-2-ol,
99) (2R,3R)-2-(2,4-difluorophenyl)-3-(3-ethyl-5-fluoro-2H-indazol-2-yl)-1-(1H-1,2,4-triazol-1-yl)butan-2-ol,
100) (2R,3R)-2-(2,4-difluorophenyl)-3-(3-ethyl-6-fluoro-1H-indazol-1-yl)-1-(1H-1,2,4-triazol-1-yl)butan-2-ol,
101) (2R,3R)-2-(2,4-difluorophenyl)-3-(3-ethyl-6-fluoro-2H-indazol-2-yl)-1-(1H-1,2,4-triazol-1-yl)butan-2-ol,
102) (2R,3R)-2-(2,4-difluorophenyl)-3-(3-ethyl-6-(trifluoromethyl)-1H-indazol-1-yl)-1-(1H-1,2,4-triazol-1-yl)butan-2-ol,
103) (2R,3R)-2-(2,4-difluorophenyl)-3-(3-ethyl-6-(trifluoromethyl)-2H-indazol-2-yl)-1-(1H-1,2,4-triazol-1-yl)butan-2-ol,
104) (2R,3R)-2-(2,4-difluorophenyl)-3-(3-methyl-5-nitro-1H-indazol-1-yl)-1-(1H-1,2,4-triazol-1-yl)butan-2-ol,
105) (2R,3R)-2-(2,4-difluorophenyl)-3-(3-methyl-5-nitro-2H-indazol-2-yl)-1-(1H-1,2,4-triazol-1-yl)butan-2-ol,
106) (2R,3R)-3-(5-amino-3-methyl-1H-indazol-1-yl)-2-(2,4-difluorophenyl)-1-(1H-1,2,4-triazol-1-yl)butan-2-ol,
107) (2R,3R)-3-(5-amino-3-methyl-2H-indazol-2-yl)-2-(2,4-difluorophenyl)-1-(1H-1,2,4-triazol-1-yl)butan-2-ol,
108) (2R,3R)-3-(5-chloro-3-methyl-1H-indazol-1-yl)-2-(2,4-difluorophenyl)-1-(1H-1,2,4-triazol-1-yl)butan-2-ol,
109) (2R,3R)-3-(5-chloro-3-methyl-2H-indazol-2-yl)-2-(2,4-difluorophenyl)-1-(1H-1,2,4-triazol-1-yl)butan-2-ol,
110) (2R,3R)-2-(2,4-difluorophenyl)-3-(3-methyl-7-nitro-1H-indazol-1-yl)-1-(1H-1,2,4-triazol-1-yl)butan-2-ol,
111) (2R,3R)-2-(2,4-difluorophenyl)-3-(3-methyl-7-nitro-2H-indazol-2-yl)-1-(1H-1,2,4-triazol-1-yl)butan-2-ol,
112) (2R,3R)-2-(2,4-difluorophenyl)-3-(7-fluoro-3-methyl-1H-indazol-1-yl)-1-(1H-1,2,4-triazol-1-yl)butan-2-ol,
113) (2R,3R)-2-(2,4-difluorophenyl)-3-(7-fluoro-3-methyl-2H-indazol-2-yl)-1-(1H-1,2,4-triazol-1-yl)butan-2-ol,
114) (2R,3R)-3-(7-chloro-3-methyl-1H-indazol-1-yl)-2-(2,4-difluorophenyl)-1-(1H-1,2,4-triazol-1-yl)butan-2-ol,
115) (2R,3R)-3-(7-chloro-3-methyl-2H-indazol-2-yl)-2-(2,4-difluorophenyl)-1-(1H-1,2,4-triazol-1-yl)butan-2-ol,
116) (2R,3R)-3-(5-bromo-7-fluoro-3-methyl-1H-indazol-1-yl)-2-(2,4-difluorophenyl)-1-(1H-1,2,4-triazol-1-yl)butan-2-ol,
117) (2R,3R)-3-(5-bromo-7-fluoro-3-methyl-2H-indazol-2-yl)-2-(2,4-difluorophenyl)-1-(1H-1,2,4-triazol-1-yl)butan-2-ol,
118) (2R,3R)-3-(5-bromo-7-chloro-3-methyl-1H-indazol-1-yl)-2-(2,4-difluorophenyl)-1-(1H-1,2,4-triazol-1-yl)butan-2-ol,
119) (2R,3R)-3-(5-bromo-7-chloro-3-methyl-2H-indazol-2-yl)-2-(2,4-difluorophenyl)-1-(1H-1,2,4-triazol-1-yl)butan-2-ol,
120) (2R,3R)-2-(2,4-difluorophenyl)-3-(7-fluoro-3,5-dimethyl-1H-indazol-1-yl)-1-(1H-1,2,4-triazol-1-yl)butan-2-ol,
121) (2R,3R)-2-(2,4-difluorophenyl)-3-(7-fluoro-3,5-dimethyl-2H-indazol-2-yl)-1-(1H-1,2,4-triazol-1-yl)butan-2-ol,
122) (2R,3R)-3-(7-chloro-3,5-dimethyl-1H-indazol-1-yl)-2-(2,4-difluorophenyl)-1-(1H-1,2,4-triazol-1-yl)butan-2-ol,
123) (2R,3R)-3-(7-chloro-3,5-dimethyl-2H-indazol-2-yl)-2-(2,4-difluorophenyl)-1-(1H-1,2,4-triazol-1-yl)butan-2-ol,
124) (2R,3R)-3-(6-chloro-3-methyl-1H-indazol-1-yl)-2-(2,4-difluorophenyl)-1-(1H-1,2,4-triazol-1-yl)butan-2-ol,
125) (2R,3R)-3-(6-chloro-3-methyl-2H-indazol-2-yl)-2-(2,4-difluorophenyl)-1-(1H-1,2,4-triazol-1-yl)butan-2-ol,
126) (2R,3R)-2-(2,4-difluorophenyl)-3-(6-fluoro-3,7-dimethyl-1H-indazol-1-yl)-1-(1H-1,2,4-triazol-1-yl)butan-2-ol,
127) (2R,3R)-2-(2,4-difluorophenyl)-3-(6-fluoro-3,7-dimethyl-2H-indazol-2-yl)-1-(1H-1,2,4-triazol-1-yl)butan-2-ol, 128) (2R,3R)-3-(6-chloro-3,7-dimethyl-1H-indazol-1-yl)-2-(2,4-difluorophenyl)-1-(1H-1,2,4-triazol-1-yl)butan-2-ol,
129) (2R,3R)-3-(6-chloro-3,7-dimethyl-2H-indazol-2-yl)-2-(2,4-difluorophenyl)-1-(1H-1,2,4-triazol-1-yl)butan-2-ol,
130) (2R,3R)-3-(5-chloro-6-fluoro-3-methyl-1H-indazol-1-yl)-2-(2,4-difluorophenyl)-1-(1H-1,2,4-triazol-1-yl)butan-2-ol,
131) (2R,3R)-3-(5-chloro-6-fluoro-3-methyl-2H-indazol-2-yl)-2-(2,4-difluorophenyl)-1-(1H-1,2,4-triazol-1-yl)butan-2-ol,
132) (2R,3R)-2-(2,4-difluorophenyl)-3-(6-fluoro-3,5-dimethyl-1H-indazol-1-yl)-1-(1H-1,2,4-triazol-1-yl)butan-2-ol,
133) (2R,3R)-2-(2,4-difluorophenyl)-3-(6-fluoro-3,5-dimethyl-2H-indazol-2-yl)-1-(1H-1,2,4-triazol-1-yl)butan-2-ol,
134) (2R,3R)-3-(6-chloro-3,5-dimethyl-1H-indazol-1-yl)-2-(2,4-difluorophenyl)-1-(1H-1,2,4-triazol-1-yl)butan-2-ol,
135) (2R,3R)-3-(6-chloro-3,5-dimethyl-2H-indazol-2-yl)-2-(2,4-difluorophenyl)-1-(1H-1,2,4-triazol-1-yl)butan-2-ol,
136) (2R,3R)-2-(2,4-difluorophenyl)-3-(7-fluoro-3-methyl-5-nitro-1H-indazol-1-yl)-1-(1H-1,2,4-triazol-1-yl)butan-2-ol,
137) (2R,3R)-2-(2,4-difluorophenyl)-3-(7-fluoro-3-methyl-5-nitro-2H-indazol-2-yl)-1-(1H-1,2,4-triazol-1-yl)butan-2-ol,
138) (2R,3R)-3-(5,7-difluoro-3-methyl-1H-indazol-1-yl)-2-(2,4-difluorophenyl)-1-(1H-1,2,4-triazol-1-yl)butan-2-ol,
139) (2R,3R)-3-(5,7-difluoro-3-methyl-2H-indazol-2-yl)-2-(2,4-difluorophenyl)-1-(1H-1,2,4-triazol-1-yl)butan-2-ol,
140) (2R,3R)-3-(5-chloro-7-fluoro-3-methyl-1H-indazol-1-yl)-2-(2,4-difluorophenyl)-1-(1H-1,2,4-triazol-1-yl)butan-2-ol,
141) (2R,3R)-3-(5-chloro-7-fluoro-3-methyl-2H-indazol-2-yl)-2-(2,4-difluorophenyl)-1-(1H-1,2,4-triazol-1-yl)butan-2-ol,
142) (2R,3R)-3-(7-chloro-5-fluoro-3-methyl-1H-indazol-1-yl)-2-(2,4-difluorophenyl)-1-(1H-1,2,4-triazol-1-yl)butan-2-ol,
143) (2R,3R)-3-(7-chloro-5-fluoro-3-methyl-2H-indazol-2-yl)-2-(2,4-difluorophenyl)-1-(1H-1,2,4-triazol-1-yl)butan-2-ol,
144) (2R,3R)-3-(5,7-dichloro-3-methyl-1H-indazol-1-yl)-2-(2,4-difluorophenyl)-1-(1H-1,2,4-triazol-1-yl)butan-2-ol,
145) (2R,3R)-3-(5,7-dichloro-3-methyl-2H-indazol-2-yl)-2-(2,4-difluorophenyl)-1-(1H-1,2,4-triazol-1-yl)butan-2-ol,
146) (2R,3R)-2-(2,4-difluorophenyl)-3-(5-fluoro-3,7-dimethyl-1H-indazol-1-yl)-1-(1H-1,2,4-triazol-1-yl)butan-2-ol,
147) (2R,3R)-2-(2,4-difluorophenyl)-3-(5-fluoro-3,7-dimethyl-2H-indazol-2-yl)-1-(1H-1,2,4-triazol-1-yl)butan-2-ol,
148) (2R,3R)-3-(5-chloro-3,7-dimethyl-1H-indazol-1-yl)-2-(2,4-difluorophenyl)-1-(1H-1,2,4-triazol-1-yl)butan-2-ol,
149) (2R,3R)-3-(5-chloro-3,7-dimethyl-2H-indazol-2-yl)-2-(2,4-difluorophenyl)-1-(1H-1,2,4-triazol-1-yl)butan-2-ol,
150) (2R,3R)-2-(2,4-difluorophenyl)-3-(5-fluoro-3,6-dimethyl-1H-indazol-1-yl)-1-(1H-1,2,4-triazol-1-yl)butan-2-ol,
151) (2R,3R)-2-(2,4-difluorophenyl)-3-(5-fluoro-3,6-dimethyl-2H-indazol-2-yl)-1-(1H-1,2,4-triazol-1-yl)butan-2-ol,
152) (2R,3R)-3-(5-chloro-3,6-dimethyl-1H-indazol-1-yl)-2-(2,4-difluorophenyl)-1-(1H-1,2,4-triazol-1-yl)butan-2-ol,
153) (2R,3R)-3-(5-chloro-3,6-dimethyl-2H-indazol-2-yl)-2-(2,4-difluorophenyl)-1-(1H-1,2,4-triazol-1-yl)butan-2-ol,
154) (2R,3R)-3-(5-bromo-3-methyl-1H-indazol-1-yl)-2-(2,4-difluorophenyl)-1-(1H-1,2,4-triazol-1-yl)butan-2-ol,
155) (2R,3R)-3-(5-bromo-3-methyl-2H-indazol-2-yl)-2-(2,4-difluorophenyl)-1-(1H-1,2,4-triazol-1-yl)butan-2-ol,
156) (2R,3R)-3-(6-bromo-3-methyl-1H-indazol-1-yl)-2-(2,4-difluorophenyl)-1-(1H-1,2,4-triazol-1-yl)butan-2-ol,
157) (2R,3R)-3-(6-bromo-3-methyl-2H-indazol-2-yl)-2-(2,4-difluorophenyl)-1-(1H-1,2,4-triazol-1-yl)butan-2-ol,
158) 1-((2R,3R)-3-(2,4-difluorophenyl)-3-hydroxy-4-(1H-1,2,4-triazol-1-yl)butan-2-yl)-3-methyl-1H-indazole-5-carbonitrile,
159) 2-((2R,3R)-3-(2,4-difluorophenyl)-3-hydroxy-4-(1H-1,2,4-triazol-1-yl)butan-2-yl)-3-methyl-2H-indazole-5-carbonitrile,
160) (2R,3R)-3-(7-bromo-3-methyl-1H-indazol-1-yl)-2-(2,4-difluorophenyl)-1-(1H-1,2,4-triazol-1-yl)butan-2-ol,
161) (2R,3R)-3-(7-bromo-3-methyl-2H-indazol-2-yl)-2-(2,4-difluorophenyl)-1-(1H-1,2,4-triazol-1-yl)butan-2-ol,
162) (2R,3R)-2-(2,4-difluorophenyl)-3-(3-ethyl-7-nitro-1H-indazol-1-yl)-1-(1H-1,2,4-triazol-1-yl)butan-2-ol,
163) (2R,3R)-2-(2,4-difluorophenyl)-3-(3-ethyl-7-nitro-2H-indazol-2-yl)-1-(1H-1,2,4-triazol-1-yl)butan-2-ol,
164) (2R,3R)-2-(2,4-difluorophenyl)-3-(3-ethyl-7-fluoro-1H-indazol-1-yl)-1-(1H-1,2,4-triazol-1-yl)butan-2-ol,
165) (2R,3R)-2-(2,4-difluorophenyl)-3-(3-ethyl-7-fluoro-2H-indazol-2-yl)-1-(1H-1,2,4-triazol-1-yl)butan-2-ol,
166) (2R,3R)-3-(7-chloro-3-ethyl-1H-indazol-1-yl)-2-(2,4-difluorophenyl)-1-(1H-1,2,4-triazol-1-yl)butan-2-ol,
167) (2R,3R)-3-(7-chloro-3-ethyl-2H-indazol-2-yl)-2-(2,4-difluorophenyl)-1-(1H-1,2,4-triazol-1-yl)butan-2-ol,
168) (2R,3R)-3-(5-bromo-3-ethyl-7-fluoro-1H-indazol-1-yl)-2-(2,4-difluorophenyl)-1-(1H-1,2,4-triazol-1-yl)butan-2-ol,
169) (2R,3R)-3-(5-bromo-3-ethyl-7-fluoro-2H-indazol-2-yl)-2-(2,4-difluorophenyl)-1-(1H-1,2,4-triazol-1-yl)butan-2-ol,
170) (2R,3R)-3-(5-bromo-7-chloro-3-ethyl-1H-indazol-1-yl)-2-(2,4-difluorophenyl)-1-(1H-1,2,4-triazol-1-yl)butan-2-ol,
171) (2R,3R)-3-(5-bromo-7-chloro-3-ethyl-2H-indazol-2-yl)-2-(2,4-difluorophenyl)-1-(1H-1,2,4-triazol-1-yl)butan-2-ol,
172) (2R,3R)-2-(2,4-difluorophenyl)-3-(3-ethyl-7-fluoro-5-methyl-1H-indazol-1-yl)-1-(1H-1,2,4-triazol-1-yl)butan-2-ol,
173) (2R,3R)-2-(2,4-difluorophenyl)-3-(3-ethyl-7-fluoro-5-methyl-2H-indazol-2-yl)-1-(1H-1,2,4-triazol-1-yl)butan-2-ol, 174) (2R,3R)-3-(7-chloro-3-ethyl-5-methyl-1H-indazol-1-yl)-2-(2,4-difluorophenyl)-1-(1H-1,2,4-triazol-1-yl)butan-2-ol,
175) (2R,3R)-3-(7-chloro-3-ethyl-5-methyl-2H-indazol-2-yl)-2-(2,4-difluorophenyl)-1-(1H-1,2,4-triazol-1-yl)butan-2-ol,
176) (2R,3R)-2-(2,4-difluorophenyl)-3-(3-ethyl-6-nitro-1H-indazol-1-yl)-1-(1H-1,2,4-triazol-1-yl)butan-2-ol,
177) (2R,3R)-2-(2,4-difluorophenyl)-3-(3-ethyl-6-nitro-2H-indazol-2-yl)-1-(1H-1,2,4-triazol-1-yl)butan-2-ol,
178) (2R,3R)-2-(2,4-difluorophenyl)-3-(3-ethyl-6-nitro-1H-indazol-1-yl)-1-(1H-1,2,4-triazol-1-yl)butan-2-ol,
179) (2R,3R)-2-(2,4-difluorophenyl)-3-(3-ethyl-6-nitro-2H-indazol-2-yl)-1-(1H-1,2,4-triazol-1-yl)butan-2-ol,
180) (2R,3R)-2-(2,4-difluorophenyl)-3-(3-ethyl-6-fluoro-7-methyl-1H-indazol-1-yl)-1-(1H-1,2,4-triazol-1-yl)butan-2-ol,
181) (2R,3R)-2-(2,4-difluorophenyl)-3-(3-ethyl-6-fluoro-7-methyl-2H-indazol-2-yl)-1-(1H-1,2,4-triazol-1-yl)butan-2-ol,
182) (2R,3R)-3-(6-chloro-3-ethyl-7-methyl-1H-indazol-1-yl)-2-(2,4-difluorophenyl)-1-(1H-1,2,4-triazol-1-yl)butan-2-ol,
183) (2R,3R)-3-(6-chloro-3-ethyl-7-methyl-2H-indazol-2-yl)-2-(2,4-difluorophenyl)-1-(1H-1,2,4-triazol-1-yl)butan-2-ol,
184) (2R,3R)-3-(5-chloro-3-ethyl-6-fluoro-1H-indazol-1-yl)-2-(2,4-difluorophenyl)-1-(1H-1,2,4-triazol-1-yl)butan-2-ol,
185) (2R,3R)-3-(5-chloro-3-ethyl-6-fluoro-2H-indazol-2-yl)-2-(2,4-difluorophenyl)-1-(1H-1,2,4-triazol-1-yl)butan-2-ol,
186) (2R,3R)-3-(5,6-dichloro-3-ethyl-1H-indazol-1-yl)-2-(2,4-difluorophenyl)-1-(1H-1,2,4-triazol-1-yl)butan-2-ol,
187) (2R,3R)-3-(5,6-dichloro-3-ethyl-2H-indazol-2-yl)-2-(2,4-difluorophenyl)-1-(1H-1,2,4-triazol-1-yl)butan-2-ol,
188) (2R,3R)-2-(2,4-difluorophenyl)-3-(3-ethyl-6-fluoro-5-methyl-1H-indazol-1-yl)-1-(1H-1,2,4-triazol-1-yl)butan-2-ol,
189) (2R,3R)-2-(2,4-difluorophenyl)-3-(3-ethyl-6-fluoro-5-methyl-2H-indazol-2-yl)-1-(1H-1,2,4-triazol-1-yl)butan-2-ol,
190) (2R,3R)-3-(6-chloro-3-ethyl-5-methyl-1H-indazol-1-yl)-2-(2,4-difluorophenyl)-1-(1H-1,2,4-triazol-1-yl)butan-2-ol,
191) (2R,3R)-3-(6-chloro-3-ethyl-5-methyl-2H-indazol-2-yl)-2-(2,4-difluorophenyl)-1-(1H-1,2,4-triazol-1-yl)butan-2-ol,
192) (2R,3R)-2-(2,4-difluorophenyl)-3-(3-ethyl-5-nitro-1H-indazol-1-yl)-1-(1H-1,2,4-triazol-1-yl)butan-2-ol,
193) (2R,3R)-2-(2,4-difluorophenyl)-3-(3-ethyl-5-nitro-2H-indazol-2-yl)-1-(1H-1,2,4-triazol-1-yl)butan-2-ol,
194) (2R,3R)-3-(5-chloro-3-ethyl-1H-indazol-1-yl)-2-(2,4-difluorophenyl)-1-(1H-1,2,4-triazol-1-yl)butan-2-ol,
195) (2R,3R)-3-(5-chloro-3-ethyl-2H-indazol-2-yl)-2-(2,4-difluorophenyl)-1-(1H-1,2,4-triazol-1-yl)butan-2-ol,
196) (2R,3R)-2-(2,4-difluorophenyl)-3-(3-ethyl-5,7-difluoro-1H-indazol-1-yl)-1-(1H-1,2,4-triazol-1-yl)butan-2-ol,
197) (2R,3R)-2-(2,4-difluorophenyl)-3-(3-ethyl-5,7-difluoro-2H-indazol-2-yl)-1-(1H-1,2,4-triazol-1-yl)butan-2-ol,
198) (2R,3R)-3-(5-chloro-3-ethyl-7-fluoro-1H-indazol-1-yl)-2-(2,4-difluorophenyl)-1-(1H-1,2,4-triazol-1-yl)butan-2-ol,
199) (2R,3R)-3-(5-chloro-3-ethyl-7-fluoro-2H-indazol-2-yl)-2-(2,4-difluorophenyl)-1-(1H-1,2,4-triazol-1-yl)butan-2-ol,
200) (2R,3R)-3-(7-chloro-3-ethyl-5-fluoro-1H-indazol-1-yl)-2-(2,4-difluorophenyl)-1-(1H-1,2,4-triazol-1-yl)butan-2-ol,
201) (2R,3R)-3-(7-chloro-3-ethyl-5-fluoro-2H-indazol-2-yl)-2-(2,4-difluorophenyl)-1-(1H-1,2,4-triazol-1-yl)butan-2-ol,
202) (2R,3R)-3-(5,7-dichloro-3-ethyl-1H-indazol-1-yl)-2-(2,4-difluorophenyl)-1-(1H-1,2,4-triazol-1-yl)butan-2-ol,
203) (2R,3R)-3-(5,7-dichloro-3-ethyl-2H-indazol-2-yl)-2-(2,4-difluorophenyl)-1-(1H-1,2,4-triazol-1-yl)butan-2-ol,
204) (2R,3R)-2-(2,4-difluorophenyl)-3-(3-ethyl-5-fluoro-7-methyl-1H-indazol-1-yl)-1-(1H-1,2,4-triazol-1-yl)butan-2-ol,
205) (2R,3R)-2-(2,4-difluorophenyl)-3-(3-ethyl-5-fluoro-7-methyl-2H-indazol-2-yl)-1-(1H-1,2,4-triazol-1-yl)butan-2-ol,
206) (2R,3R)-3-(5-chloro-3-ethyl-7-methyl-1H-indazol-1-yl)-2-(2,4-difluorophenyl)-1-(1H-1,2,4-triazol-1-yl)butan-2-ol,
207) (2R,3R)-3-(5-chloro-3-ethyl-7-methyl-2H-indazol-2-yl)-2-(2,4-difluorophenyl)-1-(1H-1,2,4-triazol-1-yl)butan-2-ol,
208) (2R,3R)-3-(5-chloro-3-ethyl-6-fluoro-1H-indazol-1-yl)-2-(2,4-difluorophenyl)-1-(1H-1,2,4-triazol-1-yl)butan-2-ol,
209) (2R,3R)-3-(5-chloro-3-ethyl-6-fluoro-2H-indazol-2-yl)-2-(2,4-difluorophenyl)-1-(1H-1,2,4-triazol-1-yl)butan-2-ol,
210) (2R,3R)-2-(2,4-difluorophenyl)-3-(3-ethyl-5-fluoro-6-methyl-1H-indazol-1-yl)-1-(1H-1,2,4-triazol-1-yl)butan-2-ol,
211) (2R,3R)-2-(2,4-difluorophenyl)-3-(3-ethyl-5-fluoro-6-methyl-2H-indazol-2-yl)-1-(1H-1,2,4-triazol-1-yl)butan-2-ol,
212) (2R,3R)-3-(5-chloro-3-ethyl-6-methyl-1H-indazol-1-yl)-2-(2,4-difluorophenyl)-1-(1H-1,2,4-triazol-1-yl)butan-2-ol,
213) (2R,3R)-3-(5-chloro-3-ethyl-6-methyl-2H-indazol-2-yl)-2-(2,4-difluorophenyl)-1-(1H-1,2,4-triazol-1-yl)butan-2-ol,
214) (2R,3R)-3-(6-bromo-3-ethyl-1H-indazol-1-yl)-2-(2,4-difluorophenyl)-1-(1H-1,2,4-triazol-1-yl)butan-2-ol,
215) (2R,3R)-3-(6-bromo-3-ethyl-2H-indazol-2-yl)-2-(2,4-difluorophenyl)-1-(1H-1,2,4-triazol-1-yl)butan-2-ol,
216) (2R,3R)-3-(7-bromo-3-ethyl-1H-indazol-1-yl)-2-(2,4-difluorophenyl)-1-(1H-1,2,4-triazol-1-yl)butan-2-ol,
217) (2R,3R)-3-(7-bromo-3-ethyl-2H-indazol-2-yl)-2-(2,4-difluorophenyl)-1-(1H-1,2,4-triazol-1-yl)butan-2-ol,
218) (2R,3R)-3-(5-bromo-3-ethyl-1H-indazol-1-yl)-2-(2,4-difluorophenyl)-1-(1H-1,2,4-triazol-1-yl)butan-2-ol,
219) (2R,3R)-3-(5-bromo-3-ethyl-2H-indazol-2-yl)-2-(2,4-difluorophenyl)-1-(1H-1,2,4-triazol-1-yl)butan-2-ol,
220) (2R,3R)-3-(3,5-difluoro-1H-indazol-1-yl)-2-(2,4-difluorophenyl)-1-(1H-1,2,4-triazol-1-yl)butan-2-ol,
221) (2R,3R)-3-(3,5-difluoro-2H-indazol-2-yl)-2-(2,4-difluorophenyl)-1-(1H-1,2,4-triazol-1-yl)butan-2-ol,
222) (2R,3R)-3-(5-chloro-3-fluoro-1H-indazol-1-yl)-2-(2,4-difluorophenyl)-1-(1H-1,2,4-triazol-1-yl)butan-2-ol,
223) (2R,3R)-3-(5-chloro-3-fluoro-2H-indazol-2-yl)-2-(2,4-difluorophenyl)-1-(1H-1,2,4-triazol-1-yl)butan-2-ol, 224) (2R,3R)-3-(5-bromo-3-fluoro-1H-indazol-1-yl)-2-(2,4-difluorophenyl)-1-(1H-1,2,4-triazol-1-yl)butan-2-ol,
225) (2R,3R)-3-(5-bromo-3-fluoro-2H-indazol-2-yl)-2-(2,4-difluorophenyl)-1-(1H-1,2,4-triazol-1-yl)butan-2-ol,
226) 1-((2R,3R)-3-(2,4-difluorophenyl)-3-hydroxy-4-(1H-1,2,4-triazol-1-yl)butan-2-yl)-3-fluoro-1H-indazole-5-carbonitrile,
227) 2-((2R,3R)-3-(2,4-difluorophenyl)-3-hydroxy-4-(1H-1,2,4-triazol-1-yl)butan-2-yl)-3-fluoro-2H-indazole-5-carbonitrile,
228) (2R,3R)-3-(3-amino-5-fluoro-1H-indazol-1-yl)-2-(2,4-difluorophenyl)-1-(1H-1,2,4-triazol-1-yl)butan-2-ol,
229) (2R,3R)-3-(3-amino-5-fluoro-2H-indazol-2-yl)-2-(2,4-difluorophenyl)-1-(1H-1,2,4-triazol-1-yl)butan-2-ol,
230) (2R,3R)-3-(3-amino-5-chloro-1H-indazol-1-yl)-2-(2,4-difluorophenyl)-1-(1H-1,2,4-triazol-1-yl)butan-2-ol,
231) (2R,3R)-3-(3-amino-5-chloro-2H-indazol-2-yl)-2-(2,4-difluorophenyl)-1-(1H-1,2,4-triazol-1-yl)butan-2-ol,
232) (2R,3R)-2-(2,4-difluorophenyl)-3-(5-nitro-1H-indazol-1-yl)-1-(1H-1,2,4-triazol-1-yl)butan-2-ol,
233) (2R,3R)-2-(2,4-difluorophenyl)-3-(5-nitro-2H-indazol-2-yl)-1-(1H-1,2,4-triazol-1-yl)butan-2-ol,
234) (2R,3R)-3-(5-amino-1H-indazol-1-yl)-2-(2,4-difluorophenyl)-1-(1H-1,2,4-triazol-1-yl)butan-2-ol,
235) (2R,3R)-3-(5-amino-2H-indazol-2-yl)-2-(2,4-difluorophenyl)-1-(1H-1,2,4-triazol-1-yl)butan-2-ol,
236) (2R,3R)-3-(5-(benzylamino)-2H-indazol-2-yl)-2-(2,4-difluorophenyl)-1-(1H-1,2,4-triazol-1-yl)butan-2-ol,
237) (2R,3R)-2-(2,4-difluorophenyl)-3-(5-(2-nitrobenzylamino)-2H-indazol-2-yl)-1-(1H-1,2,4-triazol-1-yl)butan-2-ol,
238) (2R,3R)-3-(5-(3-chlorobenzylamino)-2H-indazol-2-yl)-2-(2,4-difluorophenyl)-1-(1H-1,2,4-triazol-1-yl)butan-2-ol,
239) (2R,3R)-2-(2,4-difluorophenyl)-1-(1H-1,2,4-triazol-1-yl)-3-(5-(3-(trifluoromethyl)benzylamino)-2H-indazol-2-yl)butan-2-ol,
240) (2R,3R)-2-(2,4-difluorophenyl)-3-(5-(3-nitrobenzylamino)-2H-indazol-2-yl)-1-(1H-1,2,4-triazol-1-yl)butan-2-ol,
241) (2R,3R)-3-(5-(4-bromobenzylamino)-2H-indazol-2-yl)-2-(2,4-difluorophenyl)-1-(1H-1,2,4-triazol-1-yl)butan-2-ol,
242) (2R,3R)-2-(2,4-difluorophenyl)-3-(5-(4-fluorobenzylamino)-2H-indazol-2-yl)-1-(1H-1,2,4-triazol-1-yl)butan-2-ol,
243) (2R,3R)-3-(5-(4-chlorobenzylamino)-2H-indazol-2-yl)-2-(2,4-difluorophenyl)-1-(1H-1,2,4-triazol-1-yl)butan-2-ol,
244) (2R,3R)-2-(2,4-difluorophenyl)-1-(1H-1,2,4-triazol-1-yl)-3-(5-(4-(trifluoromethyl)benzylamino)-2H-indazol-2-yl)butan-2-ol,
245) (2R,3R)-2-(2,4-difluorophenyl)-1-(1H-1,2,4-triazol-1-yl)-3-(5-(4-(trifluoromethoxy)benzylamino)-2H-indazol-2-yl)butan-2-ol,
246) (2R,3R)-2-(2,4-difluorophenyl)-3-(5-(4-nitrobenzylamino)-1H-indazol-1-yl)-1-(1H-1,2,4-triazol-1-yl)butan-2-ol,
247) (2R,3R)-3-(5-(4-aminobenzylamino)-1H-indazol-1-yl)-2-(2,4-difluorophenyl)-1-(1H-1,2,4-triazol-1-yl)butan-2-ol,
248) (2R,3R)-3-(5-(2,4-difluorobenzylamino)-2H-indazol-2-yl)-2-(2,4-difluorophenyl)-1-(1H-1,2,4-triazol-1-yl)butan-2-ol,
249) (2R,3R)-3-(5-(2,4-dichlorobenzylamino)-2H-indazol-2-yl)-2-(2,4-difluorophenyl)-1-(1H-1,2,4-triazol-1-yl)butan-2-ol,
250) (2R,3R)-3-(5-(4-chloro-2-nitrobenzylamino)-2H-indazol-2-yl)-2-(2,4-difluorophenyl)-1-(1H-1,2,4-triazol-1-yl)butan-2-ol,
251) (2R,3R)-3-(5-(2,6-difluorobenzylamino)-2H-indazol-2-yl)-2-(2,4-difluorophenyl)-1-(1H-1,2,4-triazol-1-yl)butan-2-ol,
252) (2R,3R)-3-(5-(2,6-dichlorobenzylamino)-2H-indazol-2-yl)-2-(2,4-difluorophenyl)-1-(1H-1,2,4-triazol-1-yl)butan-2-ol,
253) (2R,3R)-3-(5-(2-chloro-6-fluorobenzylamino)-1H-indazol-1-yl)-2-(2,4-difluorophenyl)-1-(1H-1,2,4-triazol-1-yl)butan-2-ol,
254) (2R,3R)-3-(5-(3,4-dichlorobenzylamino)-2H-indazol-2-yl)-2-(2,4-difluorophenyl)-1-(1H-1,2,4-triazol-1-yl)butan-2-ol,
255) (2R,3R)-2-(2,4-difluorophenyl)-3-(5-(3,4-dimethylbenzylamino)-2H-indazol-2-yl)-1-(1H-1,2,4-triazol-1-yl)butan-2-ol,
256) (2R,3R)-3-(5-(3,5-difluorobenzylamino)-2H-indazol-2-yl)-2-(2,4-difluorophenyl)-1-(1H-1,2,4-triazol-1-yl)butan-2-ol,
257) (2R,3R)-2-(2,4-difluorophenyl)-3-(5-(3,5-dimethoxybenzylamino)-2H-indazol-2-yl)-1-(1H-1,2,4-triazol-1-yl)butan-2-ol,
258) (2R,3R)-3-(5-(dibenzylamino)-1H-indazol-1-yl)-2-(2,4-difluorophenyl)-1-(1H-1,2,4-triazol-1-yl)butan-2-ol,
259) (2R,3R)-3-(5-(bis(2-nitrobenzyl)amino)-2H-indazol-2-yl)-2-(2,4-difluorophenyl)-1-(1H-1,2,4-triazol-1-yl)butan-2-ol,
260) (2R,3R)-3-(5-(bis(3-chlorobenzyl)amino)-2H-indazol-2-yl)-2-(2,4-difluorophenyl)-1-(1H-1,2,4-triazol-1-yl)butan-2-ol,
261) (2R,3R)-3-(5-(bis(3-(trifluoromethyl)benzyl)amino)-2H-indazol-2-yl)-2-(2,4-difluorophenyl)-1-(1H-1,2,4-triazol-1-yl)butan-2-ol,
262) (2R,3R)-3-(5-(bis(3-nitrobenzyl)amino)-2H-indazol-2-yl)-2-(2,4-difluorophenyl)-1-(1H-1,2,4-triazol-1-yl)butan-2-ol,
263) (2R,3R)-3-(5-(bis(4-fluorobenzyl)amino)-2H-indazol-2-yl)-2-(2,4-difluorophenyl)-1-(1H-1,2,4-triazol-1-yl)butan-2-ol,
264) (2R,3R)-3-(5-(bis(4-chlorobenzyl)amino)-2H-indazol-2-yl)-2-(2,4-difluorophenyl)-1-(1H-1,2,4-triazol-1-yl)butan-2-ol,
265) (2R,3R)-3-(5-(bis(4-bromobenzyl)amino)-2H-indazol-2-yl)-2-(2,4-difluorophenyl)-1-(1H-1,2,4-triazol-1-yl)butan-2-ol,
266) (2R,3R)-3-(5-(bis(4-(trifluoromethyl)benzyl)amino)-2H-indazol-2-yl)-2-(2,4-difluorophenyl)-1-(1H-1,2,4-triazol-1-yl)butan-2-ol,
267) 4,4'-(2-((2R,3R)-3-(2,4-difluorophenyl)-3-hydroxy-4-(1H-1,2,4-triazol-1-yl)butan-2-yl)-2H-indazol-5-ylazanediyl)bis(methylene)dibenzonitrile,
268) (2R,3R)-3-(5-(bis(4-nitrobenzyl)amino)-1H-indazol-1-yl)-2-(2,4-difluorophenyl)-1-(1H-1,2,4-triazol-1-yl)butan-2-ol,
269) (2R,3R)-3-(5-(bis(4-nitrobenzyl)amino)-2H-indazol-2-yl)-2-(2,4-difluorophenyl)-1-(1H-1,2,4-triazol-1-yl)butan-2-ol, 270) (2R,3R)-3-(5-(bis(4-(trifluoromethoxy)benzyl)amino)-2H-indazol-2-yl)-2-(2,4-difluorophenyl)-1-(1H-1,2,4-triazol-1-yl)butan-2-ol,
271) dimethyl 4,4'-(2-((2R,3R)-3-(2,4-difluorophenyl)-3-hydroxy-4-(1H-1,2,4-triazol-1-yl)butan-2-yl)-2H-indazol-5-ylazanediyl)bis(methylene)dibenzoate,
272) (2R,3R)-3-(5-(bis(2,4-difluorobenzyl)amino)-2H-indazol-2-yl)-2-(2,4-difluorophenyl)-1-(1H-1,2,4-triazol-1-yl)butan-2-ol,
273) (2R,3R)-3-(5-(bis(2,4-dichlorobenzyl)amino)-2H-indazol-2-yl)-2-(2,4-difluorophenyl)-1-(1H-1,2,4-triazol-1-yl)butan-2-ol,
274) (2R,3R)-3-(5-(bis(4-chloro-2-nitrobenzyl)amino)-2H-indazol-2-yl)-2-(2,4-difluorophenyl)-1-(1H-1,2,4-triazol-1-yl)butan-2-ol,
275) (2R,3R)-3-(5-(bis(2,6-difluorobenzyl)amino)-2H-indazol-2-yl)-2-(2,4-difluorophenyl)-1-(1H-1,2,4-triazol-1-yl)butan-2-ol,
276) (2R,3R)-3-(5-(bis(2,6-dichlorobenzyl)amino)-2H-indazol-2-yl)-2-(2,4-difluorophenyl)-1-(1H-1,2,4-triazol-1-yl)butan-2-ol,
277) (2R,3R)-3-(5-(bis(2-chloro-6-fluorobenzyl)amino)-2H-indazol-2-yl)-2-(2,4-difluorophenyl)-1-(1H-1,2,4-triazol-1-yl)butan-2-ol,
278) (2R,3R)-3-(5-(bis(4-methyl-3-nitrobenzyl)amino)-2H-indazol-2-yl)-2-(2,4-difluorophenyl)-1-(1H-1,2,4-triazol-1-yl)butan-2-ol,
279) (2R,3R)-3-(5-(bis(3,4-dichlorobenzyl)amino)-2H-indazol-2-yl)-2-(2,4-difluorophenyl)-1-(1H-1,2,4-triazol-1-yl)butan-2-ol,
280) (2R,3R)-3-(5-(bis(3,4-dimethylbenzyl)amino)-2H-indazol-2-yl)-2-(2,4-difluorophenyl)-1-(1H-1,2,4-triazol-1-yl)butan-2-ol,
281) (2R,3R)-3-(5-(bis(3,5-difluorobenzyl)amino)-2H-indazol-2-yl)-2-(2,4-difluorophenyl)-1-(1H-1,2,4-triazol-1-yl)butan-2-ol,
282) (2R,3R)-3-(5-(bis(3,5-dimethoxybenzyl)amino)-2H-indazol-2-yl)-2-(2,4-difluorophenyl)-1-(1H-1,2,4-triazol-1-yl)butan-2-ol,
283) (2R,3R)-3-(5-(bis(perfluorobenzyl)amino)-2H-indazol-2-yl)-2-(2,4-difluorophenyl)-1-(1H-1,2,4-triazol-1-yl)butan-2-ol,
284) N-(1-((2R,3R)-3-(2,4-difluorophenyl)-3-hydroxy-4-(1H-1,2,4-triazol-1-yl)butan-2-yl)-1H-indazol-5-yl)benzenesulfonamide,
285) N-(1-((2R,3R)-3-(2,4-difluorophenyl)-3-hydroxy-4-(1H-1,2,4-triazol-1-yl)butan-2-yl)-1H-indazol-5-yl)-2-methylbenzenesulfonamide,
286) 2-chloro-N-(1-((2R,3R)-3-(2,4-difluorophenyl)-3-hydroxy-4-(1H-1,2,4-triazol-1-yl)butan-2-yl)-1H-indazol-5-yl)benzenesulfonamide,
287) N-(1-((2R,3R)-3-(2,4-difluorophenyl)-3-hydroxy-4-(1H-1,2,4-triazol-1-yl)butan-2-yl)-1H-indazol-5-yl)-3-methylbenzenesulfonamide,
288) 3-chloro-N-(1-((2R,3R)-3-(2,4-difluorophenyl)-3-hydroxy-4-(1H-1,2,4-triazol-1-yl)butan-2-yl)-1H-indazol-5-yl)benzenesulfonamide,
289) N-(1-((2R,3R)-3-(2,4-difluorophenyl)-3-hydroxy-4-(1H-1,2,4-triazol-1-yl)butan-2-yl)-1H-indazol-5-yl)-4-methylbenzenesulfonamide,
290) N-(1-((2R,3R)-3-(2,4-difluorophenyl)-3-hydroxy-4-(1H-1,2,4-triazol-1-yl)butan-2-yl)-1H-indazol-5-yl)-4-fluorobenzenesulfonamide,
291) 4-chloro-N-(1-((2R,3R)-3-(2,4-difluorophenyl)-3-hydroxy-4-(1H-1,2,4-triazol-1-yl)butan-2-yl)-1H-indazol-5-yl)benzenesulfonamide,
292) 4-bromo-N-(1-((2R,3R)-3-(2,4-difluorophenyl)-3-hydroxy-4-(1H-1,2,4-triazol-1-yl)butan-2-yl)-1H-indazol-5-yl)benzenesulfonamide,
293) N-(1-((2R,3R)-3-(2,4-difluorophenyl)-3-hydroxy-4-(1H-1,2,4-triazol-1-yl)butan-2-yl)-1H-indazol-5-yl)-4-nitrobenzenesulfonamide,
294) N-(1-((2R,3R)-3-(2,4-difluorophenyl)-3-hydroxy-4-(1H-1,2,4-triazol-1-yl)butan-2-yl)-1H-indazol-5-yl)-4-(trifluoromethyl)benzenesulfonamide,
295) 4-tert-butyl-N-(1-((2R,3R)-3-(2,4-difluorophenyl)-3-hydroxy-4-(1H-1,2,4-triazol-1-yl)butan-2-yl)-1H-indazol-5-yl)benzenesulfonamide,
296) N-(1-((2R,3R)-3-(2,4-difluorophenyl)-3-hydroxy-4-(1H-1,2,4-triazol-1-yl)butan-2-yl)-1H-indazol-5-yl)-4-methoxybenzenesulfonamide,
297) 2,3-dichloro-N-(1-((2R,3R)-3-(2,4-difluorophenyl)-3-hydroxy-4-(1H-1,2,4-triazol-1-yl)butan-2-yl)-1H-indazol-5-yl)benzenesulfonamide,
298) 2,5-dichloro-N-(1-((2R,3R)-3-(2,4-difluorophenyl)-3-hydroxy-4-(1H-1,2,4-triazol-1-yl)butan-2-yl)-1H-indazol-5-yl)benzenesulfonamide,
299) 2,4-dichloro-N-(1-((2R,3R)-3-(2,4-difluorophenyl)-3-hydroxy-4-(1H-1,2,4-triazol-1-yl)butan-2-yl)-1H-indazol-5-yl)benzenesulfonamide,
300) 3,4-dichloro-N-(1-((2R,3R)-3-(2,4-difluorophenyl)-3-hydroxy-4-(1H-1,2,4-triazol-1-yl)butan-2-yl)-1H-indazol-5-yl)benzenesulfonamide,
301) 3,5-dichloro-N-(1-((2R,3R)-3-(2,4-difluorophenyl)-3-hydroxy-4-(1H-1,2,4-triazol-1-yl)butan-2-yl)-1H-indazol-5-yl)benzenesulfonamide,
302) N-(1-((2R,3R)-3-(2,4-difluorophenyl)-3-hydroxy-4-(1H-1,2,4-triazol-1-yl)butan-2-yl)-1H-indazol-5-yl)naphthalene-1-sulfonamide,
303) N-(1-((2R,3R)-3-(2,4-difluorophenyl)-3-hydroxy-4-(1H-1,2,4-triazol-1-yl)butan-2-yl)-1H-indazol-5-yl)-1-m-tolylmethanesulfonamide,
304) (2R,3R)-2-(2,4-difluorophenyl)-3-(5-(isobutylamino)-1H-indazol-1-yl)-1-(1H-1,2,4-triazol-1-yl)butan-2-ol,
305) (2R,3R)-2-(2,4-difluorophenyl)-3-(5-(isopentylamino)-1H-indazol-1-yl)-1-(1H-1,2,4-triazol-1-yl)butan-2-ol,
306) (2R,3R)-2-(2,4-difluorophenyl)-3-(5-(2-ethylbutylamino)-1H-indazol-1-yl)-1-(1H-1,2,4-triazol-1-yl)butan-2-ol,
307) (2R,3R)-3-(5-(cyclohexylmethylamino)-1H-indazol-1-yl)-2-(2,4-difluorophenyl)-1-(1H-1,2,4-triazol-1-yl)butan-2-ol,
308) (2R,3R)-2-(2,4-difluorophenyl)-3-(5-(dimethylamino)-1H-indazol-1-yl)-1-(1H-1,2,4-triazol-1-yl)butan-2-ol,
309) (2R,3R)-2-(2,4-difluorophenyl)-3-(5-(diisobutylamino)-1H-indazol-1-yl)-1-(1H-1,2,4-triazol-1-yl)butan-2-ol,
310) (2R,3R)-2-(2,4-difluorophenyl)-3-(5-(diisopentylamino)-1H-indazol-1-yl)-1-(1H-1,2,4-triazol-1-yl)butan-2-ol,
311) (2R,3R)-3-(5-(bis(2-ethylbutyl)amino)-1H-indazol-1-yl)-2-(2,4-difluorophenyl)-1-(1H-1,2,4-triazol-1-yl)butan-2-ol,
312) (2R,3R)-3-(5-(bis(cyclohexylmethyl)amino)-1H-indazol-1-yl)-2-(2,4-difluorophenyl)-1-(1H-1,2,4-triazol-1-yl)butan-2-ol,
313) (2R,3R)-3-(5-((4-chlorobenzyl)(ethyl)amino)-2H-indazol-2-yl)-2-(2,4-difluorophenyl)-1-(1H-1,2,4-triazol-1-yl)butan-2-ol, 314) (2R,3R)-3-(5-((4-chlorobenzyl)(isopropyl)amino)-2H-indazol-2-yl)-2-(2,4-difluorophenyl)-1-(1H-1,2,4-triazol-1-yl)butan-2-ol,
315) (2R,3R)-3-(5-((4-chlorobenzyl)(propyl)amino)-2H-indazol-2-yl)-2-(2,4-difluorophenyl)-1-(1H-1,2,4-triazol-1-yl)butan-2-ol,
316) (2R,3R)-3-(5-((4-chlorobenzyl)(isobutyl)amino)-2H-indazol-2-yl)-2-(2,4-difluorophenyl)-1-(1H-1,2,4-triazol-1-yl)butan-2-ol,
317) (2R,3R)-3-(5-((4-chlorobenzyl)(isopentyl)amino)-2H-indazol-2-yl)-2-(2,4-difluorophenyl)-1-(1H-1,2,4-triazol-1-yl)butan-2-ol,
318) (2R,3R)-3-(5-((4-chlorobenzyl)(3-ethylpentyl)amino)-2H-indazol-2-yl)-2-(2,4-difluorophenyl)-1-(1H-1,2,4-triazol-1-yl)butan-2-ol,
319) (2R,3R)-3-(5-((4-chlorobenzyl)(2-ethylbutyl)amino)-2H-indazol-2-yl)-2-(2,4-difluorophenyl)-1-(1H-1,2,4-triazol-1-yl)butan-2-ol,
320) (2R,3R)-3-(5-((4-chlorobenzyl)(cyclopentyl)amino)-2H-indazol-2-yl)-2-(2,4-difluorophenyl)-1-(1H-1,2,4-triazol-1-yl)butan-2-ol,
321) (2R,3R)-3-(5-((4-chlorobenzyl)(cyclohexylmethyl)amino)-2H-indazol-2-yl)-2-(2,4-difluorophenyl)-1-(1H-1,2,4-triazol-1-yl)butan-2-ol,
322) (2R,3R)-3-(5-(tert-butyl(4-chlorobenzyl)amino)-2H-indazol-2-yl)-2-(2,4-difluorophenyl)-1-(1H-1,2,4-triazol-1-yl)butan-2-ol,
323) (2R,3R)-3-(5-((4-chlorobenzyl)(2-hydroxyethyl)amino)-2H-indazol-2-yl)-2-(2,4-difluorophenyl)-1-(1H-1,2,4-triazol-1-yl)butan-2-ol,
324) (2R,3R)-3-(5-(sec-butyl(4-chlorobenzyl)amino)-2H-indazol-2-yl)-2-(2,4-difluorophenyl)-1-(1H-1,2,4-triazol-1-yl)butan-2-ol,
325) (2R,3R)-3-(5-((4-chlorobenzyl)(tert-pentyl)amino)-2H-indazol-2-yl)-2-(2,4-difluorophenyl)-1-(1H-1,2,4-triazol-1-yl)butan-2-ol,
326) (2R,3R)-3-(5-((2-(1,3-dioxolan-2-yl)ethyl)(4-chlorobenzyl)amino)-2H-indazol-2-yl)-2-(2,4-difluorophenyl)-1-(1H-1,2,4-triazol-1-yl)butan-2-ol,
327) (2R,3R)-3-(5-((2-(1,3-dioxan-2-yl)ethyl)(4-chlorobenzyl)amino)-2H-indazol-2-yl)-2-(2,4-difluorophenyl)-1-(1H-1,2,4-triazol-1-yl)butan-2-ol,
328) (2R,3R)-3-(5-((4-chlorobenzyl)(3-hydroxypropyl)amino)-2H-indazol-2-yl)-2-(2,4-difluorophenyl)-1-(1H-1,2,4-triazol-1-yl)butan-2-ol,
329) (2R,3R)-2-(2,4-difluorophenyl)-3-(5-(isobutyl(propyl)amino)-1H-indazol-1-yl)-1-(1H-1,2,4-triazol-1-yl)butan-2-ol,
330) (2R,3R)-2-(2,4-difluorophenyl)-3-(5-(isobutyl(neopentyl)amino)-1H-indazol-1-yl)-1-(1H-1,2,4-triazol-1-yl)butan-2-ol,
331) (2R,3R)-2-(2,4-difluorophenyl)-3-(5-(isobutyl(isopentyl)amino)-1H-indazol-1-yl)-1-(1H-1,2,4-triazol-1-yl)butan-2-ol,
332) (2R,3R)-2-(2,4-difluorophenyl)-3-(5-(isopentyl(propyl)amino)-1H-indazol-1-yl)-1-(1H-1,2,4-triazol-1-yl)butan-2-ol,
333) (2R,3R)-2-(2,4-difluorophenyl)-3-(5-(isopentyl(neopentyl)amino)-1H-indazol-1-yl)-1-(1H-1,2,4-triazol-1-yl)butan-2-ol,
334) (2R,3R)-2-(2,4-difluorophenyl)-3-(5-((2-ethylbutyl)(isobutyl)amino)-1H-indazol-1-yl)-1-(1H-1,2,4-triazol-1-yl)butan-2-ol,
335) (2R,3R)-2-(2,4-difluorophenyl)-3-(5-((2-ethylbutyl)(isobutyl)amino)-1H-indazol-1-yl)-1-(1H-1,2,4-triazol-1-yl)butan-2-ol,
336) (2R,3R)-2-(2,4-difluorophenyl)-3-(5-((2-ethylbutyl)(propyl)amino)-1H-indazol-1-yl)-1-(1H-1,2,4-triazol-1-yl)butan-2-ol,
337) (2R,3R)-2-(2,4-difluorophenyl)-3-(5-((2-ethylbutyl)(neopentyl)amino)-1H-indazol-1-yl)-1-(1H-1,2,4-triazol-1-yl)butan-2-ol,
338) (2R,3R)-2-(2,4-difluorophenyl)-3-(5-((2-ethylbutyl)((tetrahydro-2H-pyran-2-yl)methyl)amino)-1H-indazol-1-yl)-1-(1H-1,2,4-triazol-1-yl)butan-2-ol,
339) (2R,3R)-3-(5-((cyclohexylmethyl)(isobutyl)amino)-1H-indazol-1-yl)-2-(2,4-difluorophenyl)-1-(1H-1,2,4-triazol-1-yl)butan-2-ol,
340) (2R,3R)-3-(5-((cyclohexylmethyl)(isopentyl)amino)-1H-indazol-1-yl)-2-(2,4-difluorophenyl)-1-(1H-1,2,4-triazol-1-yl)butan-2-ol,
341) (2R,3R)-3-(5-((cyclohexylmethyl)(2-ethylbutyl)amino)-1H-indazol-1-yl)-2-(2,4-difluorophenyl)-1-(1H-1,2,4-triazol-1-yl)butan-2-ol,
342) (2R,3R)-3-(5-((cyclohexylmethyl)(propyl)amino)-1H-indazol-1-yl)-2-(2,4-difluorophenyl)-1-(1H-1,2,4-triazol-1-yl)butan-2-ol,
343) (2R,3R)-3-(5-((cyclohexylmethyl)(neopentyl)amino)-1H-indazol-1-yl)-2-(2,4-difluorophenyl)-1-(1H-1,2,4-triazol-1-yl)butan-2-ol,
344) (2R,3R)-3-(5-((cyclohexylmethyl)((tetrahydro-2H-pyran-2-yl)methyl)amino)-1H-indazol-1-yl)-2-(2,4-difluorophenyl)-1-(1H-1,2,4-triazol-1-yl)butan-2-ol,
345) tert-butyl 4-((1-((2R,3R)-3-(2,4-difluorophenyl)-3-hydroxy-4-(1H-1,2,4-triazol-1-yl)butan-2-yl)-1H-indazol-5-yl)amino)piperidine-1-carboxylate,
346) (2R,3R)-2-(2,4-difluorophenyl)-3-(5-(piperidin-4-ylamino)-1H-indazol-1-yl)-1-(1H-1,2,4-triazol-1-yl)butan-2-ol,
347) (2R,3R)-2-(2,4-difluorophenyl)-3-(5-(tetrahydro-2H-pyran-4-ylamino)-1H-indazol-1-yl)-1-(1H-1,2,4-triazol-1-yl)butan-2-ol,
348) (2R,3R)-2-(2,4-difluorophenyl)-3-(5-(tetrahydro-2H-pyran-4-ylamino)-2H-indazol-2-yl)-1-(1H-1,2,4-triazol-1-yl)butan-2-ol,
349) (2R,3R)-2-(2,4-difluorophenyl)-3-(5-(tetrahydro-2H-thiopyran-4-ylamino)-2H-indazol-2-yl)-1-(1H-1,2,4-triazol-1-yl)butan-2-ol,
350) (2R,3R)-3-(5-(cyclopentylamino)-1H-indazol-1-yl)-2-(2,4-difluorophenyl)-1-(1H-1,2,4-triazol-1-yl)butan-2-ol,
351) (2R,3R)-3-(5-(cyclopentylamino)-2H-indazol-2-yl)-2-(2,4-difluorophenyl)-1-(1H-1,2,4-triazol-1-yl)butan-2-ol,
352) (2R,3R)-2-(2,4-difluorophenyl)-3-(5-(1-ethylpiperidin-4-ylamino)-1H-indazol-1-yl)-1-(1H-1,2,4-triazol-1-yl)butan-2-ol,
353) 1-(4-(1-((2R,3R)-3-(2,4-difluorophenyl)-3-hydroxy-4-(1H-1,2,4-triazol-1-yl)butan-2-yl)-1H-indazol-5-ylamino)piperidin-1-yl)ethanone,
354) (2R,3R)-2-(2,4-difluorophenyl)-3-(5-(1-isopropylpiperidin-4-ylamino)-1H-indazol-1-yl)-1-(1H-1,2,4-triazol-1-yl)butan-2-ol,
355) (2R,3R)-2-(2,4-difluorophenyl)-3-(5-(2-methylcyclohexylamino)-1H-indazol-1-yl)-1-(1H-1,2,4-triazol-1-yl)butan-2-ol,
356) (2R,3R)-2-(2,4-difluorophenyl)-3-(5-(4-methylcyclohexylamino)-1H-indazol-1-yl)-1-(1H-1,2,4-triazol-1-yl)butan-2-ol,
357) (2R,3R)-2-(2,4-difluorophenyl)-3-(5-(3-methylcyclohexylamino)-1H-indazol-1-yl)-1-(1H-1,2,4-triazol-1-yl)butan-2-ol, 358) (2R,3R)-2-(2,4-difluorophenyl)-3-(5-(3,4-dimethylcyclohexylamino)-1H-indazol-1-yl)-1-(1H-1,2,4-triazol-1-yl)butan-2-ol, 359) (2R,3R)-2-(2,4-difluorophenyl)-3-(5-(3,5-dimethylcyclohexylamino)-1H-indazol-1-yl)-1-(1H-1,2,4-triazol-1-yl)butan-2-ol, 360) (2R,3R)-3-(5-(4-tert-butylcyclohexylamino)-1H-indazol-1-yl)-2-(2,4-difluorophenyl)-1-(1H-1,2,4-triazol-1-yl)butan-2-ol, 361) (2R,3R)-2-(2,4-difluorophenyl)-3-(5-(4-phenylcyclohexylamino)-1H-indazol-1-yl)-1-(1H-1,2,4-triazol-1-yl)butan-2-ol, 362) (2R,3R)-2-(2,4-difluorophenyl)-3-(5-(1-ethylpiperidin-3-ylamino)-1H-indazol-1-yl)-1-(1H-1,2,4-triazol-1-yl)butan-2-ol, 363) (2R,3R)-2-(2,4-difluorophenyl)-3-(5-(1-ethylpiperidin-3-ylamino)-2H-indazol-2-yl)-1-(1H-1,2,4-triazol-1-yl)butan-2-ol, 364) (4-(1-((2R,3R)-3-(2,4-difluorophenyl)-3-hydroxy-4-(1H-1,2,4-triazol-1-yl)butan-2-yl)-1H-indazol-5-ylamino)piperidin-1-yl)(phenyl)methanone, 365) 4-((1-((2R,3R)-3-(2,4-difluorophenyl)-3-hydroxy-4-(1H-1,2,4-triazol-1-yl)butan-2-yl)-1H-indazol-5-yl)amino)tetrahydro-2H-thiopyran 1,1-dioxide, 366) (2R,3R)-3-(5-(4-chlorobenzylamino)-3-methyl-1H-indazol-1-yl)-2-(2,4-difluorophenyl)-1-(1H-1,2,4-triazol-1-yl)butan-2-ol, 367) (2R,3R)-2-(2,4-difluorophenyl)-3-(5-(4-fluorobenzylamino)-3-methyl-1H-indazol-1-yl)-1-(1H-1,2,4-triazol-1-yl)butan-2-ol, 368) (2R,3R)-2-(2,4-difluorophenyl)-3-(5-(4-fluorobenzylamino)-3-methyl-2H-indazol-2-yl)-1-(1H-1,2,4-triazol-1-yl)butan-2-ol, 369) (2R,3R)-3-(5-(4-chlorobenzylamino)-3-methyl-2H-indazol-2-yl)-2-(2,4-difluorophenyl)-1-(1H-1,2,4-triazol-1-yl)butan-2-ol, 370) (2R,3R)-3-(5-(2,4-dichlorobenzylamino)-3-methyl-1H-indazol-1-yl)-2-(2,4-difluorophenyl)-1-(1H-1,2,4-triazol-1-yl)butan-2-ol, 371) (2R,3R)-3-(5-(2,4-dichlorobenzylamino)-3-methyl-2H-indazol-2-yl)-2-(2,4-difluorophenyl)-1-(1H-1,2,4-triazol-1-yl)butan-2-ol, 372) (2R,3R)-3-(6-(4-chlorobenzylamino)-3-methyl-1H-indazol-1-yl)-2-(2,4-difluorophenyl)-1-(1H-1,2,4-triazol-1-yl)butan-2-ol, 373) (2R,3R)-3-(6-(4-chlorobenzylamino)-3-methyl-2H-indazol-2-yl)-2-(2,4-difluorophenyl)-1-(1H-1,2,4-triazol-1-yl)butan-2-ol, 374) (2R,3R)-3-(5-(4-chlorobenzylamino)-7-fluoro-3-methyl-1H-indazol-1-yl)-2-(2,4-difluorophenyl)-1-(1H-1,2,4-triazol-1-yl)butan-2-ol, 375) (2R,3R)-3-(5-(4-chlorobenzylamino)-7-fluoro-3-methyl-2H-indazol-2-yl)-2-(2,4-difluorophenyl)-1-(1H-1,2,4-triazol-1-yl)butan-2-ol, 376) (2R,3R)-3-(7-chloro-5-(4-chlorobenzylamino)-3-methyl-1H-indazol-1-yl)-2-(2,4-difluorophenyl)-1-(1H-1,2,4-triazol-1-yl)butan-2-ol, 377) (2R,3R)-3-(7-chloro-5-(4-chlorobenzylamino)-3-methyl-2H-indazol-2-yl)-2-(2,4-difluorophenyl)-1-(1H-1,2,4-triazol-1-yl)butan-2-ol, 378) (2R,3R)-3-(5-(4-chlorobenzylamino)-6-fluoro-3-methyl-1H-indazol-1-yl)-2-(2,4-difluorophenyl)-1-(1H-1,2,4-triazol-1-yl)butan-2-ol, 379) (2R,3R)-3-(5-(4-chlorobenzylamino)-6-fluoro-3-methyl-2H-indazol-2-yl)-2-(2,4-difluorophenyl)-1-(1H-1,2,4-triazol-1-yl)butan-2-ol, 380) (2R,3R)-3-(6-(4-chlorobenzylamino)-3-ethyl-1H-indazol-1-yl)-2-(2,4-difluorophenyl)-1-(1H-1,2,4-triazol-1-yl)butan-2-ol, 381) (2R,3R)-3-(6-(4-chlorobenzylamino)-3-ethyl-2H-indazol-2-yl)-2-(2,4-difluorophenyl)-1-(1H-1,2,4-triazol-1-yl)butan-2-ol, 382) (2R,3R)-3-(5-(4-chlorobenzylamino)-3-ethyl-1H-indazol-1-yl)-2-(2,4-difluorophenyl)-1-(1H-1,2,4-triazol-1-yl)butan-2-ol, 383) (2R,3R)-3-(5-(4-chlorobenzylamino)-3-ethyl-2H-indazol-2-yl)-2-(2,4-difluorophenyl)-1-(1H-1,2,4-triazol-1-yl)butan-2-ol, 384) (2R,3R)-3-(5-(4-chlorobenzylamino)-3-ethyl-7-fluoro-1H-indazol-1-yl)-2-(2,4-difluorophenyl)-1-(1H-1,2,4-triazol-1-yl)butan-2-ol, 385) (2R,3R)-3-(5-(4-chlorobenzylamino)-3-ethyl-7-fluoro-2H-indazol-2-yl)-2-(2,4-difluorophenyl)-1-(1H-1,2,4-triazol-1-yl)butan-2-ol, 386) (2R,3R)-3-(7-chloro-5-(4-chlorobenzylamino)-3-ethyl-1H-indazol-1-yl)-2-(2,4-difluorophenyl)-1-(1H-1,2,4-triazol-1-yl)butan-2-ol, 387) (2R,3R)-3-(7-chloro-5-(4-chlorobenzylamino)-3-ethyl-2H-indazol-2-yl)-2-(2,4-difluorophenyl)-1-(1H-1,2,4-triazol-1-yl)butan-2-ol, 388) (2R,3R)-3-(5-(4-chlorobenzylamino)-3-ethyl-6-fluoro-1H-indazol-1-yl)-2-(2,4-difluorophenyl)-1-(1H-1,2,4-triazol-1-yl)butan-2-ol, 389) (2R,3R)-3-(5-(4-chlorobenzylamino)-3-ethyl-6-fluoro-2H-indazol-2-yl)-2-(2,4-difluorophenyl)-1-(1H-1,2,4-triazol-1-yl)butan-2-ol, 390) (2R,3R)-3-(5-(4-chlorobenzylamino)-3-fluoro-1H-indazol-1-yl)-2-(2,4-difluorophenyl)-1-(1H-1,2,4-triazol-1-yl)butan-2-ol, 391) (2R,3R)-3-(5-(4-chlorobenzylamino)-3-fluoro-2H-indazol-2-yl)-2-(2,4-difluorophenyl)-1-(1H-1,2,4-triazol-1-yl)butan-2-ol, 392) (2R,3R)-3-(5-(bis(4-fluorobenzyl)amino)-3-methyl-2H-indazol-2-yl)-2-(2,4-difluorophenyl)-1-(1H-1,2,4-triazol-1-yl)butan-2-ol, 393) (2R,3R)-3-(5-(bis(4-(trifluoromethyl)benzyl)amino)-3-methyl-2H-indazol-2-yl)-2-(2,4-difluorophenyl)-1-(1H-1,2,4-triazol-1-yl)butan-2-ol, 394) (2R,3R)-3-(5-(bis(2,4-difluorobenzyl)amino)-3-methyl-1H-indazol-1-yl)-2-(2,4-difluorophenyl)-1-(1H-1,2,4-triazol-1-yl)butan-2-ol, 395) (2R,3R)-3-(5-(bis(2,4-dichlorobenzyl)amino)-3-methyl-2H-indazol-2-yl)-2-(2,4-difluorophenyl)-1-(1H-1,2,4-triazol-1-yl)butan-2-ol and, 396) (2R,3R)-3-(5-(4-Chlorobenzylamino)-2H-indazol-2-yl)-2-(2,4-difluorophenyl)-1-(1H-1,2,4-triazol-1-yl)butan-2-ol HCl, or a pharmaceutically acceptable salt thereof.

4. A method for preparing a compound of the following chemical formula 1, an isomer thereof or a pharmaceutically acceptable salt thereof by reacting a compound of the following chemical formula 2 with a compound of the following chemical formula 3 in the presence of a base:

(Chemical Formula 1)

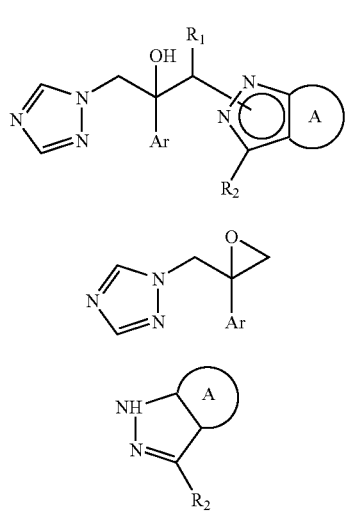

(Chemical Formula 2)

(Chemical Formula 3)

wherein, Ar, $R_1$, $R_2$ and A are as respectively defined in claim 1.

5. The method as defined in claim 4, wherein the base is an inorganic base selected from a group consisting of sodium hydride, potassium carbonate and sodium methoxide, or an organic base selected from a group consisting of triethylamine and 1,8-diazabicyclo[5,4,0]undec-7-en.

6. A method for preparing a compound of the following chemical formula 1, an isomer or a pharmaceutically acceptable salt thereof by reacting a compound of the following chemical formula 4 with a compound of the following chemical formula 5:

(Chemical Formula 1)

(Chemical Formula 4)

(Chemical Formula 5)

Wherein, Ar, $R_1$, $R_2$ and A are as respectively defined in claim 1, and wherein Y is a halogen atom or a methanesulfonyloxy group.

7. An antifungal pharmaceutical composition, comprising the compound as defined in claim 1, an isomer thereof or a pharmaceutically acceptable salt thereof.

8. An antifungal pharmaceutical composition, comprising the compound as defined in claim 2, an isomer thereof or a pharmaceutically acceptable salt thereof.

9. An antifungal pharmaceutical composition, comprising the compound as defined in claim 3, an isomer thereof or a pharmaceutically acceptable salt thereof.

\* \* \* \* \*